(12) United States Patent
Pamula et al.

(10) Patent No.: US 11,789,015 B2
(45) Date of Patent: Oct. 17, 2023

(54) MANIPULATION OF BEADS IN DROPLETS AND METHODS FOR MANIPULATING DROPLETS

(71) Applicant: Advanced Liquid Logic, Inc., San Diego, CA (US)

(72) Inventors: Vamsee K. Pamula, Cary, NC (US); Ramakrishna Sista, Cary, NC (US); Vijay Srinivasan, Cary, NC (US); Michael G. Pollack, Durham, NC (US); Allen E. Eckhardt, Durham, NC (US)

(73) Assignee: ADVANCED LIQUID LOGIC, INC., San Diego, CA (US)

( * ) Notice: Subject to any disclaimer, the term of this patent is extended or adjusted under 35 U.S.C. 154(b) by 261 days.

(21) Appl. No.: 16/948,074

(22) Filed: Sep. 1, 2020

(65) Prior Publication Data

US 2020/0393452 A1    Dec. 17, 2020

Related U.S. Application Data

(60) Continuation of application No. 16/191,270, filed on Nov. 14, 2018, now Pat. No. 10,809,254, which is a
(Continued)

(51) Int. Cl.
*G01N 33/543* (2006.01)
*B01L 3/00* (2006.01)
(Continued)

(52) U.S. Cl.
CPC ....... *G01N 33/54326* (2013.01); *B01F 31/65* (2022.01); *B01F 33/3021* (2022.01);
(Continued)

(58) Field of Classification Search
CPC .. G01N 33/54326; G01N 1/38; B01F 33/451; B01L 3/502792; B01L 2400/0427;
(Continued)

(56) References Cited

U.S. PATENT DOCUMENTS 4,127,460 A    11/1978 Gaske
4,244,693 A    1/1981 Guon
(Continued)

FOREIGN PATENT DOCUMENTS

JP    2006500596    1/2006
JP    2006078225    3/2006
(Continued)

OTHER PUBLICATIONS

"Droplet-Based Digital Microfluidic Genome Sequencing", Abstract from National Institutes of Health Grant No. 1R21HG003706-01, with a project start date of Aug. 1, 2005.
(Continued)

*Primary Examiner* — Brian J. Sines
(74) *Attorney, Agent, or Firm* — Illumina, Inc.

(57) ABSTRACT

Provided herein are methods of splitting droplets containing magnetically responsive beads in a droplet actuator. A droplet actuator having a plurality of droplet operations electrodes configured to transport the droplet, and a magnetic field present at the droplet operations electrodes, is provided. The magnetically responsive beads in the droplet are immobilized using the magnetic field and the plurality of droplet operations electrodes are used to split the droplet into first and second droplets while the magnetically responsive beads remain substantially immobilized.

9 Claims, 19 Drawing Sheets

Related U.S. Application Data division of application No. 15/266,693, filed on Sep. 15, 2016, now Pat. No. 10,139,403, which is a continuation of application No. 14/978,935, filed on Dec. 22, 2015, now Pat. No. 9,494,498, which is a continuation of application No. 14/746,276, filed on Jun. 22, 2015, now Pat. No. 9,377,455, which is a continuation of application No. 14/308,110, filed on Jun. 18, 2014, now Pat. No. 9,086,345, which is a division of application No. 12/761,066, filed on Apr. 15, 2010, now Pat. No. 8,809,068, which is a continuation of application No. PCT/US2008/080264, filed on Oct. 17, 2008, said application No. 12/761,066 is a continuation-in-part of application No. 11/639,531, filed on Dec. 15, 2006.

(60) Provisional application No. 60/980,782, filed on Oct. 17, 2007, provisional application No. 60/807,104, filed on Jul. 12, 2006, provisional application No. 60/806,412, filed on Jun. 30, 2006, provisional application No. 60/746,801, filed on May 9, 2006, provisional application No. 60/746,797, filed on May 9, 2006, provisional application No. 60/745,950, filed on Apr. 28, 2006, provisional application No. 60/745,914, filed on Apr. 28, 2006, provisional application No. 60/745,058, filed on Apr. 18, 2006, provisional application No. 60/745,059, filed on Apr. 18, 2006, provisional application No. 60/745,039, filed on Apr. 18, 2006, provisional application No. 60/745,043, filed on Apr. 18, 2006.

(51) Int. Cl.
| | | |
|---|---|---|
| *B01F 31/65* | (2022.01) | |
| *B01F 33/451* | (2022.01) | |
| *B01F 33/302* | (2022.01) | |
| *B01F 33/3031* | (2022.01) | |
| *G01N 1/38* | (2006.01) | |
| *B01L 7/00* | (2006.01) | |
| *G01N 35/10* | (2006.01) | |

(52) U.S. Cl.
CPC ........ *B01F 33/3031* (2022.01); *B01F 33/451* (2022.01); *B01L 3/50273* (2013.01); *B01L 3/502761* (2013.01); *B01L 3/502792* (2013.01); *G01N 1/38* (2013.01); *B01L 7/52* (2013.01); *B01L 7/525* (2013.01); *B01L 2200/027* (2013.01); *B01L 2200/0647* (2013.01); *B01L 2200/0673* (2013.01); *B01L 2300/06* (2013.01); *B01L 2300/0654* (2013.01); *B01L 2300/089* (2013.01); *B01L 2300/0816* (2013.01); *B01L 2300/0861* (2013.01); *B01L 2300/0864* (2013.01); *B01L 2300/0867* (2013.01); *B01L 2300/1827* (2013.01); *B01L 2400/043* (2013.01); *B01L 2400/0406* (2013.01); *B01L 2400/0415* (2013.01); *B01L 2400/0421* (2013.01); *B01L 2400/0424* (2013.01); *B01L 2400/0427* (2013.01); *B01L 2400/0436* (2013.01); *B01L 2400/0442* (2013.01); *G01N 2001/386* (2013.01); *G01N 2035/1046* (2013.01); *Y10T 436/11* (2015.01); *Y10T 436/25* (2015.01); *Y10T 436/2575* (2015.01); *Y10T 436/25625* (2015.01)

(58) Field of Classification Search
CPC ......... B01L 2400/043; B01L 3/502761; B01L 7/52; B01L 2200/0647; Y10T 436/11
See application file for complete search history.

(56) References Cited

U.S. PATENT DOCUMENTS

| | | | |
|---|---|---|---|
| 4,390,403 | A | 6/1983 | Batchelder |
| 4,454,232 | A | 6/1984 | Breglio et al. |
| 4,636,785 | A | 1/1987 | Le Pesant |
| 4,863,849 | A | 9/1989 | Melamede |
| 5,038,852 | A | 8/1991 | Johnson et al. |
| 5,176,203 | A | 1/1993 | Larzul |
| 5,181,016 | A | 1/1993 | Lee et al. |
| 5,225,332 | A | 7/1993 | Weaver et al. |
| 5,240,994 | A | 8/1993 | Brink et al. |
| 5,266,498 | A | 11/1993 | Tarcha et al. |
| 5,455,008 | A | 10/1995 | Earley et al. |
| 5,472,881 | A | 12/1995 | Beebe |
| 5,486,337 | A | 1/1996 | Ohkawa et al. |
| 5,498,392 | A | 3/1996 | Wilding et al. |
| 5,720,923 | A | 2/1998 | Haff et al. |
| 5,721,851 | A | 2/1998 | Cline et al. |
| 5,770,391 | A | 6/1998 | Foote |
| 5,770,457 | A | 6/1998 | Stocker |
| 5,779,977 | A | 7/1998 | Haff et al. |
| 5,817,526 | A | 10/1998 | Kinoshita et al. |
| 5,827,480 | A | 10/1998 | Haff et al. |
| 5,846,396 | A | 12/1998 | Zanzucchi et al. |
| 5,851,769 | A | 12/1998 | Gray et al. |
| 5,945,281 | A | 8/1999 | Prabhu et al. |
| 5,980,719 | A | 11/1999 | Cherukuri et al. |
| 5,998,224 | A | 12/1999 | Rohr et al. |
| 6,013,531 | A | 1/2000 | Wang et al. |
| 6,033,880 | A | 3/2000 | Haff et al. |
| 6,063,339 | A | 5/2000 | Tisone et al. |
| 6,074,827 | A | 6/2000 | Nelson et al. |
| 6,106,685 | A | 8/2000 | McBride |
| 6,130,098 | A | 10/2000 | Handique et al. |
| 6,143,496 | A | 11/2000 | Brown et al. |
| 6,152,181 | A | 11/2000 | Wapner et al. |
| 6,180,372 | B1 | 1/2001 | Franzen |
| 6,210,891 | B1 | 4/2001 | Nyren et al. |
| 6,258,568 | B1 | 7/2001 | Nyren |
| 6,294,063 | B1 | 9/2001 | Becker et al. |
| 6,319,668 | B1 | 11/2001 | Nova et al. |
| 6,379,929 | B1 | 4/2002 | Burns et al. |
| 6,432,290 | B1 | 8/2002 | Harrison et al. |
| 6,453,928 | B1 | 9/2002 | Kaplan et al. |
| 6,454,924 | B2 | 9/2002 | Jedrzejewski et al. |
| 6,461,570 | B2 | 10/2002 | Ishihara et al. |
| 6,473,492 | B2 | 10/2002 | Prins |
| 6,485,913 | B1 | 11/2002 | Becker |
| 6,538,823 | B2 | 3/2003 | Kroupenkine et al. |
| 6,545,815 | B2 | 4/2003 | Kroupenkine et al. |
| 6,548,311 | B1 | 4/2003 | Knoll |
| 6,565,727 | B1 | 5/2003 | Shenderov et al. |
| 6,596,238 | B1 | 6/2003 | Belder |
| 6,591,852 | B1 | 7/2003 | McNeely et al. |
| 6,613,560 | B1 | 9/2003 | Tso |
| 6,629,826 | B2 | 10/2003 | Yoon |
| 6,632,655 | B1 | 10/2003 | Mehta et al. |
| 6,665,127 | B2 | 12/2003 | Bao et al. |
| 6,673,533 | B1 | 1/2004 | Wohlstadter et al. |
| 6,734,436 | B2 | 5/2004 | Faris et al. |
| 6,759,013 | B2 | 7/2004 | Kaltenbach et al. |
| 6,761,962 | B2 | 7/2004 | Bentsen |
| 6,773,566 | B2 | 8/2004 | Shenderov et al. |
| 6,790,011 | B1 | 9/2004 | Le Pesant et al. |
| 6,828,100 | B1 | 12/2004 | Ronaghi |
| 6,846,638 | B2 | 1/2005 | Shipwash |
| 6,849,461 | B2 | 2/2005 | Eigen et al. |
| 6,868,875 | B2 | 3/2005 | De Beukeleer |
| 6,896,855 | B1 | 5/2005 | Kohler et al. |
| 6,911,131 | B2 | 6/2005 | Miyazaki et al. |
| 6,911,132 | B2 | 6/2005 | Pamula et al. |

(56) References Cited

U.S. PATENT DOCUMENTS

| | | |
|---|---|---|
| 6,924,792 B1 | 8/2005 | Jessop |
| 6,942,776 B2 | 9/2005 | Medoro |
| 6,949,176 B2 | 9/2005 | Vacca et al. |
| 6,955,881 B2 | 10/2005 | Tanaami |
| 6,958,132 B2 | 10/2005 | Chiou et al. |
| 6,841,128 B2 | 11/2005 | Kambara et al. |
| 6,960,437 B2 | 11/2005 | Enzelberger et al. |
| 6,977,033 B2 | 12/2005 | Becker et al. |
| 6,989,234 B2 | 1/2006 | Kolar et al. |
| 6,995,024 B2 | 2/2006 | Smith et al. |
| 7,052,244 B2 | 5/2006 | Fouillet et al. |
| 7,078,168 B2 | 7/2006 | Sylvan et al. |
| 7,150,999 B1 | 12/2006 | Shuck |
| 7,163,612 B2 | 1/2007 | Sterling et al. |
| 7,189,359 B2 | 3/2007 | Yuan |
| 7,189,560 B2 | 3/2007 | Kim et al. |
| 7,211,223 B2 | 5/2007 | Fouillet et al. |
| 7,211,442 B2 | 5/2007 | Gilbert et al. |
| 7,251,392 B2 | 7/2007 | Kuiper et al. |
| 7,255,780 B2 | 8/2007 | Shenderov |
| 7,267,752 B2 | 9/2007 | King et al. |
| 7,294,503 B2 | 11/2007 | Quake et al. |
| 7,310,080 B2 | 12/2007 | Jessop |
| 7,314,567 B2 | 1/2008 | Wagler et al. |
| 7,328,979 B2 | 2/2008 | Deere et al. |
| 7,329,545 B2 | 2/2008 | Pamula et al. |
| 7,438,860 B2 | 10/2008 | Takagi et al. |
| 7,439,014 B1 | 10/2008 | Pamula et al. |
| 7,452,507 B2 | 11/2008 | Renzi et al. |
| 7,454,988 B2 | 11/2008 | Tan |
| 7,458,661 B2 | 12/2008 | Kim et al. |
| 7,459,311 B2 | 12/2008 | Nyren et al. |
| 7,495,031 B2 | 2/2009 | Sakuma et al. |
| 7,531,072 B2 | 5/2009 | Roux et al. |
| 7,547,380 B2 | 6/2009 | Velev |
| 7,556,776 B2 | 7/2009 | Fraden et al. |
| 7,569,129 B2 | 8/2009 | Pamula et al. |
| 7,579,172 B2 | 8/2009 | Cho et al. |
| 7,488,451 B2 | 9/2009 | Sarowitz et al. |
| 7,612,355 B2 | 11/2009 | Wu et al. |
| 7,641,779 B2 | 1/2010 | Becker et al. |
| 7,693,666 B2 | 6/2010 | Griffith et al. |
| 7,727,466 B2 | 6/2010 | Meathrel et al. |
| 7,727,723 B2 | 6/2010 | Pollack et al. |
| 7,759,132 B2 | 7/2010 | Pollack et al. |
| 7,763,471 B2 | 7/2010 | Pamula et al. |
| 7,767,147 B2 | 8/2010 | Adachi et al. |
| 7,767,435 B2 | 8/2010 | Chiu et al. |
| 7,815,871 B2 | 10/2010 | Pamula et al. |
| 7,816,121 B2 | 10/2010 | Pollack et al. |
| 7,821,699 B1 | 10/2010 | Lo et al. |
| 7,822,510 B2 | 10/2010 | Paik et al. |
| 7,851,184 B2 | 12/2010 | Pollack et al. |
| 7,875,160 B2 | 1/2011 | Jary |
| 7,901,947 B2 | 3/2011 | Pollack et al. |
| 7,919,330 B2 | 4/2011 | De Guzman et al. |
| 7,922,886 B2 | 4/2011 | Fouillet et al. |
| 7,939,021 B2 | 5/2011 | Smith et al. |
| 7,943,030 B2 | 5/2011 | Shenderov |
| 7,989,056 B2 | 8/2011 | Plissonier et al. |
| 7,998,436 B2 | 8/2011 | Pollack |
| 8,007,739 B2 | 8/2011 | Pollack et al. |
| 8,041,463 B2 | 10/2011 | Pollack et al. |
| 8,048,628 B2 | 11/2011 | Pollack et al. |
| 8,075,754 B2 | 12/2011 | Sauter-Starace et al. |
| 8,088,578 B2 | 1/2012 | Hua et al. |
| 8,093,062 B2 | 1/2012 | Winger |
| 8,093,064 B2 | 1/2012 | Shah et al. |
| 8,137,917 B2 | 3/2012 | Pollack et al. |
| 8,147,668 B2 | 4/2012 | Pollack et al. |
| 8,179,216 B2 | 5/2012 | Knospe |
| 8,202,686 B2 | 6/2012 | Pamula et al. |
| 8,208,146 B2 | 6/2012 | Srinivasan et al. |
| 8,221,605 B2 | 7/2012 | Pollack et al. |
| 8,236,156 B2 | 8/2012 | Sarrut et al. |
| 8,268,246 B2 | 9/2012 | Srinivasan et al. |
| 8,287,711 B2 | 10/2012 | Pollack et al. |
| 8,292,798 B2 | 10/2012 | Califorrniaa |
| 8,304,253 B2 | 11/2012 | Yi et al. |
| 8,313,698 B2 | 11/2012 | Pollack et al. |
| 8,313,895 B2 | 11/2012 | Pollack et al. |
| 8,317,990 B2 | 11/2012 | Pamula et al. |
| 8,337,778 B2 | 12/2012 | Stone et al. |
| 8,342,207 B2 | 1/2013 | Raccurt et al. |
| 8,349,276 B2 | 1/2013 | Pamula et al. |
| 8,364,315 B2 | 1/2013 | Sturmer et al. |
| 8,388,909 B2 | 3/2013 | Pollack et al. |
| 8,389,297 B2 | 3/2013 | Pamula et al. |
| 8,394,249 B2 | 3/2013 | Pollack et al. |
| 8,394,641 B2 | 3/2013 | Winger |
| 8,426,213 B2 | 4/2013 | Eckhardt et al. |
| 8,439,014 B2 | 5/2013 | Rollinger et al. |
| 8,440,392 B2 | 5/2013 | Pamula et al. |
| 8,444,836 B2 | 5/2013 | Fouillet et al. |
| 8,470,606 B2 | 6/2013 | Srinivasan et al. |
| 8,492,168 B2 | 7/2013 | Srinivasan |
| 8,541,176 B2 | 9/2013 | Pamula et al. |
| 8,613,889 B2 | 12/2013 | Pollack et al. |
| 8,623,889 B2 | 1/2014 | Lyssikatos et al. |
| 8,637,317 B2 | 1/2014 | Pamula et al. |
| 8,637,324 B2 | 1/2014 | Pollack et al. |
| 8,658,111 B2 | 2/2014 | Srinivasan et al. |
| 8,685,754 B2 | 4/2014 | Pollack et al. |
| 8,849,461 B2 | 9/2014 | Ersavas et al. |
| 8,951,721 B2 | 2/2015 | Pollack et al. |
| 8,974,652 B2 | 3/2015 | Gascoyne et al. |
| 8,980,198 B2 | 3/2015 | Srinivasan et al. |
| 9,029,083 B2 | 5/2015 | Griffiths et al. |
| 9,046,514 B2 | 6/2015 | Sista et al. |
| 9,494,498 B2 | 11/2016 | Pamula et al. |
| 9,517,469 B2 | 12/2016 | Shenderov et al. |
| 2001/0008613 A1 | 7/2001 | Kaltenbach et al. |
| 2001/0045358 A1 | 11/2001 | Kopf-Sill et al. |
| 2002/0001544 A1 | 1/2002 | Hess et al. |
| 2002/0005354 A1 | 1/2002 | Spence et al. |
| 2002/0036139 A1 | 3/2002 | Becker et al. |
| 2002/0043463 A1 | 4/2002 | Shenderov |
| 2002/0055167 A1 | 5/2002 | Pourahmadi et al. |
| 2002/0058332 A1 | 5/2002 | Quake et al. |
| 2002/0093651 A1 | 7/2002 | Roe et al. |
| 2002/0102595 A1 | 8/2002 | Davis |
| 2002/0128546 A1 | 9/2002 | Silver |
| 2002/0125135 A1 | 10/2002 | Derand et al. |
| 2002/0142483 A1 | 10/2002 | Yao et al. |
| 2002/0143437 A1 | 10/2002 | Handique et al. |
| 2002/0168671 A1 | 11/2002 | Burns et al. |
| 2002/0172969 A1 | 11/2002 | Burns et al. |
| 2002/0176804 A1 | 11/2002 | Strand et al. |
| 2003/0006140 A1 | 1/2003 | Vacca et al. |
| 2003/0007898 A1 | 1/2003 | Bohm et al. |
| 2003/0012483 A1 | 1/2003 | Ticknor et al. |
| 2003/0012699 A1 | 1/2003 | Moore et al. |
| 2003/0015425 A1 | 1/2003 | Bohm et al. |
| 2003/0049177 A1 | 3/2003 | Smith et al. |
| 2003/0052008 A1 | 3/2003 | Liu et al. |
| 2003/0082081 A1 | 5/2003 | Fouillet et al. |
| 2003/0103021 A1 | 6/2003 | Young et al. |
| 2003/0108452 A1 | 6/2003 | Fuhr et al. |
| 2003/0119057 A1 | 6/2003 | Gascoyne et al. |
| 2003/0129646 A1 | 7/2003 | Briscoe et al. |
| 2003/0155034 A1 | 8/2003 | De Beukeleer et al. |
| 2003/0164295 A1 | 9/2003 | Sterling |
| 2003/0170613 A1 | 9/2003 | Straus |
| 2003/0170686 A1 | 9/2003 | Hoet et al. |
| 2003/0178312 A1 | 9/2003 | Amirkhanian et al. |
| 2003/0183525 A1 | 10/2003 | Elrod et al. |
| 2003/0198576 A1 | 10/2003 | Coyne et al. |
| 2003/0205632 A1 | 11/2003 | Kim et al. |
| 2003/0206351 A1 | 11/2003 | Kroupenkine |
| 2003/0211009 A1 | 11/2003 | Buchanan |
| 2003/0224528 A1 | 12/2003 | Chiou et al. |
| 2003/0227100 A1 | 12/2003 | Chandross et al. |
| 2004/0007377 A1 | 1/2004 | Fouillet et al. |
| 2004/0031688 A1 | 2/2004 | Shenderov |

(56) References Cited

U.S. PATENT DOCUMENTS

| | | |
|---|---|---|
| 2004/0042721 A1 | 3/2004 | Kroupenkine et al. |
| 2004/0055536 A1 | 3/2004 | Kolar et al. |
| 2004/0055871 A1 | 3/2004 | Walton et al. |
| 2004/0055891 A1 | 3/2004 | Pamula et al. |
| 2004/0058407 A1 | 3/2004 | Miller et al. |
| 2004/0058450 A1 | 3/2004 | Pamula et al. |
| 2004/0062685 A1 | 4/2004 | Norton et al. |
| 2004/0086870 A1 | 5/2004 | Tyvoll et al. |
| 2004/0091392 A1 | 5/2004 | McBride et al. |
| 2004/0101445 A1 | 5/2004 | Shvets et al. |
| 2004/0126279 A1 | 7/2004 | Renzi et al. |
| 2004/0136876 A1 | 7/2004 | Fouillet et al. |
| 2004/0141884 A1 | 7/2004 | Unno et al. |
| 2004/0180346 A1 | 9/2004 | Anderson et al. |
| 2004/0197845 A1 | 10/2004 | Hassibi et al. |
| 2004/0209376 A1 | 10/2004 | Natan et al. |
| 2004/0211659 A1 | 10/2004 | Velev |
| 2004/0231987 A1 | 11/2004 | Sterling et al. |
| 2005/0014255 A1 | 1/2005 | Tang et al. |
| 2005/0036908 A1 | 2/2005 | Yu et al. |
| 2005/0037507 A1 | 2/2005 | Gauer |
| 2005/0048581 A1 | 3/2005 | Chiu et al. |
| 2005/0056569 A1 | 3/2005 | Yuan et al. |
| 2005/0064423 A1 | 3/2005 | Higuchi et al. |
| 2005/0079510 A1 | 4/2005 | Berka et al. |
| 2005/0084423 A1 | 4/2005 | Zarowitz et al. |
| 2005/0100675 A1 | 5/2005 | Mao et al. |
| 2005/0106728 A1 | 5/2005 | Burgess et al. |
| 2005/0106742 A1 | 5/2005 | Wahl |
| 2005/0136551 A1 | 6/2005 | Mpock |
| 2005/0148042 A1 | 7/2005 | Prestwich et al. |
| 2005/0158755 A1 | 7/2005 | Lee et al. |
| 2005/0161669 A1 | 7/2005 | Jovanovich et al. |
| 2005/0179746 A1 | 8/2005 | Roux et al. |
| 2005/0189049 A1 | 9/2005 | Ohno et al. |
| 2005/0227264 A1 | 10/2005 | Nobile et al. |
| 2005/0227349 A1 | 10/2005 | Kim et al. |
| 2005/0249636 A1 | 11/2005 | Tacklind et al. |
| 2005/0260686 A1 | 11/2005 | Watkins et al. |
| 2005/0272159 A1 | 12/2005 | Ismagilov et al. |
| 2005/0282224 A1 | 12/2005 | Fouillet et al. |
| 2005/0287572 A1 | 12/2005 | Mathies et al. |
| 2006/0009705 A1 | 1/2006 | Brown |
| 2006/0021875 A1 | 2/2006 | Griffith et al. |
| 2006/0039823 A1 | 2/2006 | Yamakawa et al. |
| 2006/0040375 A1 | 2/2006 | Arney et al. |
| 2006/0054503 A1 | 3/2006 | Pamula et al. |
| 2006/0068450 A1 | 3/2006 | Combette et al. |
| 2006/0102477 A1 | 5/2006 | Vann et al. |
| 2006/0132927 A1 | 6/2006 | Yoon |
| 2006/0164490 A1 | 7/2006 | Kim et al. |
| 2006/0166261 A1 | 7/2006 | Higuchi et al. |
| 2006/0166262 A1 | 7/2006 | Higuchi et al. |
| 2006/0172336 A1 | 8/2006 | Higuchi et al. |
| 2006/0186048 A1 | 8/2006 | Tan |
| 2006/0194331 A1 | 8/2006 | Pamula et al. |
| 2006/0210443 A1 | 9/2006 | Stearns et al. |
| 2006/0231398 A1 | 10/2006 | Sarrut et al. |
| 2006/0254933 A1 | 11/2006 | Adachi et al. |
| 2007/0006296 A1 | 1/2007 | Nakhjiri et al. |
| 2007/0023292 A1 | 2/2007 | Kim et al. |
| 2007/0025879 A1 | 2/2007 | Vandergaw |
| 2007/0037294 A1 | 2/2007 | Pamula et al. |
| 2007/0045117 A1 | 3/2007 | Pamula et al. |
| 2007/0052781 A1* | 3/2007 | Fraden ............ B01L 3/502784 347/96 |
| 2007/0064990 A1 | 3/2007 | Roth |
| 2007/0075922 A1 | 4/2007 | Jessop |
| 2007/0086927 A1 | 4/2007 | Natarajan et al. |
| 2007/0141593 A1 | 6/2007 | Lee et al. |
| 2007/0178603 A1 | 8/2007 | Takii et al. |
| 2007/0179641 A1 | 8/2007 | Lucas et al. |
| 2007/0202538 A1 | 8/2007 | Glezer et al. |
| 2007/0207272 A1 | 9/2007 | Puri et al. |
| 2007/0207513 A1 | 9/2007 | Sorensen et al. |
| 2007/0217956 A1 | 9/2007 | Pamula et al. |
| 2007/0241068 A1 | 10/2007 | Pamula et al. |
| 2007/0242105 A1 | 10/2007 | Srinivasan et al. |
| 2007/0242111 A1 | 10/2007 | Pamula et al. |
| 2007/0243634 A1 | 10/2007 | Pamula et al. |
| 2007/0264723 A1 | 11/2007 | Kim et al. |
| 2007/0267294 A1 | 11/2007 | Shenderov |
| 2007/0275415 A1 | 11/2007 | Srinivasan et al. |
| 2008/0003142 A1 | 1/2008 | Link et al. |
| 2008/0003588 A1 | 1/2008 | Hasson et al. |
| 2008/0006535 A1 | 1/2008 | Paik et al. |
| 2008/0023330 A1 | 1/2008 | Viovy |
| 2008/0038810 A1 | 2/2008 | Pollack et al. |
| 2008/0044893 A1 | 2/2008 | Pollack et al. |
| 2008/0044914 A1 | 2/2008 | Pamula et al. |
| 2008/0050834 A1 | 2/2008 | Pamula et al. |
| 2008/0053205 A1 | 3/2008 | Pollack et al. |
| 2008/0105549 A1 | 5/2008 | Pamela et al. |
| 2008/0113081 A1 | 5/2008 | Hossainy et al. |
| 2008/0124252 A1 | 5/2008 | Marchand et al. |
| 2008/0138815 A1 | 6/2008 | Brown et al. |
| 2008/0142376 A1 | 6/2008 | Fouillet et al. |
| 2008/0151240 A1 | 6/2008 | Roth |
| 2008/0153091 A1 | 6/2008 | Brown et al. |
| 2008/0160525 A1 | 6/2008 | Brown et al. |
| 2008/0166793 A1 | 7/2008 | Beer et al. |
| 2008/0169184 A1 | 7/2008 | Brown et al. |
| 2008/0171324 A1 | 7/2008 | Brown et al. |
| 2008/0171325 A1 | 7/2008 | Brown et al. |
| 2008/0171326 A1 | 7/2008 | Brown et al. |
| 2008/0171327 A1 | 7/2008 | Brown et al. |
| 2008/0171382 A1 | 7/2008 | Brown et al. |
| 2008/0210558 A1 | 9/2008 | Sauter-Starace et al. |
| 2008/0213766 A1 | 9/2008 | Brown et al. |
| 2008/0247920 A1 | 10/2008 | Pollack et al. |
| 2008/0264797 A1 | 10/2008 | Pamula et al. |
| 2008/0274513 A1 | 11/2008 | Shenderov et al. |
| 2008/0281471 A1 | 11/2008 | Smith et al. |
| 2008/0283414 A1 | 11/2008 | Monroe et al. |
| 2008/0302431 A1 | 12/2008 | Marchand et al. |
| 2008/0305481 A1 | 12/2008 | Whitman et al. |
| 2009/0014394 A1 | 1/2009 | Yi et al. |
| 2009/0042319 A1 | 2/2009 | De Guzman et al. |
| 2009/0053726 A1 | 2/2009 | Owen et al. |
| 2009/0127123 A1 | 5/2009 | Raccurt et al. |
| 2009/0134027 A1 | 5/2009 | Jary |
| 2009/0142564 A1 | 6/2009 | Plissonnier et al. |
| 2009/0155902 A1 | 6/2009 | Pollack et al. |
| 2009/0192044 A1 | 7/2009 | Fouillet |
| 2009/0260988 A1 | 10/2009 | Pamula et al. |
| 2009/0263834 A1 | 10/2009 | Sista et al. |
| 2009/0280251 A1 | 11/2009 | De Guzman et al. |
| 2009/0280475 A1 | 11/2009 | Pollack et al. |
| 2009/0280476 A1 | 11/2009 | Srinivasan et al. |
| 2009/0283407 A1 | 11/2009 | Shah et al. |
| 2009/0288710 A1 | 11/2009 | Viovy et al. |
| 2009/0291433 A1 | 11/2009 | Pollack et al. |
| 2009/0304944 A1 | 12/2009 | Sudarsan et al. |
| 2009/0311713 A1 | 12/2009 | Pollack et al. |
| 2009/0321262 A1 | 12/2009 | Adachi et al. |
| 2010/0025242 A1 | 2/2010 | Pamula et al. |
| 2010/0025250 A1 | 2/2010 | Pamula et al. |
| 2010/0028920 A1 | 2/2010 | Eckhardt |
| 2010/0032293 A1 | 2/2010 | Pollack et al. |
| 2010/0041086 A1 | 2/2010 | Pamula et al. |
| 2010/0048410 A1 | 2/2010 | Shenderov et al. |
| 2010/0062508 A1 | 3/2010 | Pamula et al. |
| 2010/0068764 A1 | 3/2010 | Sista et al. |
| 2010/0087012 A1 | 4/2010 | Shenderov et al. |
| 2010/0096266 A1 | 4/2010 | Kim et al. |
| 2010/0116640 A1 | 5/2010 | Pamula et al. |
| 2010/0118307 A1 | 5/2010 | Srinivasan et al. |
| 2010/0120130 A1 | 5/2010 | Srinivasan et al. |
| 2010/0126860 A1 | 5/2010 | Srinivasan et al. |
| 2010/0130369 A1 | 5/2010 | Shenderov et al. |
| 2010/0140093 A1 | 6/2010 | Pamula et al. |
| 2010/0143963 A1 | 6/2010 | Pollack |
| 2010/0151439 A1 | 6/2010 | Pamula et al. |
| 2010/0190263 A1 | 7/2010 | Srinivasan et al. |

(56) References Cited

U.S. PATENT DOCUMENTS

| | | |
|---|---|---|
| 2010/0194408 A1 | 8/2010 | Sturmer et al. |
| 2010/0213074 A1 | 8/2010 | Mousa et al. |
| 2010/0221713 A1 | 9/2010 | Pollack et al. |
| 2010/0236927 A1 | 9/2010 | Pope et al. |
| 2010/0236928 A1 | 9/2010 | Srinivasan et al. |
| 2010/0236929 A1 | 9/2010 | Pollack et al. |
| 2010/0258441 A1 | 10/2010 | Sista et al. |
| 2010/0270156 A1 | 10/2010 | Srinivasan et al. |
| 2010/0279374 A1 | 11/2010 | Sista et al. |
| 2010/0282608 A1 | 11/2010 | Srinivasan et al. |
| 2010/0282609 A1 | 11/2010 | Pollack et al. |
| 2010/0291578 A1 | 11/2010 | Pollack et al. |
| 2010/0307917 A1 | 12/2010 | Srinivasan et al. |
| 2010/0320088 A1 | 12/2010 | Fouillet et al. |
| 2010/0323405 A1 | 12/2010 | Pollack et al. |
| 2011/0076692 A1 | 3/2011 | Sista et al. |
| 2011/0086377 A1 | 4/2011 | Thwar et al. |
| 2011/0091989 A1 | 4/2011 | Sista et al. |
| 2011/0097763 A1 | 4/2011 | Pollack et al. |
| 2011/0100823 A1 | 5/2011 | Pollack et al. |
| 2011/0104725 A1 | 5/2011 | Pamula et al. |
| 2011/0104747 A1 | 5/2011 | Pollack et al. |
| 2011/0104816 A1 | 5/2011 | Pollack et al. |
| 2011/0114490 A1 | 5/2011 | Pamula et al. |
| 2011/0118132 A1 | 5/2011 | Winger et al. |
| 2011/0147215 A1 | 6/2011 | Fuchs et al. |
| 2011/0180571 A1 | 7/2011 | Srinivasan et al. |
| 2011/0186433 A1 | 8/2011 | Pollack et al. |
| 2011/0203930 A1 | 8/2011 | Pamula et al. |
| 2011/0209998 A1 | 9/2011 | Shenderov |
| 2011/0213499 A1 | 9/2011 | Sturmer et al. |
| 2011/0303542 A1 | 12/2011 | Srinivasan et al. |
| 2011/0311980 A1 | 12/2011 | Pollack et al. |
| 2012/0018306 A1 | 1/2012 | Srinivasan et al. |
| 2012/0044299 A1 | 2/2012 | Winger |
| 2012/0132528 A1 | 5/2012 | Shenderov et al. |
| 2012/0136147 A1 | 5/2012 | Winger |
| 2012/0165238 A1 | 6/2012 | Pamula et al. |
| 2013/0017544 A1 | 1/2013 | Eckhardt et al. |
| 2013/0018611 A1 | 1/2013 | Sturmer |
| 2013/0059366 A1 | 3/2013 | Pollack et al. |
| 2013/0217113 A1 | 8/2013 | Srinivasan et al. |
| 2013/0217583 A1 | 8/2013 | Link et al. |
| 2013/0280131 A1 | 10/2013 | Handique et al. |
| 2014/0302580 A1 | 6/2014 | Sista |
| 2015/0285792 A1 | 6/2015 | Sista |
| 2017/0003282 A1 | 1/2017 | Pamula et al. |

FOREIGN PATENT DOCUMENTS

| | | | |
|---|---|---|---|
| JP | 2006276801 | 10/2006 | |
| JP | 2006317364 | 11/2006 | |
| JP | 2006329899 | 12/2006 | |
| JP | 2006329904 | 12/2006 | |
| JP | 2008096590 | 4/2008 | |
| WO | 1998022625 | 5/1998 | |
| WO | 1999015876 | 4/1999 | |
| WO | 1999017093 | 4/1999 | |
| WO | 1999054730 | 10/1999 | |
| WO | WO-0050172 A1 * | 8/2000 | ............ B01L 3/5027 |
| WO | 2000069565 | 11/2000 | |
| WO | 2000073655 | 12/2000 | |
| WO | 2001007159 | 2/2001 | |
| WO | 2003045556 | 6/2003 | |
| WO | 2003069380 | 8/2003 | |
| WO | 2004007377 | 1/2004 | |
| WO | 2004011938 | 2/2004 | |
| WO | 2004027490 | 4/2004 | |
| WO | 2004029585 | 4/2004 | |
| WO | 2004030820 | 4/2004 | |
| WO | WO-2004071638 A2 * | 8/2004 | .......... B01F 13/0062 |
| WO | 2004073863 | 9/2004 | |
| WO | 2005047696 | 5/2005 | |
| WO | 2005069015 | 7/2005 | |
| WO | 2006003292 | 1/2006 | |
| WO | 2006013303 | 2/2006 | |
| WO | 2006026351 | 3/2006 | |
| WO | 2006070162 | 7/2006 | |
| WO | 2006081558 | 8/2006 | |
| WO | 2006085905 | 8/2006 | |
| WO | 2006124458 | 11/2006 | |
| WO | 2006127451 | 11/2006 | |
| WO | 2006129486 | 12/2006 | |
| WO | 2006132211 | 12/2006 | |
| WO | 2006134307 | 12/2006 | |
| WO | 2006138543 | 12/2006 | |
| WO | 2007003720 | 1/2007 | |
| WO | 2007012638 | 2/2007 | |
| WO | 2007033990 | 3/2007 | |
| WO | 2007048111 | 4/2007 | |
| WO | 2007094739 | 8/2007 | |
| WO | 2007120240 | 10/2007 | |
| WO | 2007120241 | 10/2007 | |
| WO | 2007123908 | 11/2007 | |
| WO | 2007133710 | 11/2007 | |
| WO | 2008051310 | 5/2008 | |
| WO | 2008055256 | 5/2008 | |
| WO | 2008068229 | 6/2008 | |
| WO | 2008091848 | 7/2008 | |
| WO | 2008098236 | 8/2008 | |
| WO | 2008101194 | 8/2008 | |
| WO | 2008106678 | 9/2008 | |
| WO | 2008109664 | 9/2008 | |
| WO | 2008112856 | 9/2008 | |
| WO | 2008116209 | 9/2008 | |
| WO | 2008116221 | 9/2008 | |
| WO | 2008118831 | 10/2008 | |
| WO | 2008124846 | 10/2008 | |
| WO | 2008131420 | 10/2008 | |
| WO | 2008134153 | 11/2008 | |
| WO | 2009002920 | 12/2008 | |
| WO | 2009003184 | 12/2008 | |
| WO | 2009011952 | 1/2009 | |
| WO | 2009021173 | 2/2009 | |
| WO | 2009021233 | 2/2009 | |
| WO | 2009026339 | 2/2009 | |
| WO | 2009029561 | 3/2009 | |
| WO | 2009032863 | 3/2009 | |
| WO | 2009052095 | 4/2009 | |
| WO | 2009052123 | 4/2009 | |
| WO | 2009052321 | 4/2009 | |
| WO | 2009052345 | 4/2009 | |
| WO | 2009052348 | 4/2009 | |
| WO | 2009076414 | 6/2009 | |
| WO | 2009086403 | 7/2009 | |
| WO | 2009111769 | 9/2009 | |
| WO | 2009135205 | 11/2009 | |
| WO | 2009137415 | 11/2009 | |
| WO | 2009140373 | 11/2009 | |
| WO | 2009140671 | 11/2009 | |
| WO | 2010004014 | 1/2010 | |
| WO | 2010006166 | 1/2010 | |
| WO | 2010009463 | 1/2010 | |
| WO | 2010019782 | 2/2010 | |
| WO | 2010027894 | 3/2010 | |
| WO | 2010042637 | 4/2010 | |
| WO | 2010077859 | 7/2010 | |
| WO | 2011002957 | 1/2011 | |
| WO | 2011020011 | 2/2011 | |
| WO | 2011057197 | 5/2011 | |
| WO | 2011084703 | 7/2011 | |
| WO | 2011126892 | 10/2011 | |
| WO | 2012009320 | 1/2012 | |
| WO | 2012012090 | 1/2012 | |
| WO | 2012037308 | 3/2012 | |
| WO | 2012068055 | 5/2012 | |
| WO | 2013009927 | 1/2013 | |

OTHER PUBLICATIONS

"Final Office Action from related U.S. Appl. No. 14/639,612", dated Jan. 6, 2016.

(56) References Cited

OTHER PUBLICATIONS

"Lab-on-a-Chip Technology May Present New ESD Challenges", Electrostatic Discharge Journal, Mar. 2002.
"Method and device for screening molecules in cells", U.S. Appl. No. 10/522,175, which was based on International Application No. PCT/FR2003/002298., Jan. 24, 2005.
"Nanoliter Labon-A-Chip for Rapid Parallel Immunoassays", Published Abstract from NIH Grant Project No. CA114993, project start date of Jul. 1, 2006.
"Notice of Allowance and Examiner Interview Summary dated Sep. 4, 2008 from co-pending U.S. Appl. No. 11/639,736", dated Sep. 4, 2008.
"Office Action dated Jul. 22, 2008 from co-pending U.S. Appl. No. 11/639,736", dated Jul. 22, 2008.
"Office Action from co-pending U.S. Appl. No. 11/639,736", dated Apr. 7, 2008.
"PCT International Search Report and Written Opinion for PCT/US2006/047481", dated May 5, 2008.
"PCT International Search Report and Written Opinion for PCT/US2006/047486", dated May 2, 2008.
"PCT International Search Report and Written Opinion for PCT/US2007/009379", dated Aug. 18, 2008.
"PCT International Search Report and Written Opinion for PCT/US2007/011298", dated Jun. 25, 2008.
"PCT International Search Report and Written Opinion for PCT/US2009/059868", dated May 19, 2010.
"Response to Office Action dated Apr. 22, 2008 from co-pending U.S. Appl. No. 11/639,736", dated Apr. 22, 2008.
"Response to Office Action dated Jul. 28, 2008 from co-pending U.S. Appl. No. 11/639,736", dated Jul. 28, 2008.
"U.S. Appl. No. 12/465,935 Rule 1.132 Declaration Gaurav Jitendra Shah", Jun. 30, 2011.
Abstract from National Institutes of Health Grant No. 5U01AI066590-02 titled "Microfluidic PCR Platform to Detect Microbial DNA", project start date of Jul. 5, 2005.
Agah, "DNA Analysis Chip by Electrowetting Actuation", Stanford Nanofabrication Facility, 2002, 9.
Al-Rubeai et al., "The effect of Pluronic F-68 on hybridoma cells in continuous culture", Applied Microbiology and Biology, 1992, 44-45.
Bali et al., "Comparison of methods for the analysis of lysosomal enzyme activities in quality control dried blood spot specimens", 2013 International Conference on Inborn Errors of Metabolism (ISIEM): India. New Delhi, India. Poster presentation, abstract published in conference proceedings, Apr. 4-7, 2013.
Bali et al., "Comparison of Methods for the Analysis of Lysosomal Enzyme Activities in Quality Control Dried Blood Spot Specimens", LSD World Meeting, Orlando, FL, poster presented, Feb. 12-15, 2013.
Bali et al., "Digital microfluidics: a single multiplex platform for rapid newborn screening", 2013 International Conference on Inborn Errors of Metabolism (IEM): India, New Delhi, India, oral presentation,poster presentation, abstract published in conf. proceedings, Apr. 4-7, 2013.
Barbulovic-Nad et al., "A microfluidic platform for complete mammalian cell culture", Lab on a chip, vol. 10, Apr. 2010, 1536-1542.
Barbulovic-Nad et al., "Digital microfluidics for cell-based assays", Lab on a chip, vol. 8, Apr. 2008, 519-526.
Batchelder et al., "Dielectrophoretic manipulator", Review of Scientific Instruments, vol. 54 ., 1983, 300-302.
Baviere et al., "Dynamics of droplet transport induced by electrowetting actuation", Microfluidics and Nanofluidics, vol. 4, May 2007, pp. 287-294.
Becker et al., "Polymer microfluidic devices", Talanta, vol. 56, Feb. 2002, 267-287.
Becker, "Mind the gap!", Lab on a chip, vol. 10, Feb. 2010, 271-273.
Benton et al., "Library Preparation Method 1 DNA Library Construction for Illumina SBS Sequencing Platforms using NEBNext® Library Preparation Reagents", Application Note, NuGEN, 2011.

Bhansali et al., "Resolving chemical/bio-compatibility in microfluidic MEMS systems", SPIE Conference on Microfluidic Devices and Systems II, vol. 3877, 1999, 101-109.
Binks, "Wetting: theory and experiment", Current Opinion in Colloids and Interface Science, vol. 6, No. 1, 2001, 17-21.
Boles et al., "Droplet-Based Pyrosequencing Using Digital Microfluidics", Analytical Chemistry, vol. 83, Sep. 2011, 8439-47.
Bottausci et al., "Fully Integrated EWOD Based Bio-Analysis Device", Labautomation 2011, Palm Springs Convention Center, Palm Springs, CA, USA; Abstract in Proceedings on line, poster distributed, Jan. 29-Feb. 2, 2011.
Brady, "Electrowetting for DNA Sequencing on Chip", NNIN REU Research Accomplishments, 2004, 26-27.
Brassard et al., "Water-oil core-shell droplets for electrowetting-based digital microfluidic devices", Lab on a chip, vol. 8, 2008, 1342-1349.
Burde et al., "Digital Microfluidic Rapid HIV Point-of-Care Diagnostic Device for Resource Limited Settings", Workshop on TB and HIV Diagnostics, Silver Spring, MD. (Poster, copies distributed to attendees.) http://www.blsmeetings.net/TB-HIV-Dx-Wkshop/index.cfm, Jun. 28, 2011.
Burton et al., "Diagnosis of Fabry and Gaucher diseases from the Pilot Screening of Newborns for Lysosomal Storage Disorders in Illinois", APHL Newborn Screening and Genetic Testing Symposium, San Diego, 2011.
Chakrabarty et al., "Design Automation Challenges for Microfluidics-Based Biochips", DTIP of MEMS & MOEMS, Montreux, Switzerland, Jun. 1-3, 2005.
Chakrabarty et al., "Design Automation for Microfluidics-Based Biochips", ACM Journal on Engineering Technologies in Computing Systems , 1(3), Oct. 2005, pp. 186-223.
Chakrabarty, "Automated Design of Microfluidics-Based Biochips: connecting Biochemistry of Electronics CAD", IEEE International Conference on Computer Design, San Jose, CA, Oct. 1-4, 2006, 93-100.
Chakrabarty, "Design, Testing, and Applications of Digital Microfluidics-Based Biochips", Proceedings of the 18th International Conf. on VLSI held jointly with 4th International Conf. on Embedded Systems Design (VLSID'05), IEEE, Jan. 3-7, 2005, 39 pages.
Chamberlain et al., "#17 Deletion screening of Duchenne musular dystrophy locus via multiplex DNA amplification", Nuc. Acid. Res. 16, 1988, pp. 11141-56.
Chang et al., "Integrated polymerase chain reaction chips utilizing digital microfluidics", Biomedical Microdevices, vol. 8, May 20, 2006, 215-225.
Chatterjee et al., "Droplet-based microfluidics with nonaqueous solvents and solutions", Lab on a Chip, vol. 6., Feb. 2006, 199-206.
Chatterjee et al., "Lab on a Chip Applications with a Digital Microfluidic Platform", UCLA Dissertation, UMI Microform No. 3342975, 2008, 186 pages.
Chen et al., "Development of Mesoscale Actuator Device with Micro Interlocking Mechanism", J. Intelligent Material Systems and Structures, vol. 9, No. 4, Jun. 1998, pp. 449-457.
Chen et al., "Mesoscale Actuator Device with Micro Interlocking Mechanism", Proc. IEEE Micro Electro Mechanical Systems Workshop, Heidelberg, Germany, Jan. 1998, pp. 384-389.
Chen et al., "Mesoscale Actuator Device: Micro Interlocking Mechanism to Transfer Macro Load", Sensors and Actuators, vol. 73, Issues 1-2, Mar. 1999, pp. 30-36.
Chin et al., "Lab-on-a-chip devices for global health past studies and future opportunities", Lab on a Chip, vol. 7, Jan. 2007, pp. 41-57.
Chiou et al., "Light actuation of liquid by optoelectrowetting", Sensors and Actuators A: Physical, vol. 104, May 2003, 222-228.
Cho et al., "Concentration and binary separation of micro particles for droplet-based digital microfludics", Lab Chip, vol. 7, 2007, 490-498.
Cho et al., "Creating, Transporting, Cutting, and Merging Liquid Droplets by Electrowetting-Based Actuation for Digital Microfluidic Circuits", Journal of Microelectromechanical Systems, vol. 12, No. 1, Feb. 2003, 70-80.
Cho et al., "Splitting a Liquid Droplet for Electrowetting-Based Microfluidics", Proceedings of 2001 ASME International Mechani-

(56) References Cited

OTHER PUBLICATIONS cal Engineering Congress and Exposition, IMECE2001/MEMS-23830, New York, NY, Nov. 11-16, 2001, 7 pages.
Cohen, "Automated Multianalyte Screening Tool for Classification of Forensic Samples", NIJ conference 2012, http://www.nij.gov/nij/events/nij_conference/2012/nij-2012-program-book.pdf, 2012.
Cohen, "Digital Microfluidic Sample Prep & Bioanalytical Systems", BioDot Workshop: From R&D to Quantitative IVDs, Irvine, CA, Apr. 24, 2012.
Cohen, "Low Cost Sample-to-Sequence Device for Human & Pathogen ID", Integrating Sample Prep, Baltimore, MD, Oct. 18, 2012.
Colgate et al., "An Investigation of Electrowetting-based Microactuation", Journal of Vacuum Science & Technology A—Vacuume Surfaces and Films, vol. 8 (4), Jul.-Aug. 1990, 3625-3633.
Coltro et al., "Toner and paper-based fabrication techniques for microfluidic applications", Electrophoresis, vol. 31, Jul. 2010, 2487-2498.
Cooney et al., "Electrowetting droplet microfluidics on a single planar surface", Microfluidics and Nanofluidics,vol. 2., Mar. 2006, 435-446.
Office Action from co-pending U.S. Appl. No. 11/639,822, dated Feb. 17, 2010.
Office Action from co-pending U.S. Appl. No. 11/639,822, dated Mar. 16, 2011.
Office Action from co-pending U.S. Appl. No. 11/639,822, dated May 28, 2010.
Office Action from co-pending U.S. Appl. No. 11/639,822, dated May 6, 2010.
Office Action from corresponding U.S. Appl. No. 11/639,663, dated Jul. 14, 2010.
Office Action from corresponding U.S. Appl. No. 11/639,663, dated Jun. 24, 2010.
Office Action from corresponding U.S. Appl. No. 11/639,663, dated Nov. 26, 2010.
Response Office Action from co-pending U.S. Appl. No. 11/639,822, dated Feb. 23, 2010.
Response Office Action from co-pending U.S. Appl. No. 11/639,822, dated Jul. 18, 2011.
Response Office Action from co-pending U.S. Appl. No. 11/639,822, dated Jun. 21, 2010.
Response Office Action from co-pending U.S. Appl. No. 11/639,822, dated May 18, 2010.
Response to Office Action from co-pending U.S. Appl. No. 11/639,663, dated Mar. 24, 2011.
Response to Office Action from corresponding U.S. Appl. No. 11/639,663, dated Apr. 6, 2010.
Response to Office Action from corresponding U.S. Appl. No. 11/639,663, dated Jul. 14, 2010.
Response to Office Action from corresponding U.S. Appl. No. 11/639,663, dated Jul. 8, 2010.
Cotten et al., "Digital Microfluidics: a novel platform for multiplexed detection of lysosomal storage diseases", Abstract # 3747.9. Pediatric Academic Society Conference, 2008.
Delapierre et al., "SmartDrop: An Integrated System from Sample Collection to Result using real-time PCR", 4th National Bio-Threat Conference, New Orleans, LA, USA; Poster presented at conference., Dec. 7-9, 2010.
Delattre et al., "Macro to microfluidics system for biological environmental monitoring", Biosensors and Bioelectronics, vol. 36, Issue 1, Available online, Apr. 27, 2012, 230-235.
Delattre et al., "SmartDrop: An integrated system from sample preparation to analysis using real-time PCR", 10th International Symposium on Protection against Chemical and Biological Warfare Agents; Stockholm, Sweden; Abstract, paper, Jun. 8-11, 2010.
Delattre et al., "Towards an industrial fabrication process for electrowetting chip using standard MEMS Technology", µTAS2008, San Diego; Abstract in proceedings, Oct. 13-16, 2008, 1696-1698.
Delattre, Movie in news on TF1 (Cyril Delattre), http://videos.tf1.fr/jt-we/zoom-sur-grenoble-6071525.html, 2009, (English translation of audio), 2009.
Delattre, Movie in talk show "C Dans l'air" (at 24" Cyril Delattre), http://www.france5.fr/c-dans-l-air/sante/bientot-vous-ne-serez-plus-malade-31721, 2009, (English translation of audio), 2009.
Delattre, Movie on Web TV—Cite des sciences (at 3'26" Cyril Delattre), http://www.universcience.tv/videolaboratoire-de-poche-793.html, 2009, (English translation of audio), 2009.
Dewey et al., "Visual modeling and design of microelectromechanical system transducers", Microelectronics Journal, vol. 32, Apr. 2001, 373-381.
Dewey, "Towards a Visual Modeling Approach to Designing Microelectromechanical System Transducers", Journal of Micromechanics and Microengineering, vol. 9, Dec. 1999, 332-340.
Ding, "System level architectural optimization of semi-reconfigurable micro fluidic system", M.S. Thesis, Duke University Dept of Electrical Engineering, 2000.
Dorfman et al., "Contamination-Free Continuouse Flow Microfluidic Polymerase Chain Reaction for Quantitative and Clinical Applications", Analytical Chemistry 77, 2005, 3700-3704.
Dubois et al., "Ionic Liquid Droplet as e-Microreactor", Analytical Chemistry, vol. 78, 2006, 4909-4917.
Eckhardt et al., "Development and validation of a single-step fluorometric assay for Hunter syndrome", APHL Newborn Screening and Genetic Testing Symposium, San Diego, 2011.
Emani et al., "Novel microfluidic platform for automated lab-on-chip testing of hypercoagulability panel", Blood Coagulation and Fibrinolysis, vol. 23(8), 2012, 760-8.
Emani et al., "Novel Microfluidic Platform for Point of Care Hypercoagulability Panel Testing", Circulation, vol. 122, 2010, A14693.
European Search Report, "Application No. 13183436.8", dated Oct. 29, 2013.
Examiner Interview Summary Record from U.S. Appl. No. 11/639,736, dated Apr. 28, 2008.
Examiner Interview Summary Record from U.S. Appl. No. 11/639,736, dated Sep. 4, 2008.
Fair et al., "A Micro-Watt Metal-Insulator-Solution-Transport (MIST) Device for Scalable Digital Bio-Microfluidic Systems", IEEE IEDM Technical Digest, 2001, 16.4.1-4.
Fair et al., "Advances in droplet-based bio lab-on-a-chip", BioChips, Boston, 2003.
Fair et al., "Bead-Based and Solution-Based Assays Performed on a Digital Microfluidic Platform", Biomedical Engineering Society (BMES) Fall Meeting, Baltimore, MD, Oct. 1, 2005.
Fair et al., "Chemical and Biological Applications of Digital-Microfluidic Devices", IEEE Design & Test of Computers, vol. 24(1), Jan.-Feb. 2007, 10-24.
Fair et al., "Chemical and biological pathogen detection in a digital microfluidic platform", DARPA Workshop on Microfluidic Analyzers for DoD and National Security Applications, Keystone, CO, 2006.
Fair et al., "Electrowetting-based On-Chip Sample Processing for Integrated Microfluidics", IEEE Inter. Electron Devices Meeting (IEDM), 2003, 32.5.1-32.5.4.
Fair et al., "Integrated chemical/biochemical sample collection, pre-concentration, and analysis on a digital microfluidic lab-on-a-chip platform", Lab-on-a-Chip: Platforms, Devices, and Applications, Conf. 5591, SPIE Optics East, Philadelphia, Oct. 25-28, 2004.
Fair, "Biomedical Applications of Electrowetting Systems", 5th International Electrowetting Meeting, Rochester, NY, May 31, 2006.
Fair, "Digital microfluidics: is a true lab-on-a-chip possible?", Microfluid Nanofluid, vol. 3, Mar. 8, 2007, 245-281.
Fair, "Droplet-based microfluidic genome sequencing", NHGRI PI's meeting, Boston, 2005.
Fair, "Scaling of Digital Microfluidic Devices for Picoliter Applications", The 6th International Electrowetting Meeting, Aug. 20-22, 2008, p. 14.
Fan, "Digital Microfluidics by Cross-Reference EWOD Actuation: Principle, Device and System", PhD Dissertation, University of California Dept. of Mechanical Engineering, 2003.

(56) References Cited

OTHER PUBLICATIONS

Final Office Action (U.S. Office Action (Final) mailed in U.S. Appl. No. 11/639,594), dated Nov. 10, 2010.
Final Office Action (U.S. Office Action (Final) mailed in U.S. Appl. No. 11/639,594), dated Apr. 7, 2011.
Final Office Action (U.S. Office Action (Final) mailed in U.S. Appl. No. 11/639,594), dated May 22, 2014.
Final Office Action (U.S. Office Action (Final) mailed in U.S. Appl. No. 11/639,594), dated Jun. 4, 2010.
Final Office Action (U.S. Office Action (Final) mailed in U.S. Appl. No. 11/639,594), dated Jul. 23, 2014.
Final Office Action (U.S. Office Action (Final) mailed in U.S. Appl. No. 11/639,594), dated Aug. 4, 2014.
Fouillet et al., "Design and Validation of a Complex Generic Fluidic Microprocessor Based on EWOD Droplet for Biological Applications", 9th International Conference on Miniaturized Systems for Chem and Life Sciences, Boston, MA, Oct. 9-13, 2005, 58-60.
Fouillet et al., "Digital microfluidic design and optimization of classic and new fluidic functions for lab on a chip systems", Microfluid Nanofluid 4, 2008, 159-165.
Fouillet, "Bio-Protocol Integration in Digital Microfluidic Chips", The 6th International Electrowetting Meeting, Aug. 20-22, 2008, p. 15.
Fowler, "Lab-on-a-Chip Technology May Present New ESD Challenges", Electrostatic Discharge (ESD) Journal. Retrieved on Apr. 18, 2008 from:http://www.esdjournal.com/articles/labchip/Lab.htm., Mar. 2002.
Furdui et al., "Immunomagnetic T cell recapture from blood for PCR analysis using microfluidic systems", Lab Chip vol. 4, 2004, 614-618.
Garrell et al., "Preventing Biomolecular Absorption in Electrowetting-Based Biofluidic Chips", Analytical Chemistry, vol. 75, Oct. 2003, 5097-5102.
Gijs, "magnetic bead handling on-chip:new opportunities for analytical applications", Microfluidics and Nanofluidics, vol. 1, Oct. 2, 2004, 22-40.
Gong et al., "Direct-referencing two-dimensional-array digital microfluidics using multi-layer printed circuit board", Journal of Microelectromechanical Systems, vol. 17, Apr. 2008, 257-264.
Graham et al., "Fluorometric reagent kits for screening Lysosomal Storage Disorders: One year stability evaluation and shelf-life recommendations", Extended abstract from the 2013 APHL Newborn Screening and Genetic Testing Symposium and the International Society for Neonatal Screening, Atlanta, GA, Published online only behind a password protected website accessible only to conference attendees per S. Wilhelm on Nov. 26, 2013. Add to master list per BB on Nov. 27, 2013, 2013.
Graham et al., "Development of Quality Control Spots for Lysosomal Storage Disorders under cGMP", APHL Newborn Screening and Genetic Testing Symposium, San Diego, 2011.
Graham et al., "Fluorometric reagent kits for screening Lysosomal Storage Disorders: One year stability evaluation and shelf-life recommendations", 2013 APHL Newborn Screening and Genetic Testing Symposium and the International Society for Neonatal Screening, Atlanta, GA. Poster presented, abstract published in conference proceedings, May 5-10, 2013.
Guttenberg et al., "Planar chip devices for PCR and hybridization with surface acoustic wave pump", Lab on a chip, vol. 5, Mar. 2005, 12617-22.
Hua et al., "Multiplexed real-time polymerase chain reaction on a digital microfluidic platform", Analytical Chemistry, vol. 82, No. 6, Mar. 15, 2010, Published on Web, Feb. 12, 2010, 2310-2316.
Hua et al., "Rapid Detection Of Methicillin-Resistant *Staphylococcus aureus* (MRSA) Using Digital Microfluidics", 12th Intl Conference on Miniaturized Systems for Chemistry and Life Sciences, Proc. µTAS, Oct. 12-16, 2008.
Huang et al., "MEMS-based sample preparation for molecular diagnostics", Analytical and Bioanalytical Chemistry, vol. 372, 2002, 49-65.
Huebner et al., "Microdroplets:a sea of applications?", Lab on a Chip, vol. 8, Aug. 2008, 1244-1254.
International Preliminary Report on Patentability dated Apr. 20, 2010 from PCT International Application No. PCT/US2008/080264, dated Apr. 20, 2010.
International Preliminary Report on Patentability dated Mar. 27, 2009 from PCT International Application No. PCT/US2006/047481, dated Mar. 27, 2009.
International Preliminary Report on Patentability for PCT International Application No. PCT/US2008/080264, dated May 27, 2009.
International Search Report and Written Opinion dated Feb. 28, 2007 from PCT International Application No. PCT/US2005/030247, dated Feb. 28, 2007.
Jary et al., "Development of complete analytical system for Environment and homeland security", 14th International Conference on Biodetection Technologies 2009, Technological Responses to Biological Threats, Baltimore, MD; Abstract in Proceedings, poster distributed at conference, Jun. 25-26, 2009, 663.
Jary et al., "SmartDrop, Microfluidics for Biology", Forum 4i 2009, Grenoble, France; Flyer distributed at booth, May 14, 2009.
Jebrail et al., "Lets get digital: digitizing chemical biology with microfluidics", Current Opinion in Chemical Biology, vol. 14, Oct. 2010, 574-581.
Jinks et al., "Newborn Screening for Krabbe and other Lysosomal Storage Diseases", The 3rd Annual Workshop on Krabbe Disease, Java Center, New York, Jul. 19-21, 2010.
Jones et al., "Dielectrophoretic liquid actuation and nanodroplet formation", J. Appl. Phys., vol. 89, No. 2, Jan. 2001, 1441-1448.
Jun et al., "Valveless Pumping using Traversing Vapor Bubbles in Microchannels", J. Applied Physics, vol. 83, No. 11, Jun. 1998, pp. 5658-5664.
Kajiyama et al., "Enhancement of Thermostability of Firefly Luciferase from Luciola lateralis by a Single Amino Acid Substitution", Biosci. Biotech. Biochem., vol. 58 (6), 1994, 1170-1171.
Kim et al., "Electrowetting on paper for electronic paper display", ACS Applied Materials & Interfaces, vol. 2, Nov. 2010, 3318-3323.
Kim et al., "MEMS Devices Based on the Use of Surface Tension", Proc. Int. Semiconductor Device Research Symposium (ISDRS'99), Charlottesville, VA, Dec. 1999, pp. 481-484.
Kim et al., "Micromachines Driven by Surface Tension", AIAA 99-3800, 30th AIAA Fluid Dynamics Conference, Norfolk, VA, (Invited lecture), Jun. 1999, pp. 1-6.
Kim, "Microelectromechanical Systems (MEMS) at the UCLA Micromanufacturing Lab", Dig. Papers, Int. Microprocesses and Nanotechnology Conf. (MNC'98), Kyungju, Korea, Jul. 1998, pp. 54-55.
Kleinert et al., "Digital microfluidic platform for newborn screening using whole blood in hospital settings for hyperbilirubinemia", Extended abstract from the 2013 APHL Newborn Screening and Genetic Testing Symposium and the International Society for Neonatal Screening, 2013.
Kleinert et al., "Dynamics and stability of oil films during droplet transport by electrowetting", 8th International Meeting on Electrowetting, Athens, Greece, Jun. 21-23, 2012.
Kleinert et al., "Electric Field Assisted Convective Assembly of Colloidal Crystal Coatings", Symposium MM: Evaporative Self Assembly of Polymers, Nanoparticles, and DNA, 2010 MRS Spring Meeting, San Francisco, CA., Apr. 6-8, 2010.
Kleinert et al., "Electric Field-Assisted Convective Assembly of Large-Domain Colloidal Crystals", The 82nd Colloid & Surface Science Symposium, ACS Division of Colloid & Surface Science, North Carolina State University, Raleigh, NC. www.colloids2008.org., Jun. 15-18, 2008.
Kleinert et al., "Evaluation of a Digital Microfluidic Platform for Point of Care Newborn Screening of Hyperbilirubinemia, Congenital Hypothyroidism and G6PD Deficiency in Emerging Programs", Pediatric Academic Societies Annual Meeting, Washington, D.C, Abstract, http://www.abstracts2view.com/pas/., May 4-7, 2013.
Kleinert, "Electric-Field-Assisted Convective Assembly of Colloidal Crystal Coatings", Langmuir, vol. 26(12), May 13, 2010, 10380-10385.

(56) References Cited

OTHER PUBLICATIONS

Kleinert, "Liquid Transport and Colloidal Self Assembly in Thin Wetting Films Driven by Electric Fields", PhD Dissertation, North Carolina State University, 2013.
Koyama et al., "Evaluation of magnetic Beads Agitation Performance Operated by Multi-Layered Flat Coils", Solid-State Sensors, Actuators and Microsystems Conference, 2007. Transducers 2007. International, IEEE, Piscataway, NJ, USA, Jun. 10, 2007, pp. 2385-2388.
Langelier et al., "Acoustically driven programmable liquid motion using resonance cavities", Proceedings of the National Academy of Sciences of the USA, vol. 106, Aug. 2009, 12617-12622.
Lee et al., "Electrowetting and electrowetting-on-dielectric for microscale liquid handling", Sensors and Actuators, vol. 95, 2002, 259-268.
Lee et al., "Liquid Micromotor Driven by Continuous Electrowetting", Proc. IEEE Micro Electro Mechanical Systems Workshop, Heidelberg, Germany, Jan. 1998, pp. 538-543.
Lee et al., "Microactuation by Continuous Electrowetting Phenomenon and Silicon Deep Rie Process", Proc. MEMS (DSC—vol. 66) ASME Int. Mechanical Engineering Congress and Exposition, Anaheim, CA, Nov. 1998, 475-480.
Lee et al., "Theory and Modeling of Continuous Electrowetting Microactuation", Proc. MEMS (MEMS—vol. 1), ASME Int. Mechanical Engineering Congress and Exposition, Nashville, TN, Nov. 1999, pp. 397-403.
Lehmann et al., "Droplet-Based DNA Purification in a Magnetic Lab-on-a-Chip", Angewandte Chemie, vol. 45., 2006, 3062-3067.
Lehmann et al., "Two-dimensional magnetic manipulation of microdroplets on a chip as a platform for bioanalytical applications", Sensors And Actuators B, vol. 117, 2006, 457-463.
Liu et al., "Effect of Non-Ionic Surfactants on the Formation of DNA/Emulsion Complexes and Emulsion-Medicated Gene Transfer", Pharmaceutical Research, vol. 13, No. 11, 1996, 1642-1646.
Locascio et al., "Polymer microfluidic devices", Talanta, vol. 56, Feb. 2002, 267-287.
Luan et al., "Integrated Optical Sensor in a Digital Microfluidic Platform", IEEE Sensors Journal, vol. 8, May 2008, 628-635.
Luk et al., "Pluronic additives: a solution to sticky problems in digital microfluidics", Langmuir: the ACS journal of surfaces and colloids, vol. 24, Jun. 2008, 6382-6389.
Madou et al., "Lab on a CD", Annual Review of Biomedical Engineering, vol. 8, 2006, 601-628.
Malic et al., "Biochip fuctionalization using electrowetting-on-dielectric digital microfluidics for surface plasmon resonance imaging detection of DNA hybridization", Biosensors & Bioelectronics, vol. 24, Mar. 2009, 2218-2224.
Malic et al., "Integration and detection of biochemical assays in digital microfluidic LOC devices", Lab on a chip, vol. 10, Feb. 2010, 418-431.
Malk et al., "EWOD in coplanar electrode configurations", Proceedings of ASME 2010 3rd Joint US-European Fluids Engineering Summer Meeting and 8th International Conference on Nanochannels, Microchannels, and Minichannels, http://asmedl.org/getabs/servlet/GetabsServlet?prog=normal&id=ASMECP002010005450100023900000, Aug. 1-5, 2010.
Manz et al., "Miniaturized Total Chemical Analysis Systems: a Novel Concept for Chemical Sensing", Sensors and Actuators B: Chemical, 1990, 244-248.
Marchand et al., "Organic Synthesis in Soft Wall-Free Microreactors: Real-Time Monitoring of Fluorogenic Reactions", Analytical Chemistry, vol. 80, Jul. 2, 2008, 6051-6055.
Margulies et al., "Genome sequencing in microfabricated high-density picolitre reactors", Nature, vol. 437, 2005, 376-380 and Supplemental Materials.
Mariella et al., "Sample preparation: the weak link in microfluidics-based biodetection", Biomedical Microdevices, vol. 10, Dec. 2008, 777-784.
Mark et al., "Microfluidic lab-on-a chip platforms: requirements, characteristics and applications", Chemical Society reviews, vol. 39, Mar. 2010, 1153-1182.
McDonald et al., "Fabrication of Microfluidic systems in poly (dimethylsiloxane)", Electrophoresis, vol. 21, 2000, 27-40.
Miller et al., "A Digital Microfluidic Approach to Homogeneous Enzyme Assays", Analytical Chemistry, vol. 80, 2008, 1614-1619.
Millington et al., "Applications of tandem mass spectrometry and microfluidics in newborn screening", Southeastern Regional Meeting of the American Chemical Society, Raleigh, North Carolina, 2012.
Millington et al., "Digital microfluidics: a future technology in the newborn screening laboratory", Seminars in Perinatology, vol. 34, Apr. 2010, 163-169.
Millington et al., "Digital Microfluidics: a novel platform for multiplexed detection of LSDs with potential for newborn screening", Association of Public Health Laboratories Annual Conference, San Antonio, TX, Nov. 4, 2008.
Millington et al., "Digital Microfluidics: A Novel Platform For Multiplexing Assays Used In Newborn Screening", Proceedings of the 7th International And Latin American Congress. Oral Presentations. Rev Invest Clin; vol. 61 (Supl. 1), 2009, 21-33.
MIT Tech Review, "Chip mixes droplets faster", MIT Technology Review. Retrieved on Apr. 18, 2008 from:http://www.trnmag.com/Stories/2003/102203/Chip_mixes_droplets_faster_Brief_102203. html., Oct. 2003.
Mohanty et al., "Two Dimensional Micro Gel Electrophoresis Device with Integrated Removeable Capillary Insert (Rci) for Macro-Micro Interface and Post Separation Sample Manipulation", American Electrophoresis Society (AES) Annual Meeting, Nov. 2, 2005.
Moon et al., "Low voltage electrowetting-on-dielectric", Journal of Applied Physics, vol. 92 (7), Oct. 1, 2002, 4080-4087.
Moon, "Electrowetting-on-dielectric microfluidics: Modeling, physics, and MALDI application", Dissertation, University of California, Los Angeles, Aug. 2006.
Moon, "Electrowetting-on-dielectric microfluidics: Modeling, physics, and MALDI application, Electrowetting-on-dielectric microfluidics: Modeling, physics, and MALDI application," University of California, Los Angeles, 2005.
Mousa et al., "Droplet-scale estrogen assays in breast tissue, blood, and serum", Science Translational Medicine, vol. 1, Issue 1, 1ra2, Oct. 7, 2009, 1-6.
Mugele et al., "Electrostatic stabilization of fluid microstructures", Applied Physics Letters, vol. 81(12), Sep. 16, 2002, 2303-2305.
Mugele et al., "Electrowetting: from basics to applications", Journal of Physics: Condensed Matter, vol. 17, Jul. 2005, R705-R774.
Mukhopadhyay et al., "Microfluidic: on the slope of enlightenment", Analytical Chemstry, vol. 81, Jun. 2009, 4169-4173.
Noderer et al., "DNA pyrosequencing using microfluidic chips", NNIN REU Research Accomplishments, 2005, 96-97.
Nuffer et al., "Sample-to-Sequence Analyzer for Human ID Applications", 23rd International Symposium for Human Identification, Nashville, TN. http://www.promega.com/~/media/files/resources/conference%20proceedings/ishi%2023/poster%20abstracts/32%20poster.pdf?la=en, Oct. 16-17, 2012.
Nyren et al., "Enzymatic Method for Continuous Monitoring of Inorganic Pyrophosphate Synthesis", Anal. Biochem., vol. 151, Issue 2, Dec. 1985, 504-509.
Office Action dated May 17, 2013 from related U.S. Appl. No. 12/615,666, dated May 17, 2013.
Office Action from related U.S. Appl. No. 11/639,531, dated Oct. 27, 2010.
Office Action from related U.S. Appl. No. 11/639,531, dated Feb. 17, 2011.
Office Action from related U.S. Appl. No. 11/639,531, dated Mar. 26, 2010.
Office Action from related U.S. Appl. No. 11/639,531, dated Jun. 24, 2010.
Office Action from related U.S. Appl. No. 11/639,531, dated Aug. 19, 2010.
Office Action from related U.S. Appl. No. 11/639,531, dated Sep. 23, 2011.

(56) References Cited

OTHER PUBLICATIONS

Office Action mailed in U.S. Appl. No. 14/978,935, dated Jan. 20, 2016.
Office Action received in related U.S. Appl. No. 14/639,612., dated Jun. 25, 2015.
Office Action received in related U.S. Appl. No. 14/639,612, dated Sep. 30, 2015.
Office Action received in related U.S. Appl. No. 11/639,531, dated Aug. 19, 2010.
Office Action received in related U.S. Appl. No. 11/639,531, dated Jun. 24, 2010.
Office Action received in related U.S. Appl. No. 11/639,531, dated Mar. 26, 2010.
Office Action received in related U.S. Appl. No. 11/639,531, dated Oct. 27, 2010.
Office Action received in related U.S. Appl. No. 11/639,531, dated Sep. 23, 2011.
Office Action received in related U.S. Appl. No. 12/113,385, dated Jul. 11, 2012.
Office Action received in related U.S. Appl. No. 12/615,609, dated Apr. 4, 2012.
Office Action received in related U.S. Appl. No. 12/615,666, dated Feb. 6, 2014.
Office Action received in related U.S. Appl. No. 12/615,666, dated Jun. 14, 2012.
Office Action received in related U.S. Appl. No. 12/615,666, dated Sep. 18, 2013.
Office Action received in related U.S. Appl. No. 13/081,927, dated Apr. 4, 2013.
Office Action received in related U.S. Appl. No. 13/081,927, dated Feb. 22, 2012.
Office Action received in related U.S. Appl. No. 13/081,927, dated Jul. 11, 2011.
Office Action received in related U.S. Appl. No. 14/081,376, dated Dec. 20, 2013.
Office Action received in related U.S. Appl. No. 14/466,193, dated Nov. 20, 2014.
Paik et al., "A digital-microfluidic approach to chip cooling", IEEE Design & Test of Computers, vol. 25, Jul. 2008, 372-381.
Paik et al., "Adaptive Cooling of Integrated Circuits Using Digital Microfluidics", accepted for publication in IEEE Transactions on VLSI Systems, and Artech House, Norwood, MA, 2007.
Paik et al., "Adaptive cooling of integrated circuits using digital microfluidics", IEEE Transactions on VLSI, vol. 16, No. 4, 2008, 432-443.
Paik et al., "Adaptive hot-spot cooling of integrated circuits using digital microfluidics", Proceedings, ASME International Mechanical Engineering Congress and Exposition, Orlando, Florida, USA. IMECE2005-81081, Nov. 5-11, 2005, 1-6.
Paik et al., "Coplanar Digital Microfluidics Using Standard Printed Circuit Board Processes", 9th International Conference on Miniaturized Systems for Chemistry and Life Sciences (MicroTAS), Boston, MA; Poster, Oct. 2005.
Paik et al., "Droplet-Based Hot Spot Cooling Using Topless Digital Microfluidics on a Printed Circuit Board", Int'l Workshops on Thermal Investigations of ICs and Systems (THERMINIC), 2005, 278-83.
Paik et al., "Electrowetting-based droplet mixers for microfluidic systems", Lab on a Chip (LOC), vol. 3. (more mixing videos available, along with the article, at LOC's website), 2003, 28-33.
Paik et al., "Programmable Flow-Through Real Time PCR Using Digital Microfluidics", 11th International Conference on Miniaturized Systems for Chemistry and Life Sciences, Paris, France, Oct. 7-11, 2007, 1559-1561.
Paik et al., "Rapid Droplet Mixers for Digital Microfluidic Systems", Masters Thesis, Duke Graduate School., 2002, 1-82.
Paik et al., "Rapid droplet mixers for digital microfluidic systems", Lab on a Chip, vol. 3. (More mixing videos available, along with the article, at LOC's website.), 2003, 253-259.
Paik et al., "Thermal effects on Droplet Transport in Digital Microfluids with Application to Chip Cooling Processing for Integrated Microfluidics", International Conference on Thermal, Mechanics, and Thermomechanical Phenomena in Electronic Systems (ITherm), 2004, 649-654.
Paik, "Adaptive Hot-Spot Cooling of Integrated Circuits Using Digital Microfluidics", Dissertation, Dept. of Electrical and Computer Engineering, Duke University, Apr. 25, 2006, 1-188.
Pamme, "Magnetism and microfluidics", Lab on a Chip (LOC), vol. 6., 2006, 24-38.
Pamula et al., "A droplet-based lab-on-a-chip for colorimetric detection of nitroaromatic explosives", Proceedings of Micro Electro Mechanical Systems, 2005, 722-725.
Pamula et al., "Cooling of integrated circuits using droplet-based microfluidics", Proc. ACM Great Lakes Symposium on VLSI, Apr. 2003, 84-87.
Pamula et al., "Digital microfluidic lab-on-a-chip for protein crystallization", 5th Protein Structure Initiative "Bottlenecks" Workshop, NIH, Bethesda, MD, Apr. 13-14, 2006, I-16.
Pamula et al., "Digital Microfluidic Methods in Diagnosis of Neonatal Biochemical Abnormalities", Developing Safe and Effective Devices and Instruments for Use in the Neonatal Intensive Care for the 21st Century, Pediatric Academic Societies' Annual Meeting, Vancouver, Canada, May 1-4, 2010.
Pamula et al., "Digital Microfluidic Platform for Multiplexing LSD Assays in Newborn Screening", 7th Annual World Symposium, co-presented by Lysosomal Disease Network and NIH, Las Vegas, NV, Feb. 16-18, 2011.
Pamula et al., "Digital Microfluidics Platform for Lab-on-a-chip applications", Duke University Annual Post Doctoral Research Day, 2002.
Pamula et al., "Microfluidic electrowetting-based droplet mixing", IEEE, 2002, 8-10.
Pamula et al., "Microfluidic electrowetting-based droplet mixing", Proceedings, MEMS Conference Berkeley, (in parent U.S. Appl. No. 12/494,927), Aug. 2001, pp. 8-10.
Pamula et al., "Rapid LSD assays on a multiplex digital microfluidic platform for newborn screening", Lysosomal Disease Network World Symposium 2012, San Diego, CA, Feb. 8-19, 2012, 39.
Pamula, "A digital microfluidic platform for multiplexed explosive detection", Chapter 18, Electronics Noses and Sensors for the Detection of Explosives, Eds., J.W. Gardner and J. Yinon, Kluwer Academic Publishers, 2004.
Pamula, "Digital microfluidic lab-on-a-chip for multiplexing tests in newborn screening", Newborn Screening Summit: Envisioning a Future for Newborn Screening, Bethesda, MD, Dec. 7, 2009.
Pamula, "Digital Microfluidics for Lab-on-a-Chip Applications", "Emerging CAD Challenges for Biochip Design" Workshop, Conference on Design, Automation, and Test in Europe, Munich, Germany, Advance Programme, 2006, pp. 85-87.
Pamula, "Sample Preparation and Processing using Magnetic Beads on a Digital Microfluidic Platform", Cambridge Healthtech Institute's Genomic Tools & Technologies Summit, San Francisco, CA, Jun. 9-10, 2009.
Pamula, "Sample-to-sequence-molecular diagnostics on a digital microfluidic Tab on a chip", Pre-conference workshops, 4th International Conference on Birth Defects and Disabilities in the Developing World, New Dehli, India, Oct. 4, 2009.
Panchapakesan, "Droplet Feedback Mechanisms on a Digital Microfluidic Platform and Development of Hyperbilirubinemia Panel", PhD Dissertation, University at Buffalo, State University of New York, Jan. 9, 2013.
Park et al., "Single-sided continuous optoelectrowetting (SCOEW) droplet manipulation with light patterns", Lab on a chip, vol. 10, Jul. 2010, 1655-1661.
Patch, "Chip juggles droplets", Technology Research News, Retrieved on Apr. 18, 2008 from:http://www.trnmag.com/Stories/2002/090402/Chip_juggles_droplets_090402.html, Sep. 4-11, 2002.
PCT International Preliminary Report on Patentability for PCT/US2007/011298 dated Mar. 10, 2009, dated Mar. 10, 2009.
PCT International Preliminary Report on Patentability for PCT/US2007/009379 dated Oct. 22, 2008, dated Oct. 22, 2008.

(56) References Cited

OTHER PUBLICATIONS

PCT International Preliminary Report on Patentability for PCT/US2009/059868, dated Apr. 12, 2011.
PCT International Preliminary Report on Patentability for PCT/US2006/047486, dated Aug. 15, 2010.
PCT International Preliminary Report on Patentability for PCT/US2005/030247, dated Feb. 28, 2007.
PCT International Search Report and Written Opinion for PCT/US20071009379, dated Aug. 18, 2008.
PCT International Search Report and Written Opinion for PCT/US20071011298, dated Jun. 25, 2008.
Pinho et al., "Haemopoietic progenitors in the adult mouse omentum: permanent production of B lymphocytes and monocytes", Cell Tissue Res., vol. 319, No. 1, Jan. 2005, 91-102.
Pipper et al., "Clockwork PCR Including Sample Preparation", Angew. Chem. Int. Ed., vol. 47, 2008, 3900-3904.
Poliski, "Making materials fit the future: accommodating relentless technological requirements means researchers must recreate and reconfigure materials, frequently challenging established laws of physics, while keeping an eye on Moore's law", R&D Magazine Conference Handout, Dec. 2001.
Pollack et al., "Applications of Electrowetting-Based Digital Microfluidics in Clinical Diagnostics", Expert Rev. Mol. Diagn., vol. 11(4), 2011, 393-407.
Pollack et al., "Continuous sequencing-by-synthesis-based on a digital microfluidic platform", National Human Genome Research Institute, Advanced DNA Sequencing Technology Development Meeting, Chapel Hill, NC, Mar. 10-11, 2010.
Pollack et al., "Electrowetting-Based Actuation of Droplets for Integrated Microfluidics", Lab on a Chip (LOC), vol. 2, 2002, 96-101.
Pollack et al., "Electrowetting-based actuation of liquid droplets for microfluidic applications", Appl. Phys. Letters, vol. 77, No. 11, Sep. 11, 2000, 1725-1726.
Pollack et al., "Electrowetting-Based Microfluidics for High-Throughput Screening", smallTalk 2001 Conference Program Abstract, San Diego, Aug. 27-31, 2001, 149.
Pollack et al., "Investigation of electrowetting-based microfluidics for real-time PCR applications", Proc. of Utas 2003 7th Int'l Conference on Micro Total Analysis Systems (μTAS), Squaw Valley, CA, Oct. 5-9, 2003, 619-622.
Pollack, "Electrowetting-based Microactuation of Droplets for Digital Microfluidics", PhD Thesis, Department of Electrical and Computer Engineering, Duke University, 2001.
Pollack, "Lab-on-a-chip platform based digital microfluidics", The 6th International Electrowetting Meeting, Aug. 20-22, 2008, 16.
Pollack, "Sample Preparation Using Digital Microfluidics", Sample Prep 2012, Knowledge Press, Inc., May 3-4, 2012.
Poloski, "Making materials fit the future: accommodating relentless technological requirements means researchers must recreate and reconfigure materials, frequently challenging established laws of physics, while keeping an eye on Moore's law", R&D Magazine Confer, Dec. 2001.
Popular Mechanics, "Laboratory on a Chip", Popular Mechanics—Tech Watch, Retrieved on Apr. 18, 2008 from:http://www.ee.duke.edu/research/microfluidics/images/PopMechArticle.JPG, Mar. 2002, 25.
Poulos et al., "Electrowetting on dielectric-based microfluidics for integrated lipid bilayer formation and measurement", Applied Physics Letters, vol. 95, 2009, 013706.
Punnamaraju et al., "Voltage Control of Droplet Interface Bilayer Lipid Membrane Dimensions", Langmuir The ACS Journal of Surfaces and Colloids, vol. 27, Issue 2, 2011, published online, Dec. 10, 2010, 618-626.
Punnamaraju, "Voltage and Photo Induced Effects in Droplet-Interface-Bilayer Lipid", PhD Thesis, University of Cincinnati, 2011.
Raccurt et al., "On the influence of surfactants in electrowetting systems", J. Micromech. Microeng., vol. 17, 2007, 2217-2223.
Raj et al., "Composite Dielectrics and Surfactants for Low Voltage Electrowetting Devices", University/Government/Industry Micro/Nano Symposium, vol. 17, Jul. 13-16, 2008, 187-190.
Ren et al., "Automated electrowetting-based droplet dispensing with good reproducibility", Proc. Micro Total Analysis Systems (μTAS), 7th Int. Conf.on Miniaturized Chem and Biochem Analysis Systems, Squaw Valley, CA, Oct. 5-9, 2003, 993-996.
Ren et al., "Automated on-chip droplet dispensing with volume control by electro-wetting actuation and capacitance metering", Sensors and Actuators B: Chemical, vol. 98, Mar. 2004, 319-327.
Ren et al., "Design and testing of an interpolating mixing architecture for electrowetting-based droplet-on-chip chemical dilution", Transducers, 12th International Conference on Solid-State Sensors, Actuators and Microsystems, 2003, 619-622.
Ren et al., "Dynamics of electro-wetting droplet transport", Sensors and Actuators B (Chemical), vol. B87, No. 1, Nov. 15, 2002, 201-206.
Ren et al., "Micro/Nano Liter Droplet Formation and Dispensing by Capacitance Metering and Electrowetting Actuation", IEEE-NANO, 2002, 369-372.
Rival et al., "EWOD Digital Microfluidic Device for Single Cells Sample Preparation and Gene Expression Analysis", Lab Automation 2010, Palm Springs Convention Center, Palm Springs, CA, USA; Abstract in Proceedings, Poster distributed at conference, Jan. 23-27, 2010.
Rival et al., "Expression de gènes de quelques cellules sur puce EWOD/Gene expression of few cells on EWOD chip", iRTSV, http://www-dsv.cea.fr/var/plain/storage/original/media/File/iRTSV/thema_08(2).pdf (english translation), Winter 2009-2010.
Rival et al., "New insight on droplet dynamics under electrowetting actuation and design tools for speeding up product development", 8th Electrowetting Workshop, Athens, Greece. Abstract, 2012.
Rival et al., "Towards single cells gene expression on EWOD lab on chip", ESONN, Grenoble, France, abstract in proceedings, Aug. 2008.
Rival et al., "Towards single cells gene expression preparation and analysis on ewod lab on chip", Nanobio Europe 2009, Poster distributed at conference, Jun. 16-18, 2009.
Rival et al., "Towards single cells gene expression preparation and analysis on ewod lab on chip", Lab On Chip Europe 2009 poster distributed at Conference, May 19-20, 2009.
Rival, et al., "Towards Single Cells Gene Expression on EWOD Lab On Chip", ESONN, Grenoble, France; Poster presented, Aug. 26, 2008.
Rouse et al., "Digital microfluidics: a novel platform for multiplexing assays used in newborn screening", Poster 47, 41st AACC's Annual Oak Ridge Conference Abstracts, Clinical Chemistry, vol. 55, 2009, 1891.
Roux et al., "3D droplet displacement in microfluidic systems by electrostatic actuation", Sensors and Actuators A, vol. 134, Issue 2, Mar. 15, 2007, 486-493.
Russom et al., "Pyrosequencing in a Microfluidic Flow-Through Device", Anal. Chem. vol. 77, 2005, 7505-7511.
Sandahl et al., "Automated Multianalyte Screening for Classification of Forensic Samples", 23rd International Symposium for Human Identification, Nashville, TN. http://www.promega.com/~/media/files/resources/conference%20proceedings/ishi%2023/poster%20abstracts/31%20poster.pdf?la=en, Oct. 16-17, 2012.
Schell et al., "Evaluation of a Digital Microfluidic real-time PCR Platform to detect DNA of Candida albicans", Eur. J. Clin Microbiol Infect Dis, Published on-line DOI 10.1007/s10096-012-15616, Feb. 2012.
Schwartz et al., "Dielectrophoretic approaches to sample preparation and analysis", The University of Texas, Dissertation, Dec. 2001.
Schwartz et al., "Droplet-based chemistry on programmable microchip", Lab on a Chip, vol. 4, No. 1, 2002, 11-17.
Shah et al., "EWOD-driven droplet microfluidic device integrated with optoelectronic tweezers as an automated platform for cellular isolation and analysis", Lab on a Chip, vol. 9, Jun. 2009, 1732-1739.
Shah et al., "Meniscus-assisted magnetic bead trappings on EWOD-based digital microfluidics for specific protein localization", Transducers and Eurosensors, Jun. 2007.

(56) References Cited

OTHER PUBLICATIONS

Sherman et al., "Flow Control by Using High-Aspect-Ratio, In-Plane Microactuators", Sensors and Actuators, vol. 73, 1999, pp. 169-175.
Sherman et al., "In-Plane Microactuator for Fluid Control Application", Proc. IEEE Micro Electro Mechanical Systems Workshop, Heidelberg, Germany, Jan. 1998, pp. 454-459.
Shi et al., "Evaluation of stability of fluorometric reagent kits for screening of Lysosomal Storage Disorders", APHL Newborn Screening and Genetic Testing Symposium, San Diego, 2011.
Shikida et al., "Using wetability and interfacial tension to handle droplets of magnetic beads in a micro-chemical-analysis system", Sensors and Actuators, vol. 113, 2006, 563-569.
Shin et al., "Machine vision for digital microfluidics", Review of Scientific Instruments, vol. 81, 2010, 014302.
Sista et al., "96-Immunoassay Digital Microfluidic Multiwell Plate", Proc. µTAS, Oct. 12-16, 2008.
Sista et al., "Development of a digital microfluidic platform for point of care testing", Lab on a chip, vol. 8, Dec. 2008, First published as an Advance Article on the web, Nov. 5, 2008, 2091-2104.
Sista et al., "Development of digital microfluidic assays for galactosemia and biotinidase deficiency in newborn dried blood spot samples", 2013 APHL Newborn Screening and Genetic Testing Symposium and the International Society for Neonatal Screening, Atlanta, GA. Poster presented, abstract in conference proceedings, May 5-10, 2013.
Sista et al., "Digital Microfluidic Platform for Multiplexing Enzyme Assays Implications for Lysosomal Storage Disease Screening in Newborns", Clinical Chemistry, vol. 57, Aug. 22, 2011, 1444-51.
Sista et al., "Digital Microfluidic platform for multiplexing LSD assays in newborn screening", APHL Newborn Screening and Genetic Testing Symposium, Orlando, May 3-6, 2010.
Sista et al., "Digital Microfluidic Platform to Consolidate Enzymatic Assays on Dried Blood Spot Samples for Rapid Newborn Screening", 2013 Canadian Newborn and Child Screening Symposium, Ottawa, Canada, Poster, Apr. 11-12, 2013.
Sista et al., "Enzymatic assays on whole blood for lysosomal storage diseases using a digital microfluidic platform", 2013 American Association for Clinical Chemistry (AACC) Annual Meeting, Houston, TX, Abstract accepted for poster presentation, Jul. 28-Aug. 1, 2013.
Sista et al., "Heterogeneous immunoassays using magnetic beads on a digital microfluidic platform", Lab on a Chip, vol. 8, Dec. 2008, First published as an Advance Article on the web, Oct. 14, 2008, 2188-2196.
Sista et al., "Multiplex digital microfluidic platform for newborn screening of Tysosomal storage disorders", 2013 Pediatric Academic Societies Annual Meeting PAS (Pediatric Academic Society), Washington, D.C., poster presented, abstract published online http://www.abstracts2view.com/pas/, May 4-7, 2013.
Sista et al., "Multiplex Digital Microfluidic Platform for Rapid Newborn Screening of Lysosomal Storage Disorders", ACMG Annual Meeting, Charlotte, NC, 2012.
Sista et al., "Multiplex Newborn Screening for Pompe, Fabry, Hunter, Gaucher, and Hurler Diseases Using a Digital Microfluidic Platform", Clinica Chimica Acta, vol. 424. available on line http://dx.doi.org/10.1016/j.cca.2013.05.001, May 7, 2013, 12-18.
Sista et al., "Performance of a digital microfluidic assay for Gaucher and Hurler disorders", APHL Newborn Screening and Genetic Testing Symposium, San Diego, 2011.
Sista et al., "Performance of multiple enzymatic assays on dried blood spot samples for rapid newborn screening using digital microfluidics", 2013 Oak Ridge Conference (AACC), Baltimore, MD, poster presentation, Apr. 18-19, 2013.
Sista et al., "Rapid assays for Gaucher and Hurler diseases in dried blood spots using digital microfluidics", Molecular Genetics and Metabolism. vol. 109. Available online http://dx.doi.org/10.1016/j.ymgme.2013.03.010, 2013, 218-220.

Sista et al., "Rapid, Single-Step Assay for Hunter Syndrome in Dried Blood Spots Using Digital Microfluidics", Clinica Chimica Acta, vol. 412, 2011, 1895-97.
Sista et al., "Spatial multiplexing of immunoassays for small-volume samples", 10th PI Meeting IMAT, Bethesda, 2009.
Sista, "Development of a Digital Microfluidic Lab-on-a-Chip for Automated Immunoassays with Magnetically Responsive Beads", PhD Thesis, Department of Chemical Engineering, Florida State University, 2007.
Squires et al., "Microfluidics:Fluid physics at the nanoliter scale", Reviews of Modern Physics, vol. 77, 2005, 977-1-26.
Srinivasan et al., "3-D imaging of moving droplets for microfluidics using optical coherence tomography", Proc. 7th International Conference on Micro Total Analysis Systems (mTAS), Squaw Valley, CA, Oct. 5-9, 2003, 1303-1306.
Srinivasan et al., "A digital microfluidic biosensor for multianalyte detection", Proc. IEEE 16th Annual Int'l Conf. on Micro Electro Mechanical Systems Conference, 2003, 327-330.
Srinivasan et al., "An integrated digital microfluidic lab-on-a-chip for clinical diagnostics on human physiological fluids", Lab on a Chip, vol. 4, 2004, 310-315.
Srinivasan et al., "Clinical diagnostics on human whole blood, plasma, serum, urine, saliva, sweat and tears on a digital microfluidic platform", Proc. 7th International Conference on Micro Total Analysis Systems (mTAS), Squaw Valley, CA, Oct. 5-9, 2003, 1287-1290.
Srinivasan et al., "Commercializing electrowetting-based digital microfluidics: from the lab to a product", 8th International Meeting on Electrowetting, Athens, Greece, Jun. 21-23, 2012.
Srinivasan et al., "Digital Microfluidic Lab-on-a-Chip for Protein Crystallization", The 82nd ACS Colloid and Surface Science Symposium, Abstract Book, 2008, 269-321.
Srinivasan et al., "Digital Microfluidics: a novel platform for multiplexed detection of lysosomal storage diseases for newborn screening", AACC Oak Ridge Conference Abstracts, Clinical Chemistry, vol. 54, Apr. 17-18, 2008, 1934.
Srinivasan et al., "Droplet-based microfluidic lab-on-a-chip for glucose detection", Analytica Chimica Acta, vol. 507, No. 1, 2004, 145-150.
Srinivasan et al., "Electrowetting", Chapter 5, Methods in Bioengineering: Biomicrofabrication and Biomicrofluidics, Ed. J.D. Zahn, ISBN: 9781596934009, Artech House Publishers, 2010.
Srinivasan et al., "Feasibility of a point of care newborn screening platform for hyperbilirubinemia", APHL Newborn Screening and Genetic Testing Symposium, San Diego, 2011.
Srinivasan et al., "Low cost digital microfluidic platform for protein crystallization", Enabling Technologies for Structural Biology, NIGMS Workshop, Bethesda, MD., Mar. 4-6, 2009, J-23.
Srinivasan et al., "Protein Stamping for MALDI Mass Spectrometry Using an Electrowetting-based Microfluidic Platform", Lab-on-a-Chip: Platforms, Devices, and Applications, Conf. 5591, SPIE Optics East, Philadelphia, Oct. 25-28, 2004.
Srinivasan et al., "Scalable Macromodels for Microelectromechanical Systems", Technical Proc. 2001 Int. Conf. on Modeling and Simulation of Microsystems, 2001, 72-75.
Srinivasan, "A Digital Microfluidic Lab-on-a-Chip for Clinical Diagnostic Applications", Dissertation submitted in partial fulfillment of the requirements for the degree of Doctor of Philosophy in the Department of Electrical and Computer Engineering in the Graduate School of Duke University, 2005, 136 pages.
Su et al., "Testing of droplet-based microelectrofluidic systems", Proc. IEEE International Test Conference, 2003, 1192-1200.
Su et al., "Yield Enhancement of Digital Microfluidics-Based Biochips Using Space Redundancy and Local Reconfiguration", Proc. Design, Automation and Test in Europe Conf., IEEE, 2005, 1196-1201.
Sudarsan et al., "Printed circuit technology for fabrication of plastic based microfluidic devices", Analytical Chemistry vol. 76, No. 11, Jun. 1, 2004, Previously published on-line, May 2004, 3229-3235.
Taira et al., "Immobilization of Single-Stranded DNA by Self-Assembled Polymer on Gold Substrate for a DNA Chip", Biotechnology and Bioengineering, vol. 89, Issue 7, Mar. 30, 2005, 835-838.

(56) References Cited

OTHER PUBLICATIONS

Taniguchi et al., "Chemical reactions in microdroplets by electrostatic manipulation of droplets in liquid media", Lab on a Chip, vol. 2, No. 2, 2002, 19-23.
Teh et al., "Droplet microfluidics", Lab on a chip, vol. 8, Feb. 2008, 198-220.
Terry et al., "A Gas Chromatographic Air Analyzer Fabricated on a Silicon Wafer", IEEE Transactions on Electron Devices, vol. ED-26, 1979, 1880-1886.
Thwar et al., "DNA sequencing using digital microfluidics", Poster 42, 41st AACC's Annual Oak Ridge Conference Abstracts, Clinical Chemistry, vol. 55, No. 10, Oct. 2009, 1891.
Tolun et al., "A Novel Fluorometric Enzyme Analysis Method for Hunter Syndrome Using Dried Blood Spots", Mol. Genet. Metab., 105, Issue 3, 2012; doi:10.1016/j.ymgme.2011.12.011, Epub, Dec. 21, 2011, 519-521.
Tolun et al., "Dried blood spot based enzyme assays for lysosomal storage disorders", 2011 Tokyo Meeting on Lysosomal Storage Disease Screening, Tokyo, Aug. 5, 2011.
Torkkeli, "Droplet microfluidics on a planar surface", Doctoral Dissertation, Department of Electrical Engineering, Helsinki University of Technology, Oct. 3, 2003.
Tsuchiya et al., "On-chip polymerase chain reaction microdevice employing a magnetic droplet-manipulation system", Sensors and Actuators B, vol. 130, Oct. 18, 2007, 583-588.
Tuckerman et al., "High-Performance Heat Sinking for VLSI", IEEE Electron Device Letters, 1981, 126-129.
Verpoorte, "Beads and chips: new recipes for analysis", Lab on a Chip (LOC), vol. 3., 2003, 60N-68N.
Wang et al., "Comparison of enzyme activities for Pompe, Fabry, and Gaucher diseases on CDC's Quality Control spots between microplate fluorometry, mass spectrometry, and digital microfluidic fluorometry", APHL Newborn Screening and Genetic Testing Symposium, San Diego, 2011.
Wang et al., "Droplet-based micro oscillating-flow PCR chip", J. Micromechanics and Microengineering, vol. 15, 2005, 1369-1377.
Wang et al., "Efficient in-droplet separation of magnetic particles for digital microfluidics", Journal of Micromechanics and Microengineering, vol. 17, 2007, 2148-2156.
Washizu, "Electrostatic Actuation of Liquid Droplets for Micro-Reactor Applications", IEEE Industry Applications Society Annual Meeting, Oct. 5-9, 1997, 1867-1873.
Weaver, "Application of Magnetic Microspheres for Pyrosequencing on a Digital Microfluidic Platform", Department of Electrical and Computer Engineering, Duke University, Web publication, Aug. 29, 2005.
Weber et al., "Specific Blood Purification By Means of Antibody-Conjugated Magnetic Microspheres", Centre for Biomedical Technology, Austria, Scientific and Clinical Applications of Magnetic Carriers, 1997.
Wego et al., "Fluidic microsystems based on printed circuit board technology", Journal of Micromechanics and Microengineering, vol. 11, No. 5, Sep. 2001, 528-531.
Welch et al., "Picoliter DNA sequencing chemistry on an electrowetting-based digital microfluidic platform", Biotechnology Journal, vol. 6, Feb. 2011, 165-176.
Welters et al., "Fast Electrically Switchable Capillary Effects", Langmuir, vol. 14, Mar. 1998, 1535-1538.
Wheeler et al., "Electrowetting-Based Microfluidics for Analysis of Peptides and Proteins by Matrix-Assisted Laser Desportion/ Ionization Mass Spectrometry", Anal. Chem. 76, 2004, 4833-4838.
Wheeler et al., "Electrowetting-on-dielectric for analysis of peptides and proteins by matrix assisted laser desorption / ionization mass spectrometry", Solid-State Sensor, Actuator and Microsystems Workshop publication, Jun. 6-10, 2004, 402-403.
Wheeler, "Putting Electrowetting to Work", Science, vol. 322, No. 5901, Oct. 24, 2008, 539-540.
Whitesides, "The origins and future of microfluidics", Nature, vol. 442, 2006, 368-373.

Wulff-Burchfield et al., "Microfluidic platform versus conventional real-time polymerase chain reaction for the detection of Mycoplasma pneumoniae in respiratory specimens", Diagnostic Microbiology and Infectious Disease, vol. 67, 2010, 22-29.
Xu et al., "A Cross-Referencing-Based Droplet Manipulation Method for High-Throughput and Pin-Constrained Digital Microfluidic Arrays", Proceedings of conference on Design, Automation and Test in Europe, Apr. 2007.
Xu et al., "Automated Design of Pin-Constrained Digital Microfluidic Biochips Under Droplet-Interference Constraints", ACM Journal on Emerging Technologies is Computing Systems, vol. 3(3), 2007, 14:1-14:23.
Xu et al., "Automated solution preparation on a digital microfluidic lab-on-chip", PSI Bottlenecks Workshop, 2008.
Xu et al., "Automated, Accurate and Inexpensive Solution-Preparation on a Digital Microfluidic Biochip", Proc. IEEE Biomedical Circuits and Systems Conference (BioCAS), 2008, 301-304.
Xu et al., "Defect-Aware Synthesis of Droplet-Based Microfluidic Biochips", IEEE, 20th International Conference on VLSI Design, 2007.
Xu et al., "Defect-Tolerant Design and Optimization of a Digital Microfluidic Biochip for Protein Crystallization", IEEE Transactions on Computer Aided Design, vol. 29, No. 4, Apr. 2010, 552-565.
Xu et al., "Design and Optimization of a Digital Microfluidic Biochip for Protein Crystallization", Proc. IEEE/ACM International Conference on Computer-Aided Design (ICCAD), Nov. 2008, 297-301.
Xu et al., "Digital Microfluidic Biochip Design for Protein Crystallization", IEEE-NIH Life Science Systems and Applications Workshop, LISA, Bethesda, MD, Nov. 8-9, 2007, 140-143.
Xu et al., "Droplet-Trace-Based Array Partitioning and a Pin Assignment Algorithm for the Automated Design of Digital Microfluidic Biochips", Codes, 2006, 112-117.
Xu et al., "Integrated Droplet Routing in the Synthesis of Microfluidic Biochips", IEEE, 2007, 948-953.
Xu et al., "Parallel Scan-Like Test and Multiple-Defect Diagnosis for Digital Microfluidic Biochips", IEEE Transactions on Biomedical Circuits and Systems, vol. 1(2), Jun. 2007, 148-158.
Xu et al., "Parallel Scan-Like Testing and Fault Diagnosis Techniques for Digital Microfluidic Biochips", Proceedings of the 12th IEEE European Test Symposium (ETS), Freiburg, Germany, May 20-24, 2007, 63-68.
Yager et al., "Microfluidic diagnostic technologies for global public health", Nature, vol. 442, 2006, 412-418.
Yang et al., "Manipulation of droplets in microfluidic systems", Trends in Analytical Chemistry, vol. 29, Feb. 2010, 141-157.
Yao et al., "Spot Cooling Using Thermoelectric Microcooler", Proc. 18th Int. Thermoelectric Conf, Baltimore, MD, Aug. 1999, pp. 256-259.
Ybarra, "Independent Study and Undergraduate Research [Online]", Retrieved from the Internet: URL:http://www.ece.duke.edu/undergrads/independent_study.php [retrieved on Jul. 24, 2008].
Yi et al., "Channel-to-droplet extractions for on-chip sample preparation", Solid-State Sensor, Actuators and Microsystems Workshop (Hilton Head '06), Hilton Head Island, SC, Jun. 2006, 128-131.
Yi et al., "Characterization of electrowetting actuation addressable single-side coplanar electrodes", J. Micromech. Microeng. vol. 16, Oct. 16, 2006, 2053-2059.
Yi et al., "EWOD Actuation with Electrode-Free Cover Plate", Digest of Tech. papers,13th International Conference on Solid-State Sensors, Actuators and Microsystems (Transducers '05), Seoul, Korea, Jun. 5-9, 2005, 89-92.
Yi et al., "Geometric surface modification of nozzles for complete transfer of liquid drops", Solid-State Sensor, Actuator and Microsystems Workshop, Hilton Head Island, South Carolina, Jun. 6-10, 2004, 164-167.
Yi et al., "Microfluidics technology for manipulation and analysis of biological cells", Analytica Chimica Acta, vol. 560, 2006, 1-23.
Yi et al., "Soft Printing of Droplets Digitized by Electrowetting", Transducers 12th Int'l Conf. on Solid State Sensors, Actuators and Microsystems, Boston, Jun. 8-12, 2003, 1804-1807.

(56) References Cited

OTHER PUBLICATIONS

Yi et al., "Soft Printing of Droplets Pre-Metered by Electrowetting", Sensors and Actuators A: Physical, vol. 114, Jan. 2004, 347-354.
Yi, "Soft Printing of Biofluids for Micro-arrays: Concept, Principle, Fabrication, and Demonstration", Ph.D. dissertation, UCLA, 2004.
Yi, "Soft Printing of biological liquids for microarrays: concept, principle, fabrication, and demonstration", A dissertation submitted in partial satisfaction of the requirements for the degree Doctor of Philosophy in Mechanical Engineering, 2004, 113 pgs.
Yoon et al., "Preventing Biomolecular Absorption in Electrowetting-Based Biofluidic Chips", Analytical Chem. vol. 75,, 2003, 5097-5102.
Zeng et al., "Actuation and Control of Droplets by Using Electrowetting-on-Dielectrc", Chin. Phys. Lett. vol. 21, No. 9, 2004, 1851-1854.
Zhang et al., "Behavioral modeling and performance evaluation of microelectrofluidics-based PCR systems using SystemC", IEEE Transactions on Computer-Aided Design of Integrated Circuits & Systems, vol. 23 (6), Jun. 2, 2004, 843-858.
Zhang, "An Integrated Hierarchical Modeling and Simulation Approach for Microelectrofluidic Systems", Dissertation, Department of Electrical and Computer Engineering, Duke University, 2001, 171-205.
Zhao et al., "Droplet Manipulation and Microparticle Sampling on Perforated Microfilter Membranes", J. Micromech. Microeng., vol. 18, 2008, 1-11.
Zhao et al., "In-droplet particle separation by travelling wave dielectrophoresis (twDEP) and EWOD", Solid-State Sensor, Actuators and Microsystems Workshop (Hilton Head '06), Hilton Head Island, SC, Jun. 2006, 181-184.
Zhao et al., "Micro air bubble manipulation by electrowetting on dielectric (EWOD): transporting, splitting, merging and eliminating of bubbles", Lab on a chip, vol. 7, 2007, First published as an Advance Article on the web, Dec. 4, 2006, 273-280.
Zhao et al., "Microparticle Concentration and Separation by Traveling-Wave Dielectrophoresis (twDEP) for Digital Microfluidics", J. Microelectromechanical Systems, vol. 16, No. 6, Dec. 2007, 1472-1481.
Zhao et al., "Optimization Techniques for the Synchronization of Concurrent Fluidic Operations in Pin-Constrained Digital Microfluidic Biochips", IEEE Transactions on Very Large Scale Integration (VLSI) Systems, vol. 20, No. 6, Jun. 2012, 1132-1145.
Zhao et al., "Synchronization of Concurrently-Implemented Fluidic Operations in Pin-Constrained Digital Microfluidic Biochips", VLSI Design, (Best Paper Award), 2010.
PCT International Search Report and Written Opinion for PCT/US2017/024451, dated Jul. 5, 2017.
Abstract from National Institutes of Health Grant No. 2R44DK066956-02 titled "Nanoliter Lab-on-a-Chip for Blood Diagnostics", accessed online and printed Feb. 24, 2016.
Abstract from National Institutes of Health Grant No. 1R43CA114993-01A2, titled "Nanoliter Lab-on-a-Chip for Rapid Parallel Immunoassays", accessed online and printed Oct. 2, 2015.
Abstract from National Institutes of Health Grant No. 1R43GM072155-01, titled "Nanoliter Lab-on-a-Chip for Protein Crystallization", accessed online and printed Dec. 8, 2015.
Abstract from National Institutes of Health Grant No. HG003076, titled "High Fidelity Genomic Cloning and Amplification", accessed online and printed May 16, 2023.

\* cited by examiner

MANIPULATION OF BEADS IN DROPLETS AND METHODS FOR MANIPULATING DROPLETS

RELATED APPLICATIONS

This application is a continuation of and claims priority to U.S. patent application Ser. No. 16/191,270, entitled "Manipulation of Beads in Droplets and Methods for Manipulating Droplets," filed Nov. 14, 2018, which is a divisional of and claims priority to U.S. patent application Ser. No. 15/266,693, entitled "Manipulation of Beads in Droplets and Methods for Manipulating Droplets," filed Sep. 15, 2016, now U.S. Pat. No. 10,139,403, issued Nov. 27, 2018, which is a continuation of and claims priority to U.S. patent application Ser. No. 14/978,935, entitled "Manipulation of Beads in Droplets and Methods for Manipulating Droplets," filed Dec. 22, 2015, now U.S. Pat. No. 9,494,498, issued Nov. 15, 2016, the application of which is a continuation of and claims priority to U.S. patent application Ser. No. 14/746,276, entitled "Manipulation of Beads in Droplets and Methods for Manipulating Droplets," filed Jun. 22, 2015, now U.S. Pat. No. 9,377,455, issued Jun. 28, 2016, the application of which is a continuation of and claims priority to U.S. patent application Ser. No. 14/308,110, entitled "Bead Incubation and Washing on a Droplet Actuator" filed Jun. 18, 2014, now U.S. Pat. No. 9,086,345, issued Jul. 21, 2015, the application of which is a divisional of and claims priority to U.S. patent application Ser. No. 12/761,066, entitled "Manipulation of Beads in Droplets and Methods for Manipulating Droplets," filed Apr. 15, 2010, now U.S. Pat. No. 8,809,068, issued Aug. 19, 2014, the application of which is A) a continuation of and claims priority to International Patent Application No. PCT/US2008/080264, entitled "Manipulation of Beads in Droplets," filed Oct. 17, 2008, which claims priority to provisional U.S. patent application Ser. No. 60/980,782, entitled "Manipulation of Beads in Droplets," filed on Oct. 17, 2007; and B) a continuation-in-part of and claims priority to U.S. patent application Ser. No. 11/639,531, entitled "Droplet-Based Washing," filed Dec. 15, 2006, now U.S. Pat. No. 8,613,889, issued Dec. 24, 2013, which claims priority to provisional U.S. Patent Application Nos. 60/745,058, entitled "Filler Fluids for Droplet-Based Microfluidics" filed on Apr. 18, 2006; 60/745,039, entitled "Apparatus and Methods for Droplet-Based Blood Chemistry," filed on Apr. 18, 2006; 60/745,043, entitled "Apparatus and Methods for Droplet-Based PCR," filed on Apr. 18, 2006; 60/745,059, entitled "Apparatus and Methods for Droplet-Based Immunoassay," filed on Apr. 18, 2006; 60/745,914, entitled "Apparatus and Method for Manipulating Droplets with a Predetermined Number of Cells" filed on Apr. 28, 2006; 60/745,950, entitled "Apparatus and Methods of Sample Preparation for a Droplet Microactuator," filed on Apr. 28, 2006; 60/746,797 entitled "Portable Analyzer Using Droplet-Based Microfluidics," filed on May 9, 2006; 60/746,801, entitled "Apparatus and Methods for Droplet-Based Immuno-PCR," filed on May 9, 2006; 60/806,412, entitled "Systems and Methods for Droplet Microactuator Operations," filed on Jun. 30, 2006; and 60/807,104, entitled "Method and Apparatus for Droplet-Based Nucleic Acid Amplification," filed on Jul. 12, 2006; the disclosure of each of the aforementioned patents and patent applications are incorporated herein by reference in their entirety.

GOVERNMENT INTEREST

This invention was made with government support under DK066956-02 and CA114993-01A2 awarded by the National Institutes of Health. The government has certain rights in the invention.

BACKGROUND

Droplet actuators are used to conduct a wide variety of droplet operations. A droplet actuator typically includes two substrates separated by a gap. The substrates include electrodes for conducting droplet operations. The space is typically filled with a filler fluid that is immiscible with the fluid that is to be manipulated on the droplet actuator. The formation and movement of droplets is controlled by electrodes for conducting a variety of droplet operations, such as droplet transport and droplet dispensing. There is a need for improvements to droplet actuators that facilitate handling of droplets with beads.

SUMMARY OF THE INVENTION

The invention provides a method of dispersing or circulating magnetically responsive beads within a droplet in a droplet actuator. The invention, in one embodiment, makes use of a droplet actuator with a plurality of droplet operations electrodes configured to transport the droplet, and a magnet field present at a portion of the plurality of droplet operations electrodes. A bead bead-containing droplet is provided on the droplet actuator in the presence of the uniform magnetic field. Beads are circulated in the droplet during incubation by conducting droplet operations on the droplet within a uniform region of the magnetic field. Other aspects of the invention will be apparent from the ensuing description of the invention.

Definitions

As used herein, the following terms have the meanings indicated.

"Activate" with reference to one or more electrodes means effecting a change in the electrical state of the one or more electrodes which results in a droplet operation.

"Bead," with respect to beads on a droplet actuator, means any bead or particle that is capable of interacting with a droplet on or in proximity with a droplet actuator. Beads may be any of a wide variety of shapes, such as spherical, generally spherical, egg shaped, disc shaped, cubical and other three dimensional shapes. The bead may, for example, be capable of being transported in a droplet on a droplet actuator or otherwise configured with respect to a droplet actuator in a manner which permits a droplet on the droplet actuator to be brought into contact with the bead, on the droplet actuator and/or off the droplet actuator. Beads may be manufactured using a wide variety of materials, including for example, resins, and polymers. The beads may be any suitable size, including for example, microbeads, microparticles, nanobeads and nanoparticles. In some cases, beads are magnetically responsive; in other cases beads are not significantly magnetically responsive. For magnetically responsive beads, the magnetically responsive material may constitute substantially all of a bead or one component only of a bead. The remainder of the bead may include, among other things, polymeric material, coatings, and moieties which permit attachment of an assay reagent. Examples of suitable magnetically responsive beads are described in U.S.

Patent Publication No. 2005-0260686, entitled, "Multiplex flow assays preferably with magnetic particles as solid phase," published on Nov. 24, 2005, the entire disclosure of which is incorporated herein by reference for its teaching concerning magnetically responsive materials and beads. The fluids may include one or more magnetically responsive and/or non-magnetically responsive beads. Examples of droplet actuator techniques for immobilizing magnetically responsive beads and/or non-magnetically responsive beads and/or conducting droplet operations protocols using beads are described in U.S. patent application Ser. No. 11/639,566, entitled "Droplet-Based Particle Sorting," filed on Dec. 15, 2006; U.S. Patent Application No. 61/039,183, entitled "Multiplexing Bead Detection in a Single Droplet," filed on Mar. 25, 2008; U.S. patent application Ser. No. 61/047,789, entitled "Droplet Actuator Devices and Droplet Operations Using Beads," filed on Apr. 25, 2008; U.S. patent application Ser. No. 61/086,183, entitled "Droplet Actuator Devices and Methods for Manipulating Beads," filed on Aug. 5, 2008; International Patent Application No. PCT/US2008/053545, entitled "Droplet Actuator Devices and Methods Employing Magnetically responsive beads," filed on Feb. 11, 2008; International Patent Application No. PCT/US2008/058018, entitled "Bead-based Multiplexed Analytical Methods and Instrumentation," filed on Mar. 24, 2008; International Patent Application No. PCT/US2008/058047, "Bead Sorting on a Droplet Actuator," filed on Mar. 23, 2008; and International Patent Application No. PCT/US2006/047486, entitled "Droplet-based Biochemistry," filed on Dec. 11, 2006; the entire disclosures of which are incorporated herein by reference.

"Droplet" means a volume of liquid on a droplet actuator that is at least partially bounded by filler fluid. For example, a droplet may be completely surrounded by filler fluid or may be bounded by filler fluid and one or more surfaces of the droplet actuator. Droplets may, for example, be aqueous or non-aqueous or may be mixtures or emulsions including aqueous and non-aqueous components. Droplets may take a wide variety of shapes; nonlimiting examples include generally disc shaped, slug shaped, truncated sphere, ellipsoid, spherical, partially compressed sphere, hemispherical, ovoid, cylindrical, and various shapes formed during droplet operations, such as merging or splitting or formed as a result of contact of such shapes with one or more surfaces of a droplet actuator.

"Droplet Actuator" means a device for manipulating droplets. For examples of droplets, see U.S. Pat. No. 6,911,132, entitled "Apparatus for Manipulating Droplets by Electrowetting-Based Techniques," issued on Jun. 28, 2005 to Pamula et al.; U.S. patent application Ser. No. 11/343,284, entitled "Apparatuses and Methods for Manipulating Droplets on a Printed Circuit Board," filed on filed on Jan. 30, 2006; U.S. Pat. No. 6,773,566, entitled "Electrostatic Actuators for Microfluidics and Methods for Using Same," issued on Aug. 10, 2004 and U.S. Pat. No. 6,565,727, entitled "Actuators for Microfluidics Without Moving Parts," issued on Jan. 24, 2000, both to Shenderov et al.; Pollack et al., International Patent Application No. PCT/US2006/047486, entitled "Droplet-Based Biochemistry," filed on Dec. 11, 2006, the disclosures of which are incorporated herein by reference. Methods of the invention may be executed using droplet actuator systems, e.g., as described in International Patent Application No. PCT/US2007/009379, entitled "Droplet manipulation systems," filed on May 9, 2007. In various embodiments, the manipulation of droplets by a droplet actuator may be electrode mediated, e.g., electrowetting mediated or dielectrophoresis mediated.

"Droplet operation" means any manipulation of a droplet on a droplet actuator. A droplet operation may, for example, include: loading a droplet into the droplet actuator; dispensing one or more droplets from a source droplet; splitting, separating or dividing a droplet into two or more droplets; transporting a droplet from one location to another in any direction; merging or combining two or more droplets into a single droplet; diluting a droplet; mixing a droplet; agitating a droplet; deforming a droplet; retaining a droplet in position; incubating a droplet; heating a droplet; vaporizing a droplet; condensing a droplet from a vapor; cooling a droplet; disposing of a droplet; transporting a droplet out of a droplet actuator; other droplet operations described herein; and/or any combination of the foregoing. The terms "merge," "merging," "combine," "combining" and the like are used to describe the creation of one droplet from two or more droplets. It should be understood that when such a term is used in reference to two or more droplets, any combination of droplet operations sufficient to result in the combination of the two or more droplets into one droplet may be used. For example, "merging droplet A with droplet B," can be achieved by transporting droplet A into contact with a stationary droplet B, transporting droplet B into contact with a stationary droplet A, or transporting droplets A and B into contact with each other. The terms "splitting," "separating" and "dividing" are not intended to imply any particular outcome with respect to size of the resulting droplets (i.e., the size of the resulting droplets can be the same or different) or number of resulting droplets (the number of resulting droplets may be 2, 3, 4, 5 or more). The term "mixing" refers to droplet operations which result in more homogenous distribution of one or more components within a droplet. Examples of "loading" droplet operations include microdialysis loading, pressure assisted loading, robotic loading, passive loading, and pipette loading. In various embodiments, the droplet operations may be electrode mediated, e.g., electrowetting mediated or dielectrophoresis mediated.

"Filler fluid" means a fluid associated with a droplet operations substrate of a droplet actuator, which fluid is sufficiently immiscible with a droplet phase to render the droplet phase subject to electrode-mediated droplet operations. The filler fluid may, for example, be a low-viscosity oil, such as silicone oil. Other examples of filler fluids are provided in International Patent Application No. PCT/US2006/047486, entitled, "Droplet-Based Biochemistry," filed on Dec. 11, 2006; and in International Patent Application No. PCT/US2008/072604, entitled "Use of additives for enhancing droplet actuation," filed on Aug. 8, 2008.

"Immobilize" with respect to magnetically responsive beads, means that the beads are substantially restrained in position in a droplet or in filler fluid on a droplet actuator. For example, in one embodiment, substantially immobilized beads are sufficiently restrained in position to permit execution of a splitting operation on a droplet, yielding one droplet with substantially all of the beads and one droplet substantially lacking in the beads.

"Magnetically responsive" means responsive to a magnetic field. "Magnetically responsive beads" include or are composed of magnetically responsive materials. Examples of magnetically responsive materials include paramagnetic materials, ferromagnetic materials, ferrimagnetic materials, and metamagnetic materials. Examples of suitable paramagnetic materials include iron, nickel, and cobalt, as well as metal oxides, such as $Fe_3O_4$, $BaFe_{12}O_{19}$, $CoO$, $NiO$, $Mn_2O_3$, $Cr_2O_3$, and CoMnP.

"Washing" with respect to washing a magnetically responsive bead means reducing the amount and/or concentration of one or more substances in contact with the magnetically responsive bead or exposed to the magnetically responsive bead from a droplet in contact with the magnetically responsive bead. The reduction in the amount and/or concentration of the substance may be partial, substantially complete, or even complete. The substance may be any of a wide variety of substances; examples include target substances for further analysis, and unwanted substances, such as components of a sample, contaminants, and/or excess reagent. In some embodiments, a washing operation begins with a starting droplet in contact with a magnetically responsive bead, where the droplet includes an initial amount and initial concentration of a substance. The washing operation may proceed using a variety of droplet operations. The washing operation may yield a droplet including the magnetically responsive bead, where the droplet has a total amount and/or concentration of the substance which is less than the initial amount and/or concentration of the substance. Other embodiments are described elsewhere herein, and still others will be immediately apparent in view of the present disclosure.

The terms "top" and "bottom" are used throughout the description with reference to the top and bottom substrates of the droplet actuator for convenience only, since the droplet actuator is functional regardless of its position in space.

When a liquid in any form (e.g., a droplet or a continuous body, whether moving or stationary) is described as being "on", "at", or "over" an electrode, array, matrix or surface, such liquid could be either in direct contact with the electrode/array/matrix/surface, or could be in contact with one or more layers or films that are interposed between the liquid and the electrode/array/matrix/surface.

When a droplet is described as being "on" or "loaded on" a droplet actuator, it should be understood that the droplet is arranged on the droplet actuator in a manner which facilitates using the droplet actuator to conduct one or more droplet operations on the droplet, the droplet is arranged on the droplet actuator in a manner which facilitates sensing of a property of or a signal from the droplet, and/or the droplet has been subjected to a droplet operation on the droplet actuator.

DESCRIPTION

The invention provides droplet actuators having specialized configurations for manipulation of droplets including beads and/or for manipulation of beads in droplets. In certain embodiments, the droplet actuators of the invention include magnets and/or physical barriers manipulation of droplets including beads and/or for manipulation of beads in droplets. The invention also includes methods of manipulating of droplets including beads and/or for manipulation of beads in droplets, as well as methods of making and using the droplet actuators of the invention. The droplet actuators of the invention are useful for, among other things, conducting assays for qualitatively and/or quantitatively analyzing one or more components of a droplet. Examples of such assays include affinity based assays, such as immunoassays; enzymatic assays; and nucleic acid assays. Other aspects of the invention will be apparent from the ensuing discussion.

7.1 Incubation of Beads

In certain embodiments, the invention provides droplet actuators and methods for incubating beads. For example, a sample including bead-containing antibodies may be incubated on the droplet actuator in order to permit one or more target components to bind to the antibodies. Examples of target components include analytes; contaminants; cells, such as bacteria and protozoa; tissues; and organisms, such as multicellular parasites. In the presence of a magnet, magnetic beads in the droplet may be substantially immobilized and may fail to circulate throughout the droplet. The invention provides various droplet manipulations during incubation of droplets on a droplet actuator in order to increase circulation of beads within the droplet and/or circulation of droplet contents surrounding beads. It will be appreciated that in the various embodiments described below employing magnetically responsive beads, beads that are not substantially magnetically responsive may also be included in the droplets.

Figure 1:
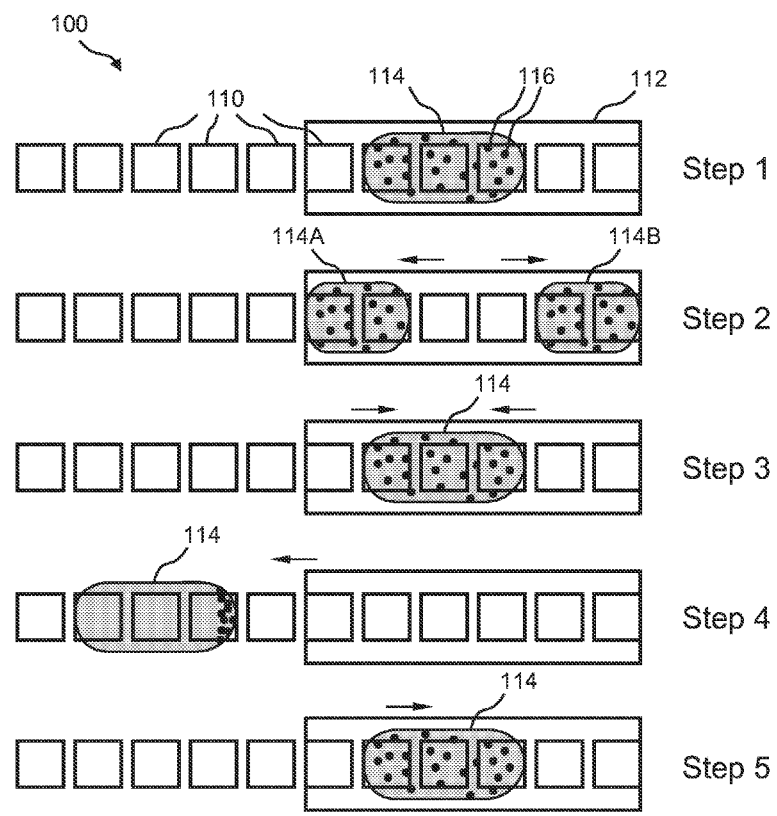
FIG. 1 illustrates a top view of a portion of a droplet actuator useful for incubating a droplet including magnetically responsive beads.

FIG. 1 illustrates techniques that are useful process of incubating a droplet including magnetically responsive beads. Among other things, the techniques are useful for enhancing circulation of fluids and beads within the droplet during an incubation step.

In FIG. 1, each step is illustrated on a path of electrodes 110. A magnet 112 is associated with a subset of electrodes 110. Magnet 112 is arranged relative to the electrodes 110 such that a subset of electrodes 110 are within a uniform region of the magnetic field produced by magnet 112. Bead clumping is reduced when the droplet is present in this uniform region.

In Step 1, droplet 116 is located atop magnet 112. Beads 116 are substantially immobilized in a distributed fashion adjacent to the droplet operations surface. The beads are generally less clumped than they would be in the presence of a non-uniform region of the magnetic field. In Step 2 droplet 114 is split using droplet operations into two sub-droplets 114A, 114B. During the splitting operation beads and liquid are circulated within the droplets 114, 114A and 114B. In Step 3 Droplets 114A and 114B are merged using droplet operations into a single droplet 114. This merging operation is accomplished within the uniform region of the magnetic field. During the merging operation beads and liquid are further circulated within the droplets 114, 114A and 114B.

In Step 4, droplet 114 is transported using droplet operations along electrodes 110 away from the magnet 112. As droplet 116 moves away from magnet 110, beads 116 are pulled to the edge of droplet 114 that nearest the magnet 112. Movement of beads 116 within droplet 114 provides further beneficial circulation of beads and liquid within the droplet 114. In Step 5, droplet 116 is transported using droplet operations back to the step 1 position. Beads 116 within the droplet 116 are again dispersed in the presence of the uniform magnetic field of magnet 112. This redistribution of beads, as droplet 114 returns to its position within the uniform region of the magnetic field provides further beneficial circulation of beads and liquid within the droplet 114.

These steps may be conducted in any logical order. Each step may be conducted any number of times between the other steps. For example, Steps 1-3 may be repeated multiple times before moving onto Step 4. Similarly, Steps 3-5 may be repeated multiple times before returning to Steps 1-3. Moreover, all steps are not required. For example, in one embodiment, an incubation step in an assay is accomplished by repeating Steps 1-3. In another embodiment, an incubation step in an assay is accomplished by repeating Steps 3-5.

The incubation method of the invention is useful for enhancing circulation of magnetically responsive beads with the liquid in a droplet while the droplet remains in the presence of a magnetic field. Among other advantages, the approach may reduce bead clumping and permit tighter droplet actuator designs making more efficient use of droplet actuator real estate.

In one embodiment, the invention provides a droplet operations incubation scheme, that does not allow magnetically responsive beads to be introduced into a region of the magnetic field which is sufficiently non-uniform to cause bead clumping. In another embodiment, the invention provides a merge-and-split incubation scheme, that does not allow magnetically responsive beads to be introduced into a region of the magnetic field which is sufficiently non-uniform to cause bead clumping. In yet another embodiment, the invention provides a droplet transport incubation scheme, that does not allow magnetically responsive beads to be introduced into a region of the magnetic field which is sufficiently non-uniform to cause bead clumping.

Any combination of droplet operations which result in effective mixing (e.g., substantially complete mixing) may be chosen. Mixing is complete when it is sufficient for conducting the analysis being undertaken. The droplet may be oscillated in the presence of the uniform region of the magnetic field by transporting the droplet back and forth within the uniform region. In some cases, electrode sizes used for the oscillation may be varied to increase circulation within the droplet. In some cases, droplet operations electrodes are used to effect droplet operations to transport a droplet back and forth or in one or more looping patterns. Preferably the oscillation pattern does not allow to be introduced into a region of the magnetic field which is sufficiently uniform to cause bead clumping.

In some cases, droplet operations are performed at an edge of the magnet to more equally redistribute the magnetically responsive beads. In some cases, droplet operations are performed away from the magnet, followed by transporting the droplet.

Figure 2:
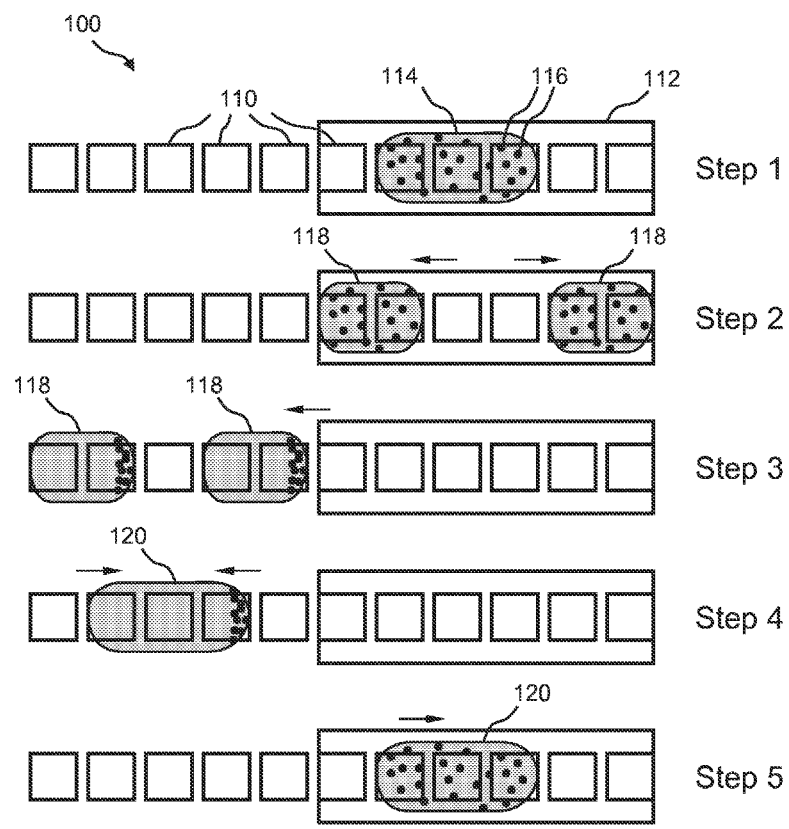
FIG. 2 illustrates a top view of a portion of a droplet actuator useful for incubation of antibodies, wherein a sample and magnetically responsive beads are provided within the magnet field of a magnet.

FIG. 2 illustrates another process of incubation of antibodies, wherein a sample and magnetically responsive beads are provided within the magnet field of a magnet, e.g., within a uniform magnetic field region of a magnet. FIG. 2 shows a top view of a portion of droplet actuator 100 that is described in FIG. 1.

In Step 1, beads 116 are substantially immobilized along the surface of the droplet operations electrodes 110 due to the magnetic field of the magnet 112. I Step 2, droplet 114 is split using droplet operations into two droplets 118, both remaining in the uniform region of the magnetic field. In step 4, the two droplets 118 are transported away from the magnet 112, thereby attracting the beads 116 to the edge of the two droplets 118 nearest the magnet 112. This operation causes flow reversal within the droplets 118, which enhances effective mixing. The two droplets 118 may alternatively be transported away from the magnet in different directions, such as in opposite directions. In Step 4 the two droplets 118 are merged into one droplet 116. In step 5, the droplet 116 is transported back to the step 1 position, causing the beads 116 to disperse within the droplet 116.

Figure 3:
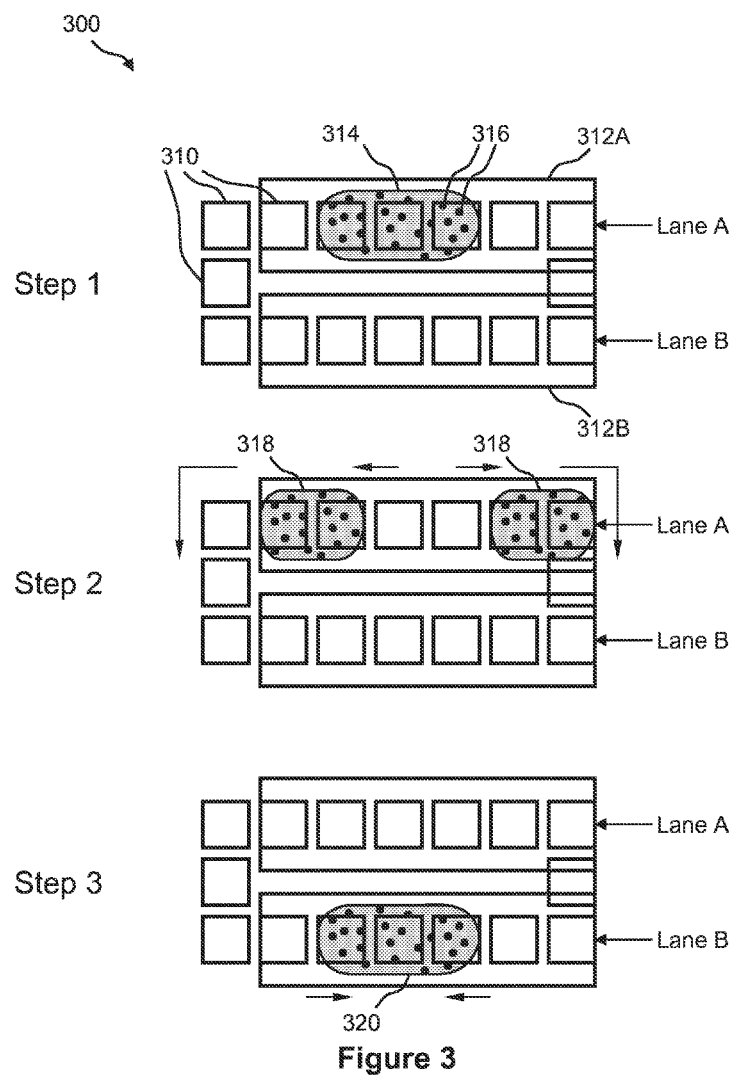
FIG. 3 illustrates a top view of a portion of a droplet actuator useful for incubation of magnetically responsive beads within a droplet, wherein a sample and magnetically responsive beads are subjected to droplet operations within the magnet field of a magnet.

FIG. 3 illustrates another process of incubation of magnetically responsive beads within a droplet, wherein a sample and magnetically responsive beads are subjected to droplet operations within the magnet field of a magnet. FIG. 3 shows a top view of a portion of a droplet actuator 300 that includes a set of droplet operations electrodes 310 (e.g., electrowetting electrodes) that is arranged in sufficient proximity to a magnet, such that a droplet 314 moving along the droplet operations electrodes 310 is within the magnet field of the magnet, e.g., a region of uniform magnetic field. For example, the set of droplet operations electrodes 310 are arranged in a closed loop and in the presence of two magnets, such as a magnet 312A and magnet 312B, as shown in FIG. 3. In this embodiment, the droplet 314 may include sample and beads 316, and some or all of the beads may be magnetically responsive.

In Step 1, sample with beads 316 in the droplet 314 is provided on droplet actuator. Beads 316 are substantially immobilized along the surface of the droplet operations electrodes 310 due to the magnetic field of the first magnet 312A that is located at "lane A" of the electrode loop. In Step 2, the droplet 314 is split using droplet operations into two droplets 318, distributing the beads 316 in the two droplets 318 at "lane A" of the electrode loop. In Step 3, the two droplets 318 are transported using droplet operations in opposite directions away from the first magnet 312A at "lane A" and toward the second magnet 312B that is located at "lane B" of the electrode loop. In Step 4, in the presence of the second magnet 312B at "lane B," droplets 318 are merged into one droplet 320.

In Steps 5-6, not shown, the process of steps 1-3 may be essentially repeated in reverse. In step 5, droplet 320 may be split into two droplets 318, distributing the beads 316 in the two droplets 318 at "lane B." In Step 6, droplets 318 are transported in opposite directions away from the second magnet 312B at "lane B" and back to the first magnet 312A at "lane A." In Step 7, in the presence of the first magnet 312A at "lane A," droplets 318 are merged into one droplet 320.

The droplet split and merge operation as described above provide efficient dispersion of beads in the presence of a magnet, thereby improving the efficiency of the binding of antibodies and the analyte. The various droplet operations may be conducted in primarily or completely in uniform regions of the magnetic fields generated by magnets 312A, 312B. Alternatively, the droplet split and merge operation as described above may be performed away from the magnet and/or near the edge of the magnet.

7.2 Magnet Configurations

Figure 4:
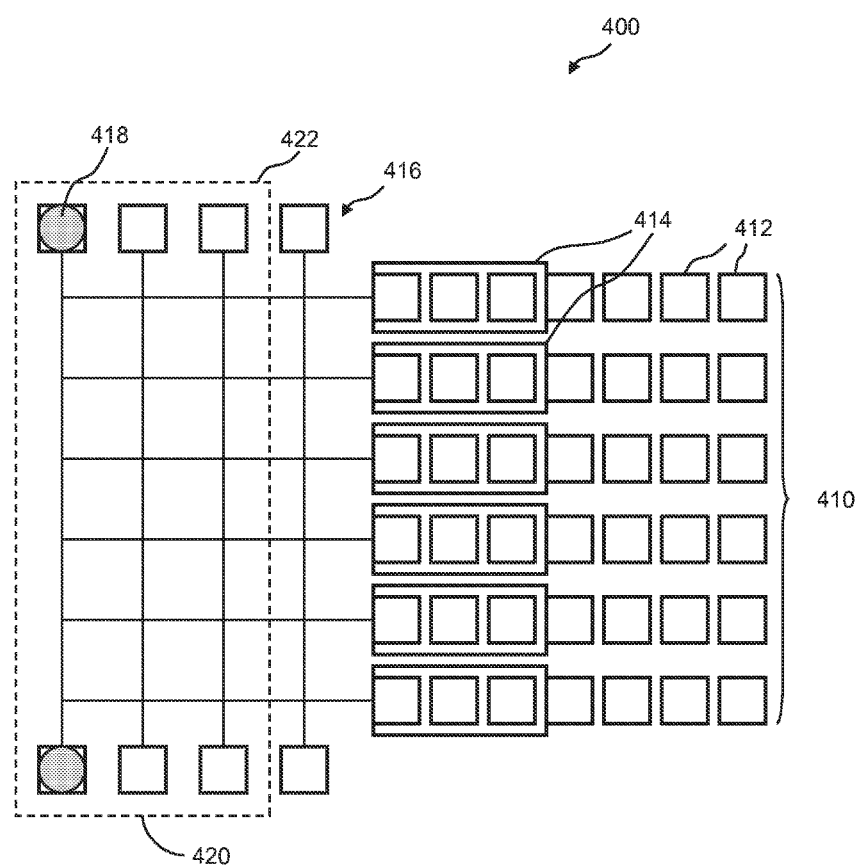
FIG. 4 illustrates a method of shielding the effect of multiple magnets in a droplet actuator by using a magnetic shielding material.

FIG. 4 illustrates a method of shielding the effect of multiple magnets in a droplet actuator 400 by using a magnetic shielding material, preferably one that has high magnetic permeability. One example of such material is Mu-metal foil. Mu-metal is a nickel-iron alloy (e.g., 75% nickel, 15% iron, plus copper and molybdenum) that has very high magnetic permeability. FIG. 4 shows a top view of multiple washing lanes 410, wherein each washing lane 410 includes a string of droplet operations electrodes 412 in the presence of a magnet 414. An electrode array 416 (e.g., an array of electrowetting electrodes) for performing droplet operations feed the multiple washing lanes 410. Additionally, the droplets 418 that are transported may include magnetically responsive beads (not shown). Furthermore, this embodiment provides a magnetic shield 420, provided as a layer that is beneath the electrode array 416.

Because of the presence of multiple magnets 414, which are used to immobilize magnetically responsive beads during washing, the magnetically responsive beads in the reservoir tend to become aggregated, sometimes irreversibly. When bead-containing droplets are dispensed using droplet operations, bead aggregation may cause the number of beads that are present in each dispensed droplet to vary. Variation in bead dispensing may affect the assay result, which is not desirable. The invention, as shown in FIG. 4, provides magnetic shield 420 in the area under the electrode array 416 of the droplet actuator 400. The magnetic shield 420 may be formed of alloys, such as Mu-metal foil, which shields the magnetically responsive beads within the electrode array 416 from stray magnetic fields 422.

Figure 5:
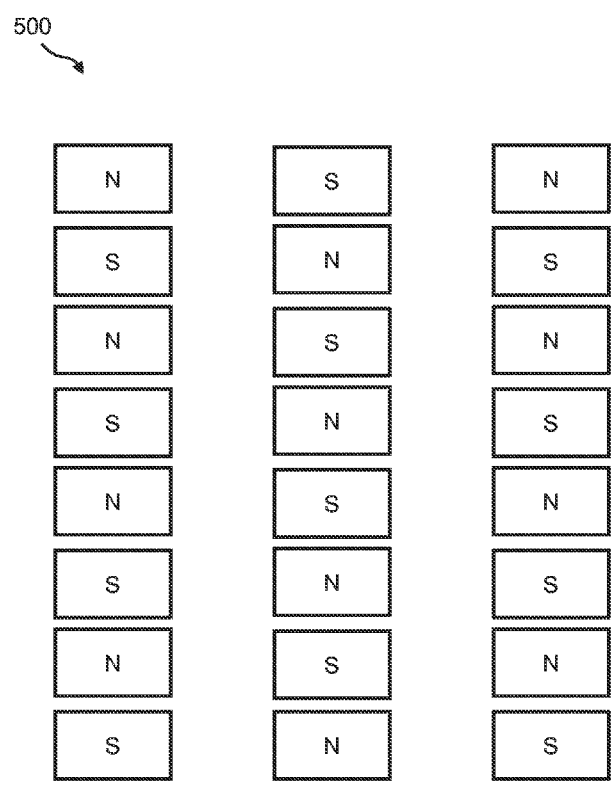
FIG. 5 illustrates a magnet array for performing multiple immunoassays.

FIG. 5 illustrates a magnet array 500 for performing multiple immunoassays that has reduced, preferably substantially no, interference due to adjacent magnets within a droplet actuator (not shown) having a substrate associated with droplet operations electrodes. The electrodes are arranged for conducting one or more droplet operations on a droplet operations surface of the substrate. Magnets, such as the magnet array 500 shown in FIG. 5, may be arranged with respect to the droplet actuator such that one or more magnets cancels out some portion of a magnetic field of one or more other magnets. In this manner, an area of the surface may have some portions that are subject to magnetic fields and some portions in which the magnetic fields have been cancelled out. For example, magnets may be arranged to cancel the field in areas of the droplet actuator that includes liquid along with magnetically responsive beads. Specifically reservoirs, incubation regions, detection regions are preferably in regions in which the magnetic fields have been cancelled out.

In one embodiment, the arrangement involves an array of alternately placed magnets, e.g., as shown in FIG. 5. In general, magnets may be located in any position which supplies a magnetic field to the vicinity of the droplet operations surface where the magnetic field is desired and eliminates or weakens the magnetic field in other areas where the magnetic field is not desired. In one embodiment, a first magnet produces a first magnetic field where it is desirable to immobilize magnetically responsive beads in a droplet, while a second magnet produces a second magnetic field which cancels or weakens a portion of the first magnetic field. This arrangement produces a device in which a portion of the droplet operations surface that would have otherwise been influenced by the first magnetic field is subjected to a weak or absent field because the first magnetic field has been cancelled or weakened by the second magnetic field.

In one embodiment, one or more of the magnets is fixed in relation to the droplet operations surface, and the invention comprises conducting one or more droplet operations using droplets that contain magnetically responsive beads, where the droplets are in proximity to one or more magnets and are in the presence or absence of a magnetic field.

In another embodiment, the magnetic field exerts sufficient influence over magnetically responsive beads that the droplets may be substantially immobile during one droplet operation, such as a splitting operation, and yet not so stable that the droplets are restrained from being transported away from the magnetic field with the magnet. In this embodiment, the droplet may be surrounded by a filler fluid, and yet the droplet with the magnetically responsive beads may be transported away from the magnetic with substantially no loss of magnetically responsive beads to the filler fluid.

Figure 6:
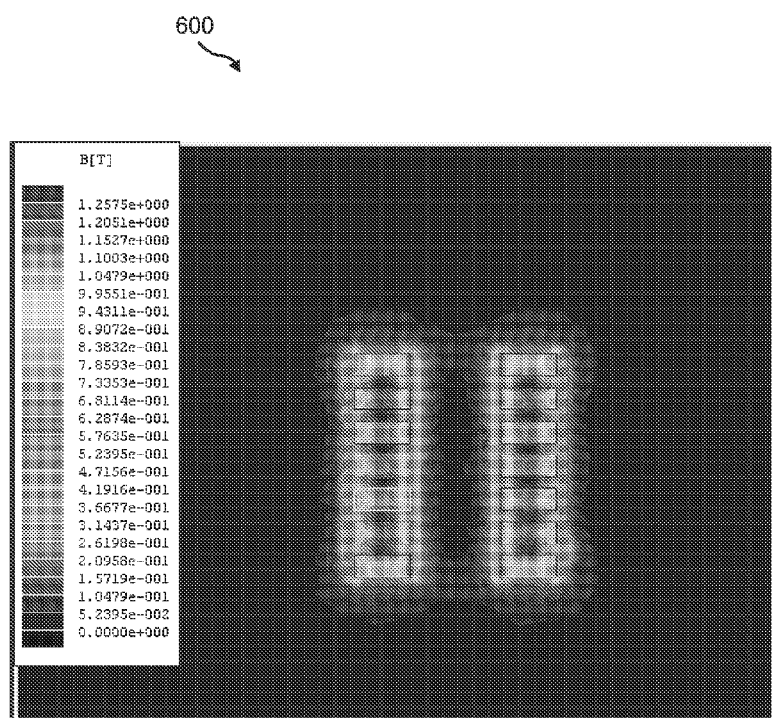
FIG. 6 illustrates simulation results that show the surface field of 2 columns of the magnet array of FIG. 5.

FIG. 6 illustrates simulation results 600 that show the surface field of 2 columns of magnet array 500 of FIG. 5.

7.3 Resuspension of Beads within a Reservoir

Figure 7:
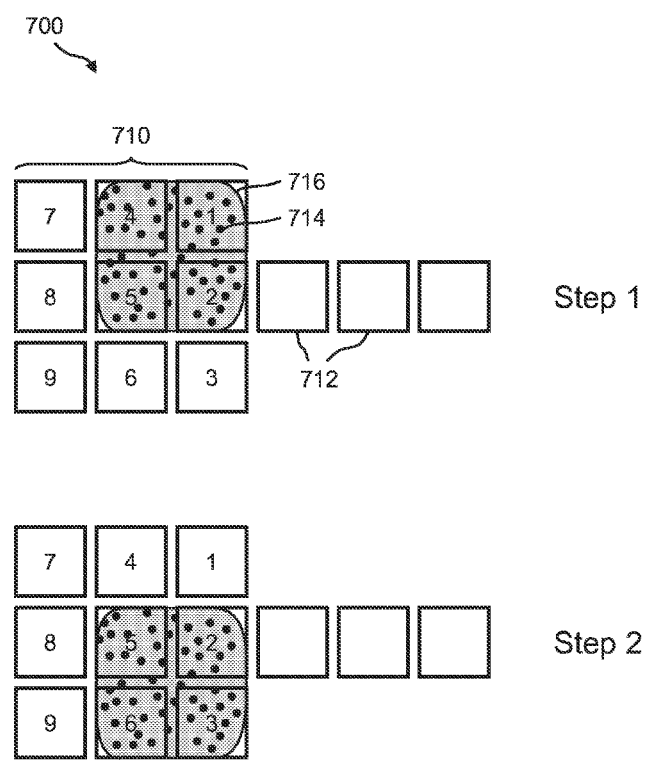
FIG. 7 illustrates a top view of a portion of a droplet actuator useful for resuspension of beads (e.g., magnetically-responsive beads) within a reservoir configured with multiple electrodes.

FIG. 7 illustrates a process of resuspension of beads (e.g., magnetically-responsive beads) within a reservoir configured with multiple electrodes within the. FIG. 7 shows a top view of a portion of a droplet actuator 700 that includes a reservoir 710 that is formed of multiple electrodes (e.g., electrodes 1 through 9 in a 3×3 array), whereby the reservoir 710 feeds a line of droplet operations electrodes 712 (e.g., electrowetting electrodes) to which droplets that contain beads may be dispensed.

Referring to FIG. 7, a process of resuspension of beads within a reservoir by having multiple electrodes within the same reservoir may include, but is not limited to, the following steps. In Step 1, beads 714 are aggregated within the solution 716 due to the presence of multiple magnets (not shown). In Step 2, electrodes within the reservoir 710 are used to subject the solution 716 to droplet operations, thereby resuspension of the beads 714. The electrode activation sequence may be randomized to create more chaotic flow fields for more efficient resuspension. The liquid may be split and merged and subjected to other droplet operations.

During the above-described process, the electrode activation sequence may be chosen such that the beads are mixed well by means of droplet operations. Additionally, when dispensing (e.g., pulling out a finger of fluid) a bead droplet from the electrode array of the reservoir, all the electrodes within the reservoir may be switched ON and OFF at the same time, depending on the requirement. It should be noted that an almost infinite variety of electrode shapes is possible. Any shape which is capable of facilitating a droplet operation will suffice.

The resuspension process may be repeated between every 1, 2, 3, 4, 5 or more droplet dispensing operations. The resuspend-and-dispense pattern may be adjusted as required based on the specific characteristics of bead types and droplet compositions. For example, in one embodiment, the process of the invention results in dispensing bead-containing droplets with greater than 95% consistency in bead count. In another embodiment, the process of the invention results in dispensing bead-containing droplets with greater than 99% consistency in bead count. In another embodiment, the process of the invention results in dispensing bead-containing droplets with greater than 99.9% consistency in bead count. In another embodiment, the process of the invention results in dispensing bead-containing droplets with greater than 99.99% consistency in bead count.

Figure 8:
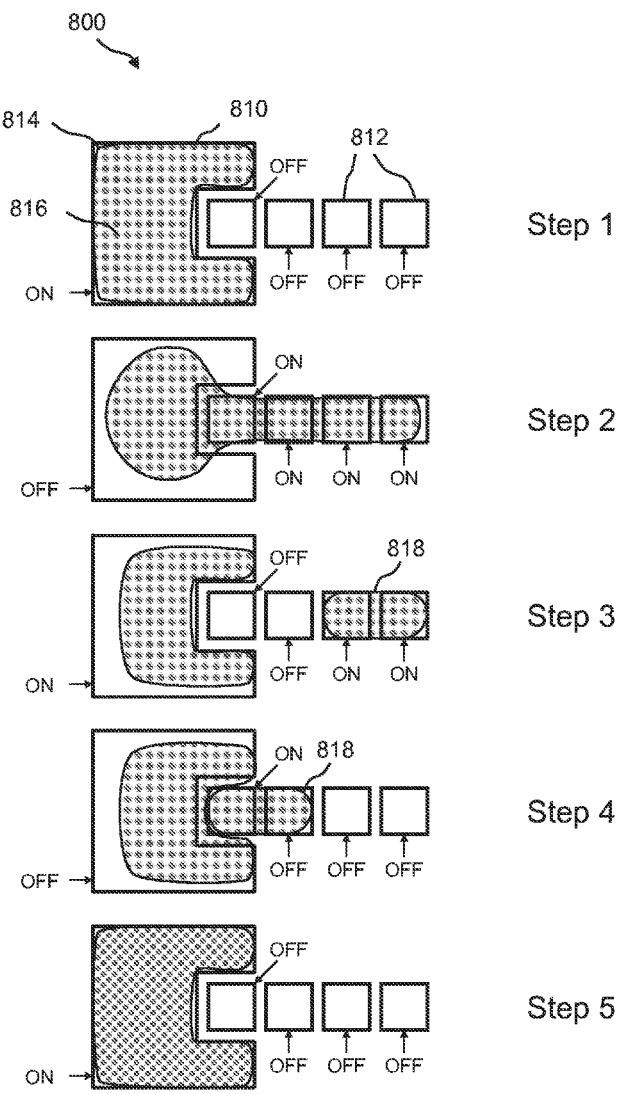
FIG. 8 illustrates a shows a top view of a portion of a droplet actuator useful for resuspending beads (e.g., magnetically-responsive beads) within a reservoir by pushing out a finger of liquid and then merging back.

FIG. 8 illustrates a process of resuspending beads (e.g., magnetically-responsive beads) within a reservoir by pushing out a finger of liquid and then merging back. FIG. 8 shows a top view of a portion of a droplet actuator 800 that includes a reservoir 810 that feeds a line of droplet operations electrodes 812 (e.g., electrowetting electrodes) to which droplets that contain beads may be dispensed. Additionally, the reservoir includes a solution 814 that includes beads 816. Referring to FIG. 8, a process of resuspension of beads within a reservoir by pushing out a finger of liquid and then merging back may include, but is not limited to, the following steps.

In Step 1, beads 816 are aggregated within the solution 814 due to the presence of multiple magnets (not shown). In Step 2, a finger of solution 814 that includes beads 816 is pulled out of the reservoir 810 using droplet operations. In Step 3, a 2× slug 818 is dispensed by splitting the middle of the finger of solution 814. In Step 4, the 2× slug 818 is merged back with the solution 814 that includes magnetically responsive beads 816 within the reservoir 810.

Steps 2 through 4 may be repeated until the desired degree of resuspension is achieved, e.g., until substantially completely resuspended beads are obtained within the bead solution of the reservoir 810. When the desired degree of resuspension is achieved, bead-containing droplets may be dispensed, achieving a target percentage of variation in each droplet.

The resuspension process may be repeated, between every 1, 2, 3, 4, 5 or more droplet dispensing operations. The resuspend-and-dispense pattern may be adjusted as required based on the specific characteristics of bead types and droplet compositions. For example, in one embodiment, the process of the invention results in dispensing bead-containing droplets with greater than 95% consistency in bead count. In another embodiment, the process of the invention results in dispensing bead-containing droplets with greater than 99% consistency in bead count. In another embodiment, the process of the invention results in dispensing bead-containing droplets with greater than 99.9% consistency in bead count. In another embodiment, the process of the invention results in dispensing bead-containing droplets with greater than 99.99% consistency in bead count.

Figure 9:
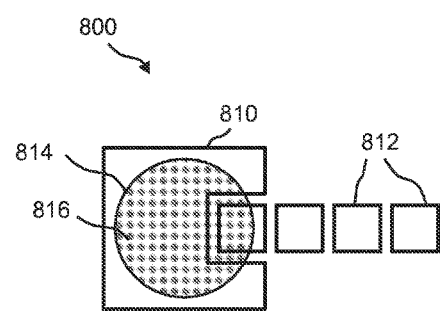
FIG. 9 illustrates a top view of a portion of the droplet actuator of FIG. 8 including a reservoir in which beads are resuspended by applying high frequency voltage to the reservoir electrode.

FIG. 9 illustrates a reservoir in which beads are resuspended by applying high frequency voltage to the reservoir electrode. The figure shows a top view of a portion of droplet actuator 800 of FIG. 8. Reservoir 810 includes a droplet 814 that includes magnetically responsive beads 816. Beads 816 in a reservoir 810 may tend to become aggregated due to, for example, the presence of nearby magnets (not shown). Aggregation may adversely affect bead count in dispensed beads, adversely impacting reliability of assay results for assays conducted using the dispensed bead-containing droplets. Beads 816 may be resuspended within the magnetically responsive bead solution within the reservoir 810 by applying a high frequency AC voltage to the reservoir electrode 810, in accordance with the invention. Because of the high frequency AC voltage, the magnetically responsive beads 816 tend to oscillate because of the wetting and dewetting of the contact line of the droplet. This oscillation at the periphery disperses the magnetically responsive beads 816 and resuspends them in the supernatant. In one example, the high frequency AC voltage may be in the range from about 100 volts to about 300 volts with a frequency from about 10 Hz to about 1000 Hz.

The resuspension process may be repeated between every 1, 2, 3, 4, 5 or more droplet dispensing operations. The resuspend-and-dispense pattern may be adjusted as required based on the specific characteristics of bead types and droplet compositions. For example, in one embodiment, the process of the invention results in dispensing bead-containing droplets with greater that 95% consistency in bead count. In another embodiment, the process of the invention results in dispensing bead-containing droplets with greater than 99% consistency in bead count. In another embodiment, the process of the invention results in dispensing bead-containing droplets with greater than 90.9% consistency in bead count. In another embodiment, the process of the invention results in dispensing bead-containing droplets with greater than 90.99% consistency in bead count.

Figure 10:
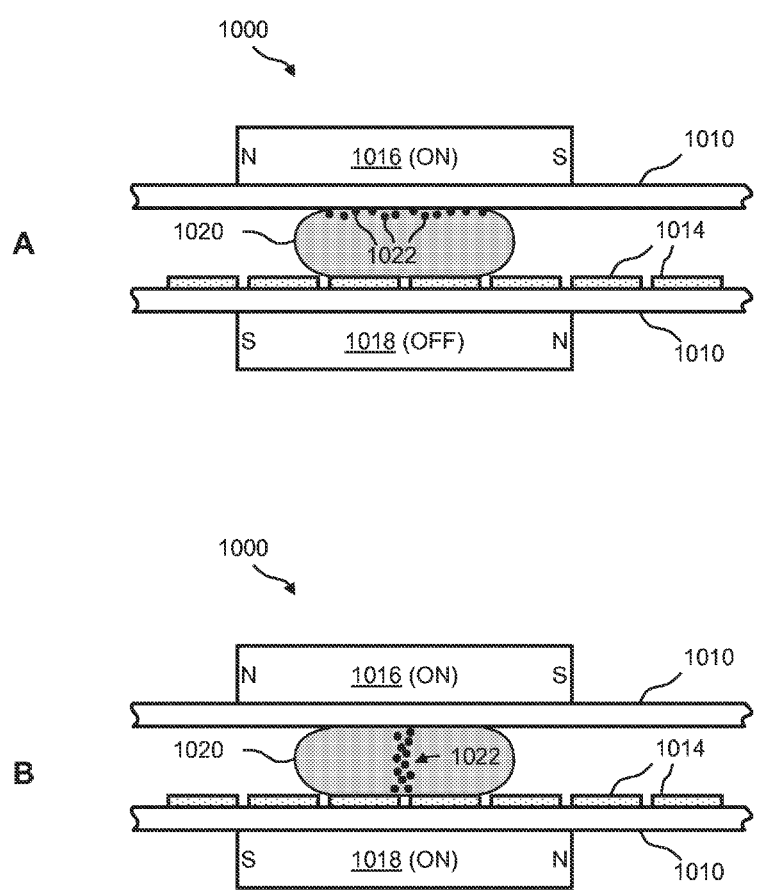
FIG. 10 illustrates a side view of a droplet actuator that includes a top substrate and bottom substrate separated by a gap.

7.4 Improving Dispersion of Magnetically Responsive Beads by Magnet Configurations FIG. 10 illustrates a side view of a droplet actuator 1000 that includes a top substrate 1010 and bottom substrate 1012 that are separated by a gap. A set of droplet operations electrodes 1014 (e.g., electrowetting electrodes) is provided on the bottom substrate 1012. Additionally, a first electromagnet 1016 is arranged near the top substrate 1010 and a second electromagnet 1018 is arranged near the bottom substrate 1012. The proximity of the electromagnets 1016 and 1018 to the droplet actuator 1000 is sufficiently close that the gap is within the magnetic fields thereof. A droplet 1020 that includes magnetically responsive beads 1022 is in the gap and may be manipulated along the droplet operations electrodes 1014.

Electromagnets 1016 and 1018 may be used to improve dispersion of magnetically responsive beads 1022. Improved dispersion may, for example, improve binding efficiency of antibodies and analytes to the surface of the beads. By providing an electromagnet on the top and bottom of the droplet 1020, the magnetically responsive beads 1022 may be effectively dispersed within the droplet 1020 by switching ON and OFF the magnetic fields of electromagnets 1016 and 1018. In one example, FIG. 10A shows the electromagnet 1016 turned ON and the electromagnet 1018 turned OFF, which causes the beads 1022 to be attracted to the electromagnet 1016 and are, therefore, pulled to the electromagnet 1016 side of the droplet 1020. Subsequently, electromagnet 1018 is turned ON and electromagnet 1016 is turned OFF, which causes the beads 1022 to be attracted to electromagnet 1018 and are, therefore, pulled to the electromagnet 1018 side of the droplet 1020. Alternating the activation of electromagnets 1016 and 1018 may be repeated until resuspension of the beads 1022 is substantially achieved. FIG. 10B shows both electromagnets 1016 and 1018 turned ON at the same time, which causes a pillar of beads 1022 to form through droplet 1020. Various changes in the configuration of magnet activation (ON/ON, ON/OFF, OFF/ON, and OFF/OFF) may be used to circulate magnetically responsive beads 1022 within droplet 1020. In some embodiments, the pattern of magnet activation may be randomized. Examples include ON/OFF, OFF/ON, ON/OFF, OFF/ON, ON/OFF, etc.; ON/ON, ON/OFF, OFF/ON, ON/ON, ON/OFF, OFF/ON, ON/ON, ON/OFF, OFF/ON, etc; ON/ON, ON/OFF, OFF/ON, OFF/OFF, ON/ON, ON/OFF, OFF/ON, OFF/OFF, ON/ON, ON/OFF, OFF/ON, OFF/OFF, etc.; ON/OFF, OFF/OFF, OFF/ON, OFF/OFF, ON/OFF, OFF/OFF, OFF/ON, OFF/OFF, ON/OFF, OFF/OFF, OFF/ON, OFF/OFF, etc. Various other magnet activation patterns will be apparent to one of skill in the art in light of the present specification.

Figure 11:
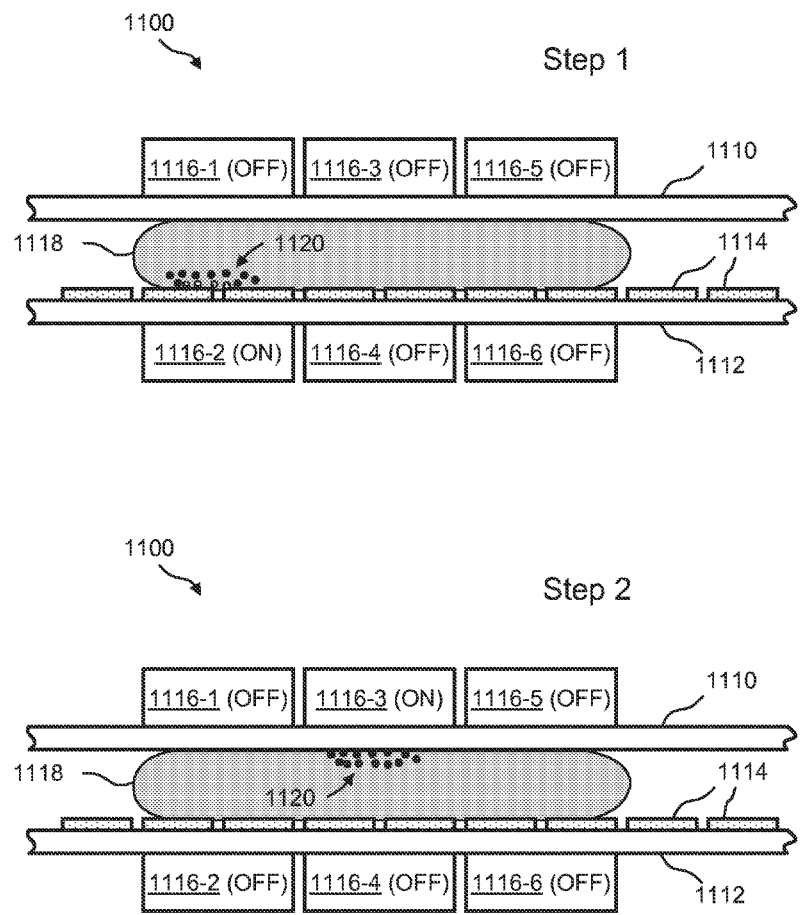
FIG. 11 illustrates a side view of another embodiment of a droplet actuator including a top substrate and bottom substrate separated by a gap.

FIG. 11 illustrates a side view of a droplet actuator 1100 including a top substrate 1110 and bottom substrate 1112 that are separated by a gap. A set of droplet operations electrodes 1114 (e.g., electrowetting electrodes) is provided on the bottom substrate 1112. Additionally, multiple magnets 1116 are arranged near the top substrate 1110 and multiple magnets 1116 are arranged near the bottom substrate 1112. In one example, magnets 1116-1, 1116-3, and 1116-5 are arranged near the top substrate 1110 and magnets 1116-2, 1116-4, and 1116-6 are arranged near the bottom substrate 1112. The proximity of the magnets 1116 to the droplet actuator 1100 is sufficiently close that the gap is within the magnetic fields thereof. A slug of liquid 1118 (e.g., antibodies sample mixture) that includes magnetically responsive beads 1120 is in the gap along the droplet operations electrodes 1114. This aspect of the invention may improve the binding of analytes or other target substances, such as cells, with antibodies that are present on the beads 1120.

Referring to FIG. 11, a process of providing improved dispersion of magnetically responsive beads by use of a magnet arrangement, such as shown in FIG. 11, may include, but is not limited to, the following steps.

Step 1: Magnet 1116-1=OFF, magnet 1116-2=ON, magnet 1116-3=OFF, magnet 1116-4=OFF, magnet 1116-5=OFF, and magnet 1116-6=OFF, which causes the magnetically responsive beads 1120 to be attracted toward magnet 1116-2.

Step 2: Magnet 1116-1=OFF, magnet 1116-2=OFF, magnet 1116-3=ON, magnet 1116-4=OFF, magnet 1116-5=OFF, and magnet 1116-6=OFF, which causes the magnetically responsive beads 1120 to be attracted toward magnet 1116-3.

Step 3 (not shown): Magnet 1116-1=OFF, magnet 1116-2=OFF, magnet 1116-3=OFF, magnet 1116-4=OFF, magnet 1116-5=OFF, and magnet 1116-6=ON, which causes the magnetically responsive beads 1120 to be attracted toward magnet 1116-6.

Step 4 (not shown): Magnet 1116-1=OFF, magnet 1116-2=OFF, magnet 1116-3=OFF, magnet 1116-4=OFF, magnet 1116-5=ON, and magnet 1116-6=OFF, which causes the magnetically responsive beads 1120 to be attracted toward magnet 1116-5.

Step 5 (not shown): Magnet 1116-1=OFF, magnet 1116-2=OFF, magnet 1116-3=OFF, magnet 1116-4=ON, magnet 1116-5=OFF, and magnet 1116-6=OFF, which causes the magnetically responsive beads 1120 to be attracted toward magnet 1116-4.

Step 6 (not shown): Magnet 1116-1=ON, magnet 2=OFF, magnet 3=OFF, magnet 4=OFF, magnet 5=OFF, and magnet 6=OFF, which causes the magnetically responsive beads to be attracted toward magnet 1.

Steps 1 through 6 may be repeated until a desired degree of dispersion or circulation of magnetically responsive beads 1120 and liquid is achieved.

Figure 12:
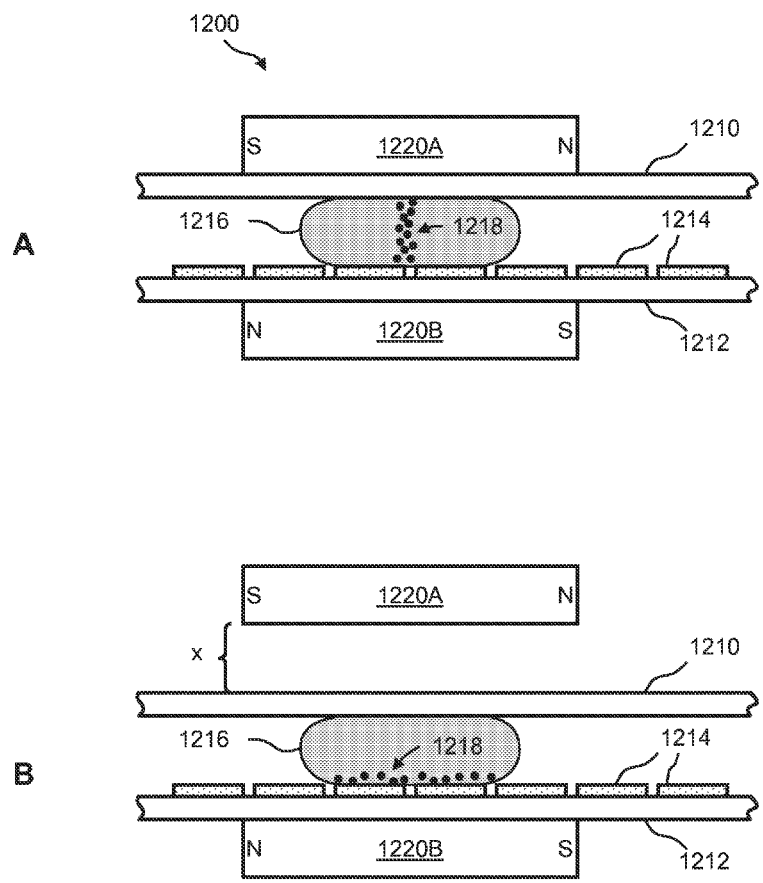
FIG. 12 illustrates a side view of yet another embodiment of a droplet actuator that includes a top substrate and bottom substrate separated by a gap.

FIG. 12 illustrates a side view of a droplet actuator 1200 that includes a top substrate 1210 and bottom substrate 1212 that are separated by a gap. A set of droplet operations electrodes 1214 (e.g., electrowetting electrodes) is provided on the bottom substrate 1212. A droplet 1216 that includes magnetically responsive beads 1218 is provided in the gap and may be manipulated along the droplet operations electrodes 1214. Additionally, a first magnet 1220A is arranged near the top substrate 1210 and a second magnet 1220B is arranged near the bottom substrate 1212. The proximity of the magnets 1220A and 1220B to the droplet actuator 1200 is sufficiently close that the gap is within the magnetic fields thereof. However, the distance of the magnets 1220A and 1220B from the droplet actuator 1200 may be adjusted by, for example, a mechanical means, thereby adjusting the influence of the magnetic fields upon the magnetically responsive beads 1218.

Mechanical movement of the magnets 1220A and 1220B disperses or otherwise circulates magnetically responsive beads and liquids within the droplet. In one example, FIG. 12A shows both magnets 1220A and 1220B in close proximity to the droplet actuator 1200, which causes a pillar of beads 1218 to form through the droplet 1216. In another example, FIG. 12B shows the magnet 1220A only may be moved mechanically by a distance "x" where substantially no magnetic field of magnet 1220A reaches the magnetically responsive beads 1218 and, thus, the beads 1218 are attracted toward the magnet 1220B, thereby dispersing the beads 1218. In like manner, the magnet 1220B only may be moved mechanically by a distance "x" where substantially no magnetic field of magnet 1220B reaches the magnetically responsive beads 1218 and, thus, the beads are attracted toward the first magnet 1220A, thereby dispersing the beads 1218. By, for example, alternating the mechanical movement of the magnets, effective dispersion of magnetically responsive beads 1218 is substantially ensured. In some embodiments, both magnets are moved. Magnets may be oscillated to rapidly circulate beads and liquids within the droplet.

7.5 Improved Droplet Splitting by Magnet Configurations

Figure 13:
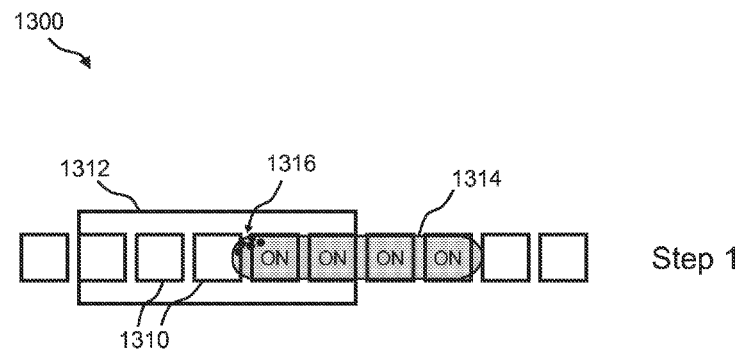
FIG. 13 illustrates a top view of a portion of a droplet actuator useful for a process of asymmetrically splitting a droplet.
Figure 13:
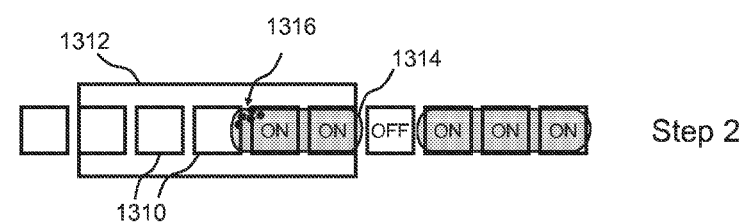

FIG. 13 illustrates a process of asymmetrically splitting a droplet. FIG. 13 shows a top view of a portion of a droplet actuator 1300 that includes a set of droplet operations electrodes 1310 (e.g., electrowetting electrodes) that is arranged in sufficient proximity to a magnet 1312, such that a droplet 1314 moving along the droplet operations electrodes 1310 is within the magnet field of the magnet 1312, e.g., a region of uniform magnetic field. In this embodiment, the droplet 1314 may be may include sample and beads 1316, and some or all of the beads 1316 may be magnetically responsive.

The process may include, without limitation, the following steps. In step 1, after immobilizing the magnetically responsive beads 1316 to a localized area in the presence of magnet 1312, droplet operations electrodes 1310 are activated to extend droplet 1314 into a 4×-slug of liquid that extends beyond the boundary of magnet 1312. In Step 2, droplet operations electrode 1310 is deactivated, and the next two droplet operations electrodes 1310 remain on, and a third droplet operations electrode is activated to provide the asymmetric split. The process may, for example, be employed in a merge-and-split bead washing protocol.

Figure 14:
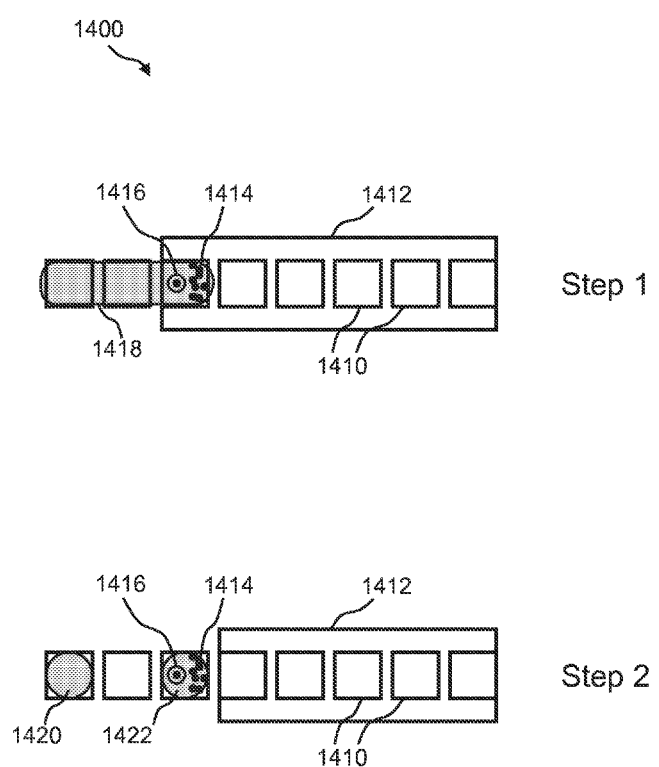
FIG. 14 illustrates a top view of a portion of a droplet actuator useful for a process employing a hydrophilic patch in a droplet splitting operation.

FIG. 14 illustrates a process employing a hydrophilic patch in a droplet splitting operation. FIG. 14 shows a top view of a portion of a droplet actuator 1400 that includes a set of droplet operations electrodes 1410 (e.g., electrowetting electrodes) arranged in sufficient proximity to a magnet 1412, such that a droplet moving along the droplet operations electrodes 1410 is within the magnet field of the magnet 1412, e.g., a region of uniform magnetic field. In this embodiment, the droplet may be may include sample and beads 1414, and some or all of the beads may be magnetically responsive.

The process may include, without limitation, the following steps. In Step 1, a small hydrophilic patch 1416, which is patterned on the top substrate (not shown) and opposite a certain droplet operations electrode 1410, immobilizes the aqueous slug 1418, and the magnet 1412 immobilizes the magnetically responsive beads 1414. In Step 2, a droplet splitting operation is executed (e.g., forming droplets 1420 and 1422). The hydrophilic patch 1416 ensures droplet splitting at the same point in relation to the droplet operations electrode 1410 that is downstream of the hydrophilic patch 1416. In this example, the magnetically responsive beads 1414 remain substantially immobilized in droplet 1422 by the magnet 1412 and droplet 1522 is substantially free of beads 1420. The process may, for example, be employed in a merge-and-split bead washing protocol.

Figure 15:
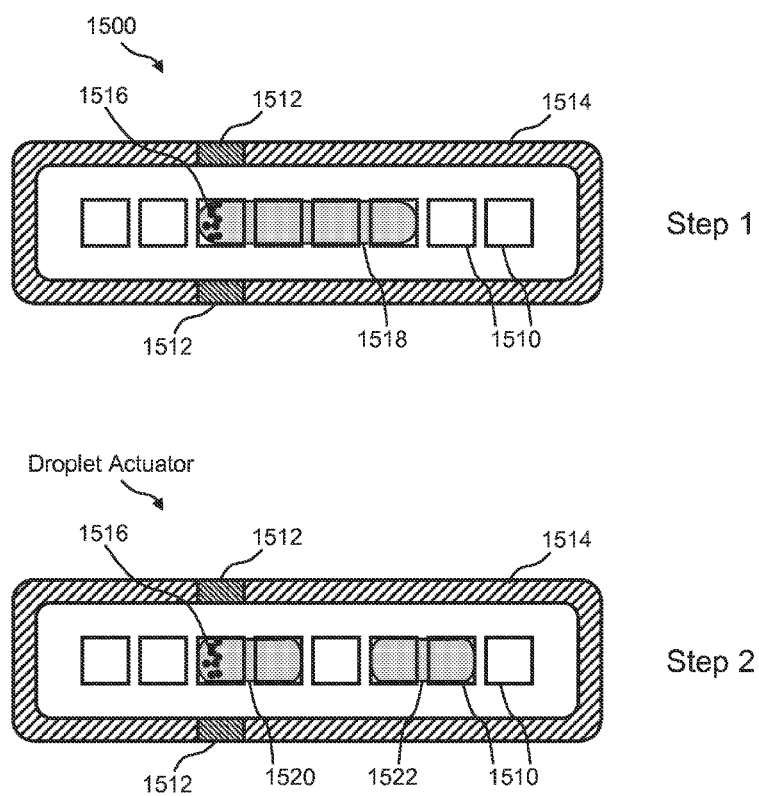
FIG. 15 illustrates a top view of a portion of a droplet actuator useful for a process of using a magnetic strip that is integrated into the gasket material at the point of bead immobilization.

FIG. 15 illustrates a process of using a magnetic strip that is integrated into the gasket material at the point of bead immobilization. FIG. 15 shows a top view of a portion of a droplet actuator 1500 that includes a set of droplet operations electrodes 1510 (e.g., electrowetting electrodes) that is arranged in sufficient proximity to a magnetic strip 1512 that is integrated into the gasket material 1514 of the droplet actuator 1500, such that a droplet moving along the droplet operations electrodes 1510 is within the magnet field of the magnetic strip 1512, e.g., a region of uniform magnetic field. In this embodiment, the droplet may be may include sample and beads 1516, and some or all of the beads may be magnetically responsive.

The process may include, but is not limited to, the following steps. In Step 1, magnetic strip 1512 immobilizes the magnetically responsive beads 1516 in an aqueous slug 1518. In Step 2, a droplet splitting operation occurs (e.g., forming droplets 1520 and 1522), whereby the magnetically responsive beads 1516 remain substantially immobilized in droplet 1520 by the magnetic strip 1512 and droplet 1522 is substantially free of beads 1516. The process may, for example, be employed in a merge-and-split bead washing protocol.

7.6 Improved Droplet Splitting by Physical Barrier

Figure 16:
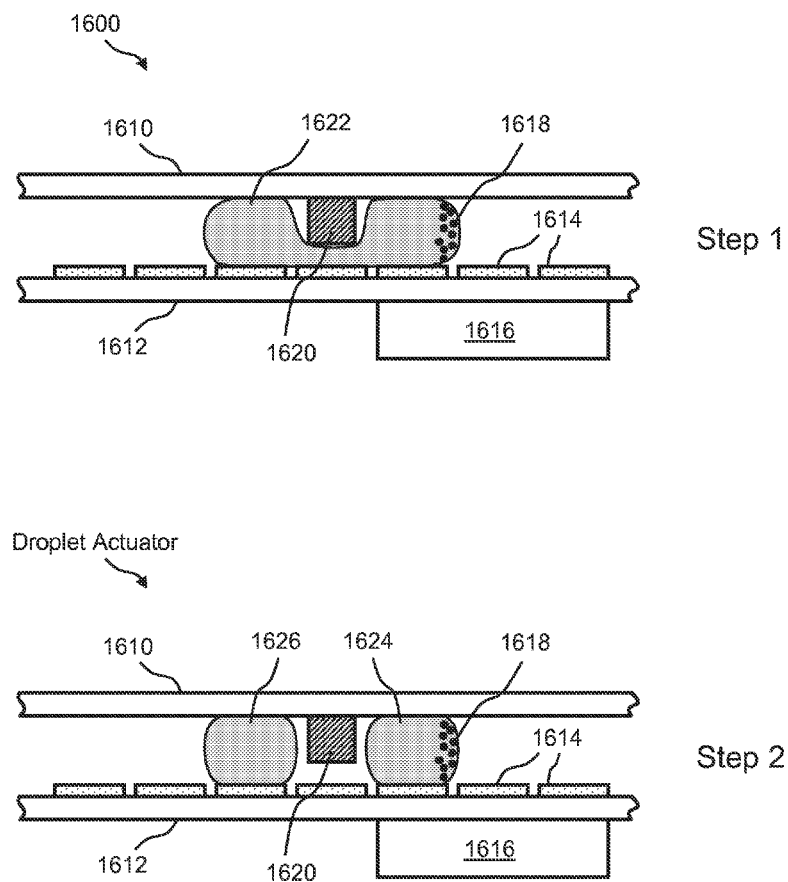
FIG. 16 illustrates a side view of a droplet actuator that includes a top substrate and bottom substrate that are separated by a gap useful for facilitating consistent droplet splitting by use of a physical barrier in the droplet actuator.

FIG. 16 illustrates a process of facilitating consistent droplet splitting by use of a physical barrier in the droplet actuator. FIG. 16 shows a side view of a droplet actuator 1600 that includes a top substrate 1610 and bottom substrate 1612 that are separated by a gap. A set of droplet operations electrodes 1614 (e.g., electrowetting electrodes) is provided on the bottom substrate 1612. Additionally, a magnet 1616 is arranged in sufficient proximity to the droplet operations electrodes 1614, such that a droplet moving along the droplet operations electrodes 1610 is within the magnet field of the magnet 1616, e.g., a region of uniform magnetic field. In this embodiment, the droplet may be may include sample and beads 1618, and some or all of the beads 1618 may be magnetically responsive. Additionally, the droplet actuator 1600 includes a physical barrier 1620 that is arranged as shown in FIG. 16. The physical barrier 1620 is used to reduce the gap at the point of splitting, thereby assisting the droplet splitting operation. Additionally, because of the existence of the rigid barrier, consistent splitting may be obtained substantially at the same point. Further, the physical barrier 1620 may in some cases substantially nonmagnetic.

The process may include, but is not limited to, the following steps. In Step 1, magnet 1612 immobilizes the magnetically responsive beads 1618 in, for example, an aqueous slug 1622. The aqueous slug 1622 is intersected by the physical barrier 1620, which reduces the gap. In Step 2, a droplet splitting operation occurs (e.g., forming droplets 1624 and 1626), whereby the magnetically responsive beads 1618 remain substantially immobilized by the magnet 1616 and the physical barrier 1620 is used to reduce the gap at the point of splitting, thereby assisting the droplet splitting operation. In this example, magnetically responsive beads 1618 remain substantially immobilized in droplet 1624 by the magnet 1612 and droplet 1626 is substantially free of beads 1618. For example, substantially all of the magnetically responsive beads 1618 may remain in droplet 1618, while droplet 1610 may be substantially free of magnetically responsive beads 1618. The process may, for example, be employed in a merge-and-split bead washing protocol.

Figure 17:
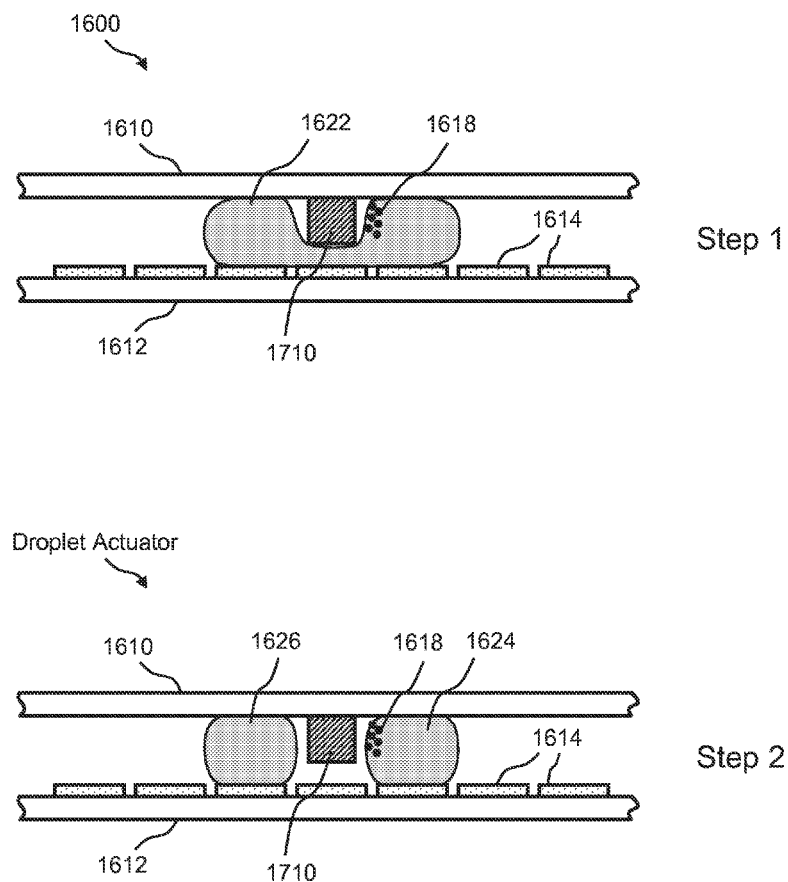
FIG. 17 illustrates a side view of the portion of droplet actuator in FIG. 16 useful for facilitating consistent droplet splitting by use of a magnetic physical barrier in the droplet actuator.

FIG. 17 illustrates a process of facilitating consistent droplet splitting by use of a magnetic physical barrier in the droplet actuator. FIG. 17 shows a side view of the portion of droplet actuator 1600 that is described in FIG. 16. However, FIG. 17 shows that the substantially nonmagnetic physical barrier 1620 of FIG. 16 is replaced with a magnetic physical barrier 1710. FIG. 17 also shows that magnet 1616 of FIG. 16 is removed from proximity to bottom substrate 1612. The magnetic physical barrier 1710 is used to (1) immobilize the magnetically responsive beads 1618 and (2) to reduce the gap at the point of splitting, thereby assisting the droplet splitting operation. Additionally, because of the existence of the rigid magnetic physical barrier 1710, consistent splitting may be obtained substantially at the same point.

The process may include, but is not limited to, the following steps. In Step 1, the magnetic physical barrier 1710 immobilizes the magnetically responsive beads 1618 in the aqueous slug 1622. The aqueous slug 1622 is intersected by the magnetic physical barrier 1710, which reduces the gap. In Step 2, a droplet splitting operation is executed (e.g., forming droplets 1624 and 1626), whereby the magnetically responsive beads remain substantially immobilized by the magnetic physical barrier 1710 and the magnetic physical barrier 1710 is used to reduce the gap at the point of splitting, thereby assisting the droplet splitting operation. In this example, magnetically responsive beads 1618 remain substantially immobilized in droplet 1624 by magnetic physical barrier 1710 and droplet 1626 is substantially free of beads 1618. The process may, for example, be employed in a merge-and-split bead washing protocol.

7.7 Electrode Configurations for Improved Droplet Splitting

Figure 18:
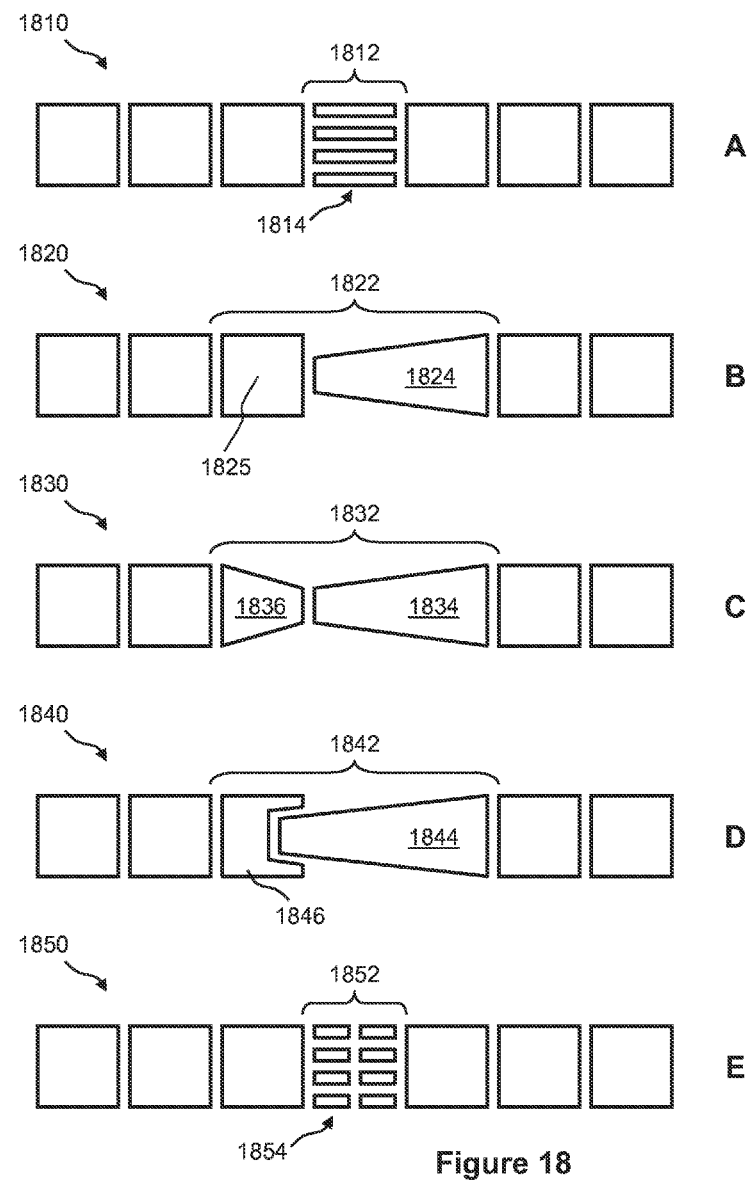
FIG. 18 illustrates embodiments of electrode configuration for improved droplet splitting.

FIG. 18 illustrates embodiments of electrode configuration for improved droplet splitting. In one example, FIG. 18A shows an electrode path 1810 that includes a splitting region 1812 that includes a segmented electrode 1814, such as multiple electrode strips. In a splitting operation, electrodes may be activated to extend a slug across the region of electrode strips. The electrode strips may be deactivated starting with the outer strips and continuing to the inner strips in order to cause a controlled split of the droplet at the electrode strip region of the electrode path 1810. In an alternative embodiment, the electrode strips may be rotated 90 degrees. In this embodiment, deactivation may start from the inner electrodes of the electrode strips and continue to the outer electrodes in order to controllably split the droplet at the electrode strips.

In another example, FIG. 18B shows an electrode path 1820 that includes a splitting region 1822 that includes a tapered electrode 1824 that may span a distance equivalent, for example, to about two standard droplet operations electrodes. In operation, a droplet may be extended along electrodes of the electrode path across tapered electrode 1824. Electrode 1824 or the adjacent electrode 1825 may be deactivated to controllably split the droplet.

In yet another example, FIG. 18C shows an electrode pattern 1830 that includes a splitting region 1832 that includes a long tapered electrode 1834 and a short tapered electrode 1836, where the smallest end of the tapered electrodes face one another. The tapered electrode pair may span a distance equivalent, for example, to about three standard droplet operations electrodes. In operation, a droplet may be extended along electrodes of the electrode path across tapered electrodes 1834 and 1836. Electrode 1834 and/or electrode 1836 may be deactivated to controllably split the droplet.

In yet another example, FIG. 18D shows an electrode pattern 1840 that includes a splitting region 1842 that includes a long tapered electrode 1842 and a short interlocking electrode 1844, where the smallest end of the tapered electrode 1842 faces the interlocking electrode 1844. The electrode pair may span a distance equivalent, for example, to about three standard droplet operations electrodes. In operation, a droplet may be extended along electrodes of the electrode path across tapered electrodes 1844 and 1846. Electrode 1844 and/or electrode 1846 may be deactivated to controllably split the droplet.

In yet another example, FIG. 18E shows an electrode pattern 1850 that includes a splitting region 1852 that includes a segmented electrode 1854, such as multiple row or columns of electrode strips. n operation, a droplet may be extended along electrodes of the electrode path across splitting region 1852. Each segment may be independently deactivated as desired to controllably split the droplet.

7.8 Improved Detection

A process for the detection of supernatant after adding a substrate to the assayed magnetically responsive beads is disclosed, in accordance with the invention. After the washing protocol to remove the excess unbound antibody is complete, a chemiluminescent substrate is added to the assayed and washed beads, which produces chemiluminescence as a result of the reaction between the enzyme on the beads and the substrate.

The substrate may be incubated with the magnetically responsive beads for some fixed time, where the magnetically responsive beads are substantially immobilized and the supernatant is transported away for detection. This approach reduces, preferably entirely eliminates, the need to transport the magnetically responsive bead droplet over long distances to the detector and also reduces, preferably entirely eliminates, the possibility of loss of beads during the transport operation.

Alternatively the antibody-antigen-enzyme complex can be released from the bead by chemical or other means into the supernatant. The beads may then be substantially immobilized and the supernatant processed further for detection.

Additionally, the same split, merge, and transport strategies that are explained for incubating beads/antibodies/sample mixture may be employed here also for incubating substrate and assayed beads.

Bead based sandwich or competitive affinity assays, such as ELISAs, may be performed using the procedures described in this application in conjunction with various steps described in International Patent Application No. PCT/US06/47486, entitled "Droplet-Based Biochemistry," filed on Dec. 11, 2006. Further, after incubation, unbound sample material and excess reporter antibody or reporter ligand may be washed away from the bead-antibody-antigen complex using various droplet operations. A droplet of substrate (e.g., alkaline phosphatase substrate, APS-5) may be delivered to the bead-antibody-antigen complex. During incubation, the substrate is converted to product which begins to chemiluminesce. The decay of the product (which generates light) is sufficiently slow that the substrate-product droplet can be separated from the alkaline phosphatase-antibody complex and still retain a measurable signal. After an incubation period of the substrate with the bead-antibody-antigen complex (seconds to minutes), the magnetically responsive bead-antibody-antigen complex may be retained with a magnetic field (e.g., see U.S. patent application Ser. No. 60/900,653, filed on Feb. 9, 2007, entitled "Immobilization of magnetically-responsive beads during droplet operations,") or by a physical barrier (e.g., see U.S. patent application Ser. No. 60/881,674, filed on Jan. 22, 2007, entitled "Surface-assisted fluid loading and droplet dispensing," the entire disclosure of which is incorporated herein by reference) and only the substrate-product droplet may be presented (using droplet operations) to the sensor (e.g., PMT) for quantitation of the product.

The substrate-product droplet alone is sufficient to generate a signal proportional to the amount of antigen in the sample. Incubation of the substrate with the magnetically responsive bead-antibody-antigen complex produces enough product that can be quantitated when separated from the enzyme (e.g., alkaline phosphatase). By measuring the product in this manner, the bead-antibody-antigen complex does not have to be presented to the PMT. There are no beads or proteins to "foul" the detector area as they are never moved to this area. Also, the product droplet does not have to oscillate over the detector to keep beads in suspension during quantitation. The droplet volume may also be reduced in the absence of beads. Detection of the bead-antibody-antigen complex may employ a slug of liquid (e.g., 4 droplets) to move the complex, whereas with the beadless method the droplet could be smaller (e.g., less than 4 droplets). Time to result may also be shorter with this approach when performing multiplex ELISAs because the product droplet can be moved to the detector more quickly in the absence of beads.

Bead based sandwich or competitive affinity assays, such as ELISAs, may be performed using droplet operations for one or more steps, such as combining sample, capture beads and reporter antibody or reporter ligand. After incubation, unbound sample material and excess reporter antibody or reporter ligand may be washed away from the bead-antibody-antigen complex using an on-chip washing protocol. After washing, a droplet of substrate (e.g., alkaline phosphatase substrate, APS-5) may be delivered to the bead-antibody-antigen complex. During the incubation, the substrate is converted to product which begins to chemiluminesce. The decay of the product (which generates light) is sufficiently slow that the substrate-product droplet can be separated from the alkaline phosphatase-antibody complex and still retain a measurable signal. After an incubation period of the substrate with the bead-antibody-antigen complex (seconds to minutes), the magnetically responsive bead-antibody-antigen complex may be retained with a magnet or by a physical barrier and only the substrate-product droplet may be presented (using droplet operations) to the sensor (e.g., PMT) for quantitation of the product.

The substrate-product droplet alone is sufficient to generate a signal proportional to the amount of antigen in the sample. Incubation of the substrate with the magnetically responsive bead-antibody-antigen complex produces enough product that can be quantitated when separated from the enzyme (e.g., alkaline phosphatase). By measuring the product in this manner, the bead-antibody-antigen complex does not have to be presented to the PMT. There are no beads or proteins to "foul" the detector area as they are never moved to this area. Also, the product droplet does not have to oscillate over the detector to keep beads in suspension during quantitation. The droplet volume may also be reduced in the absence of beads. Detection of the bead-antibody-antigen complex may employ a slug of liquid (e.g., 4 droplets) to move the complex, whereas with the beadless method the droplet could be smaller (e.g., less than 4 droplets). Time to result may also be shorter with this approach when performing multiplex ELISAs because the product droplet can be moved to the detector more quickly in the absence of beads.

Figure 19:
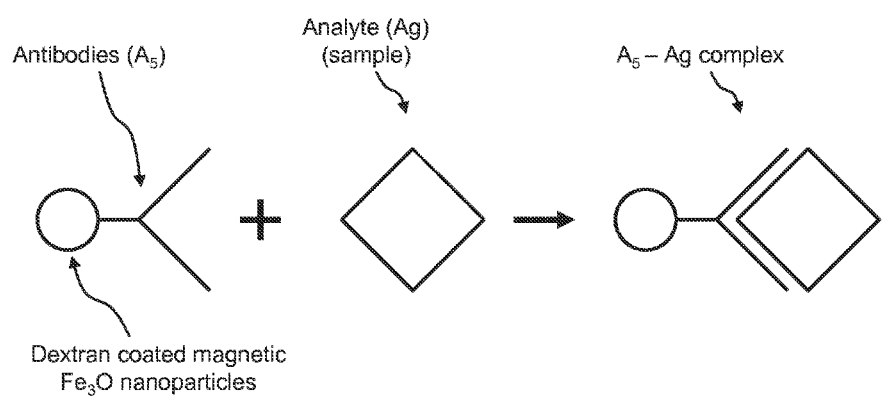
FIG. 19 illustrates detection strategies for quantifying an analyte.

FIG. 19 illustrates detection strategies for quantifying an analyte. In particular, the immunoassay may be developed without any secondary antibody that is labeled with enzyme, fluorophore, or quantum dots. After binding of the analyte to the antibody that is bound to the magnetically responsive beads, the hydrodynamic diameter of the beads increases due to the immune complex that is bound to the surface of the bead. A superconductive quantum interference device (SQUID) gradiometer system may be used in order to measure the standard magnetization (Ms) of magnetically labeled immune complexes, such as the $A_5$-Ag complex shown in FIG. 19.

7.9 Operation Fluids

For examples of fluids that may be subjected to droplet operations using the approach of the invention, see the patents listed in section 2, especially International Patent Application No. PCT/US2006/047486, entitled, "Droplet-Based Biochemistry," filed on Dec. 11, 2006. In some embodiments, the fluid includes a biological sample, such as whole blood, lymphatic fluid, serum, plasma, sweat, tear, saliva, sputum, cerebrospinal fluid, amniotic fluid, seminal fluid, vaginal excretion, serous fluid, synovial fluid, pericardial fluid, peritoneal fluid, pleural fluid, transudates, exudates, cystic fluid, bile, urine, gastric fluid, intestinal fluid, fecal samples, fluidized tissues, fluidized organisms, biological swabs, biological washes, liquids with cells, tissues, multicellular organisms, single cellular organisms, protozoa, bacteria, fungal cells, viral particles, organelles. In some embodiment, the fluid includes a reagent, such as water, deionized water, saline solutions, acidic solutions, basic solutions, detergent solutions and/or buffers. In some embodiments, the fluid includes a reagent, such as a reagent for a biochemical protocol, such as a nucleic acid amplification protocol, an affinity-based assay protocol, a sequencing protocol, and/or a protocol for analyses of biological fluids.

The fluids may include one or more magnetically responsive and/or non-magnetically responsive beads. Examples of droplet actuator techniques for immobilizing magnetically responsive beads and/or non-magnetically responsive beads are described in the foregoing international patent applications and in Sista, et al., U.S. patent application Ser. No. 60/900,653, entitled "Immobilization of Magnetically-responsive Beads During Droplet Operations," filed on Feb. 9, 2007; Sista et al., U.S. patent application Ser. No. 60/969,736, entitled "Droplet Actuator Assay Improvements," filed on Sep. 4, 2007; and Allen et al., U.S. patent application Ser. No. 60/957,717, entitled "Bead Washing Using Physical Barriers," filed on Aug. 24, 2007, the entire disclosures of which is incorporated herein by reference.

CONCLUDING REMARKS

The foregoing detailed description of embodiments refers to the accompanying drawings, which illustrate specific embodiments of the invention. Other embodiments having different structures and operations do not depart from the scope of the present invention. This specification is divided into sections for the convenience of the reader only. Headings should not be construed as limiting of the scope of the invention. The definitions are intended as a part of the description of the invention. It will be understood that various details of the present invention may be changed without departing from the scope of the present invention. Furthermore, the foregoing description is for the purpose of illustration only, and not for the purpose of limitation, as the present invention is defined by the claims as set forth hereinafter.

The invention claimed is:

1. A method comprising:
  substantially immobilizing magnetically responsive beads within a droplet using a magnetic field; and
  using a plurality of droplet operations electrodes to split the droplet into first and second droplets, wherein the first droplet contains at least substantially all of the magnetically responsive beads and the second droplet is at least substantially lacking in magnetically responsive beads, further comprising using a physical barrier to facilitate splitting of the droplet, where the physical barrier reduces a gap distance at a point of splitting.

2. The method of claim 1, wherein using the plurality of droplet operations electrodes to split the droplet into first and second droplets comprises using a hydrophilic patch.

3. The method of claim 1, further comprising using a magnet to generate the magnetic field.

4. The method of claim 1, further comprising using a magnet embedded within a gasket proximate to the droplet operations electrodes to generate the magnetic field.

5. The method of claim 1, further comprising positioning a magnet proximate to a gasket, which in turn is proximate to the droplet operations electrodes to generate the magnetic field.

6. The method of claim 1, further comprising using a magnetized physical barrier to facilitate splitting of the droplet.

7. The method of claim 1, further comprising using a magnetic shielding material to selectively minimize the magnetic field.

8. The method of claim 1, wherein the magnetic field is sufficiently strong to hold the magnetically responsive beads substantially immobile during a droplet operation.

9. The method of claim 1, wherein the magnetic field is sufficiently weak to enable the magnetically responsive beads to be moved away from the magnetic field during a droplet operation.

* * * * *